United States Patent
Li et al.

(10) Patent No.: US 10,370,367 B2
(45) Date of Patent: Aug. 6, 2019

(54) IRAK INHIBITORS AND METHOD FOR MAKING AND USING

(71) Applicant: Rigel Pharmaceuticals, Inc., South San Francisco, CA (US)

(72) Inventors: Hui Li, Santa Clara, CA (US); Thilo Heckrodt, San Francisco, CA (US); Yan Chen, Foster City, CA (US); Ryan Kelley, Pacifica, CA (US); Darren McMurtrie, Daly City, CA (US); Kin Tso, San Francisco, CA (US); Vanessa Taylor, San Francisco, CA (US); Rajinder Singh, Belmont, CA (US); Rose Yen, San Francisco, CA (US); Jack Maung, Daly City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/793,770

(22) Filed: Oct. 25, 2017

(65) Prior Publication Data
US 2018/0111923 A1    Apr. 26, 2018

Related U.S. Application Data

(60) Provisional application No. 62/413,217, filed on Oct. 26, 2016.

(51) Int. Cl.
*C07D 413/14* (2006.01)
*A61P 29/00* (2006.01)

(52) U.S. Cl.
CPC ............ *C07D 413/14* (2013.01); *A61P 29/00* (2018.01)

(58) Field of Classification Search
None
See application file for complete search history.

(56) References Cited

U.S. PATENT DOCUMENTS 9,982,000 B2 *    5/2018    Kelley ................. C07D 405/14

FOREIGN PATENT DOCUMENTS

| WO | WO 2011/043371 | 4/2011 |
| WO | WO 2016/172560 | 10/2016 |

* cited by examiner

*Primary Examiner* — Kamal A Saeed
(74) *Attorney, Agent, or Firm* — Travis Young; Klarquist Sparkman, LLP

(57) ABSTRACT

Disclosed embodiments concern interleukin receptor associated kinases (IRAK) inhibitors, such as oxazole compounds, and compositions comprising such inhibitors. Also disclosed are methods of making and using the compounds and compositions. The disclosed compounds and/or compositions may be used to treat or prevent an IRAK-associated disease or condition.

21 Claims, No Drawings

IRAK INHIBITORS AND METHOD FOR MAKING AND USING

CROSS REFERENCE TO RELATED APPLICATION

This application claims the benefit of the earlier filing date of U.S. provisional patent application No. 62/413,217, filed Oct. 26, 2016, which is incorporated herein by reference in its entirety.

FIELD

This disclosure concerns interleukin receptor-associated kinase (IRAK) inhibitors, such as oxazole compounds, and embodiments of methods for making and using such compounds for treating diseases and conditions related to IRAK.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Certain disclosed embodiments concern compounds having a formula 1

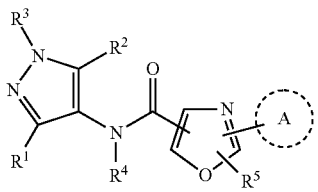

or a salt thereof. A person of ordinary skill in the art will appreciate that compounds within formula 1 also can be solvates, hydrates and/or prodrugs thereof. With reference to formula 1, at least one of $R^1$ and $R^2$ is aromatic, and the remaining $R^1$ or $R^2$ is H, alkyl, haloalkyl, nitro, cyano, amide, amino, hydroxyl, carboxyl, carboxyl ester, or acyl. For particular embodiments, one of $R^1$ and $R^2$ is a nitrogen-containing heteroaryl, such as a 6-membered, nitrogen-containing heteroaryl, particularly pyridinyl, pyrimidinyl or pyrazinyl, such as pyrimidin-2-yl, pyrimidin-4-yl, pyrazine-2-yl, 6-(difluoromethyl)pyridin-2-yl, 3-fluoro-6-(trifluoromethyl)pyridin-2-yl, 3,6-difluoropyridin-2-yl, or 3,5-difluoropyridin-2-yl, and the other of $R^1$ and $R^2$ is H or $C_{1-6}$ alkyl. $R^3$ is H, aliphatic, heteroaliphatic, heterocyclyl, amide, aromatic, or araliphatic. In particular embodiments, $R^3$ is H, alkyl, cycloalkyl, heteroaliphatic, or heterocycloaliphatic, and even more particularly $R^3$ is $C_{1-6}$alkyl, tetrahydropyran, unsubstituted heteroaliphatic, heteroaliphatic substituted with halogen, unsubstituted cyclobutyl, cyclobutyl substituted with alkoxy, unsubstituted cyclohexyl, or cyclohexyl substituted with —OH, alkoxy or heterocycloaliphatic. Exemplary species of disclosed compounds include those having $R^3$ selected from methyl, 4-ethoxycyclohexyl, 4-morpholinocyclobutyl, 3-ethoxycyclobutyl, 4-hydroxycyclohexyl, 3-hydroxycyclobutyl, 4-(4-methylpiperazin-1-yl) cyclohexyl, 3-morpholinocyclohexyl or (2,6-dimethylmorpholino) cyclohexyl. $R^4$ is H, aliphatic, heteroaliphatic, or one of $R^1$ or $R^2$ together with $R^4$, and together with the atoms to which they are attached, form a heterocyclic ring. In particular embodiments, $R^4$ is H or $C_{1-6}$ alkyl, typically H. $R^5$ is H or aliphatic, more typically H, $C_{1-6}$ alkyl or $C_{1-6}$ haloalkyl. Ring A generally is heteroaryl, and more typically ring A is a nitrogen-containing heteroaryl, such as pyrazolyl. Ring A may be unsubstituted. Alternatively, ring A may be substituted with from 1 to 4 substituents, such as at least one substituent selected from aliphatic, halogen, alkylphosphate, or alkylphosphonate.

Accordingly, certain disclosed embodiments concern compounds having formula 1 wherein one of $R^1$ and $R^2$ is selected from pyridinyl, pyrimidinyl or pyrazinyl, and the other of $R^1$ and $R^2$ is H; $R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, unsubstituted cyclohexyl, or cyclohexyl substituted with —OH, alkoxy or heterocycloaliphatic; $R^4$ is H; $R^5$ is H; and ring A is pyrazolyl.

Disclosed compounds also may have a formula 2

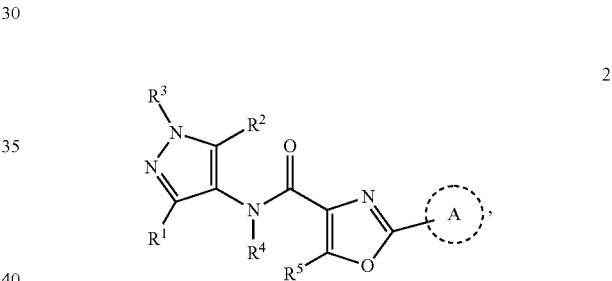

wherein the substituents are as stated for formula 1.

Disclosed compounds also may have a formula 3,

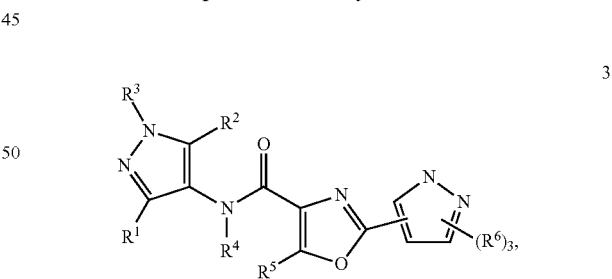

where $R^1$—$R^5$ are as stated for formulas 1 and 2. Each $R^6$ of formula 3 independently is H, aliphatic, cycloaliphatic, heteroaliphatic, halogen, aryl, —O-aliphatic, araliphatic, heterocyclyl, sulfonyl, nitro, —OH, haloalkyl, carboxyl ester, cyano, acyl, amino, alkyl phosphate or alkylphosphonate. More typically, each $R^6$ of formula 3 independently is H, halogen, cycloaliphatic, or alkyl ph—osphate or alkylphosphonate or salts thereof.

Disclosed compounds also may have a formula 4,

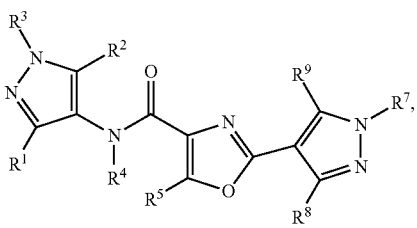

where $R^1$—$R^5$ are as stated for formulas 1-3. Each of $R^7$, $R^8$, and $R^9$ independently is H, aliphatic, cycloaliphatic, heteroaliphatic, halogen, aryl, —O-aliphatic, aralphatic, heterocyclyl, sulfonyl, nitro, —OH, haloalkyl, carboxyl ester, cyano, acyl, amino, alkyl phosphate or alkylphosphonate. $R^7$ typically is H, alkyl, carboxyl ester, acyl, alkyl phosphate, alkyl phosphonate, heterocycloalkyl or aralkyl, such as H, —CH$_2$OP(O)(OH)$_2$ or a salt thereof.

Particular embodiments have $R^8$ and $R^9$ independently selected from H, halogen, alkyl or haloalkyl, and even more particular embodiments have $R^8$ and $R^9$ equal to H, or one of $R^8$ and $R^9$ being H and the other being F.

With reference to compounds of formula 1, one of $R^1$ and $R^2$ is heteroaryl, and the remaining $R^1$ or $R^2$ is H, alkyl, haloalkyl, nitro, cyano, amide, amino, hydroxyl, carboxyl, carboxyl ester, or acyl. $R^3$ is $R^a$, $R^b$, $R^a$ substituted with 1, 2, or 3 $R^b$, $R^a$ substituted with $R^b$ and $R^c$, $R^a$ substituted with $R^c$, —(CR$^a$R$^a$)$_n$—R$^a$, —(CH$_2$)$_n$—R$^a$, —(CR$^a$R$^a$)$_n$—R$^b$, —(CH$_2$)$_n$—R$^b$, —[(CH$_2$)$_m$—O—]$_n$—R$^a$, —[(CH$_2$)$_m$—O—]$_n$-[R$^a$ substituted with 1, 2 or 3 $R^b$], or —(CH$_2$)$_m$—O—(CH$_2$)$_m$—O—R$^a$ wherein each m and n independently are 1, 2 or 3. $R^4$ is $R^a$, —(CR$^a$R$^a$)$_m$—O—R$^a$, —(CH$_2$)$_m$—O—R$^a$, —(CR$^a$R$^a$)$_m$—O—(CR$^a$R$^a$)$_m$—O—R$^a$, —[(CH$_2$)$_m$—O—]$_n$—R$^a$ or —(CH$_2$)$_m$—O—(CH$_2$)$_m$—O—R$^a$ wherein each m and n independently is 1, 2 or 3. $R^5$ is $R^a$ or $R^b$. $R^a$ is independently for each occurrence H, D, C$_{1-6}$alkyl, C$_{1-6}$haloalkyl C$_{3-6}$cycloalkyl, C$_{3-6}$heteroalicyclyl,

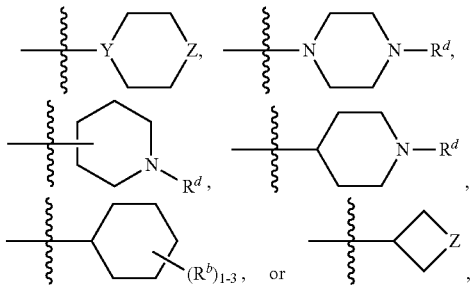

where Y and Z independently are —CH$_2$, —CHR$^b$, O or NR$^d$. $R^c$ is independently for each occurrence C$_{1-6}$alkyl, C$_{3-6}$heteroalicyclyl, C$_{1-6}$alkyl substituted with 1, 2 or 3 R$^e$, C$_{3-6}$cycloalkyl substituted with 1, 2 or 3 R$^e$, or C$_{3-6}$heteroalicyclyl substituted with 1, 2 or 3 R$^e$. $R^d$ is independently for each occurrence —C(O)R$^a$, C$_{1-6}$alkyl optionally substituted with 1, 2 or 3 R$^e$, or two R$^d$ groups together with the nitrogen bound thereto form a C$_{3-6}$heteroalicyclyl moiety optionally substituted with C$_{1-6}$alkyl and optionally interrupted with one or two —O— or —N(R$^g$) wherein R$^g$ is R$^{70}$. And R$^e$ is independently for each occurrence C$_{1-6}$alkyl or —OR$^a$.

Exemplary species of compounds according to the present invention may be selected from N-(1-((1r,4r)-4-ethoxycyclohexyl)-3-(pyrazin-2-yl)-1H-pyrazol-4-yl)-2-(1H-pyrazol-4-yl)oxazole-4-carboxamide; N-(1-((1r,4r)-4-morpholinocyclohexyl)-3-(pyrimidin-2-yl)-1H-pyrazol-4-yl)-2-(1H-pyrazol-4-yl)oxazole-4-carboxamide; N-(1-((1r,4r)-4-ethoxycyclohexyl)-3-(pyrimidin-2-yl)-1H-pyrazol-4-yl)-2-(1H-pyrazol-4-yl)oxazole-4-carboxamide; N-(3-(6-(difluoromethyl)pyridin-2-yl)-1-((1r,4r)-4-morpholinocyclohexyl)-1H-pyrazol-4-yl)-2-(1H-pyrazol-4-yl)oxazole-4-carboxamide; N-(3-(6-(difluoromethyl)pyridin-2-yl)-1-((1R,4r)-4-((2R,6S)-2,6-dimethylmorpholino)cyclohexyl)-1H-pyrazol-4-yl)-2-(1H-pyrazol-4-yl)oxazole-4-carboxamide; N-(1-((1r,4r)-4-ethoxycyclohexyl)-3-(pyrimidin-4-yl)-1H-pyrazol-4-yl)-2-(1H-pyrazol-4-yl)oxazole-4-carboxamide; N-(3-(3-fluoro-6-(trifluoromethyl)pyridin-2-yl)-1-((1r,4r)-4-morpholinocyclohexyl)-1H-pyrazol-4-yl)-2-(1H-pyrazol-4-yl)oxazole-4-carboxamide; sodium (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl) methyl phosphate; N-(3-(3,6-difluoropyridin-2-yl)-1-((1r,4r)-4-ethoxycyclohexyl)-1H-pyrazol-4-yl)-2-(1H-pyrazol-4-yl)oxazole-4-carboxamide; N-(3-(3,6-difluoropyridin-2-yl)-1-((1s,3s)-3-ethoxycyclobutyl)-1H-pyrazol-4-yl)-2-(1H-pyrazol-4-yl)oxazole-4-carboxamide; N-(3-(3,6-difluoropyridin-2-yl)-1-((1r,4r)-4-hydroxycyclohexyl)-1H-pyrazol-4-yl)-2-(1H-pyrazol-4-yl)oxazole-4-carboxamide; (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl)methyl dihydrogen phosphate; N-(3-(3,5-difluoropyridin-2-yl)-1-((1r,4r)-4-ethoxycyclohexyl)-1H-pyrazol-4-yl)-2-(1H-pyrazol-4-yl)oxazole-4-carboxamide; N-(5-(3,6-difluoropyridin-2-yl)-1-((1r,4R)-4-ethoxycyclohexyl)-1H-pyrazol-4-yl)-2-(1H-pyrazol-4-yl)oxazole-4-carboxamide; 2-(1H-pyrazol-4-yl)-N-(3-(pyridin-2-yl)-1-(2-(2,2,2-trifluoroethoxy)ethyl)-1H-pyrazol-4-yl)oxazole-4-carboxamide; di-tert-butyl ((4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl) phosphate; (4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl dihydrogen phosphate; sodium (4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl) methyl phosphate; 2-(1-(cyclopropylmethyl)-1H-pyrazol-4-yl)-N-(1-methyl-3-(pyridin-2-yl)-1H-pyrazol-4-yl)oxazole-4-carboxamide; 2-(1H-pyrazol-4-yl)-N-(3-(pyridin-2-yl)-1-(tetrahydro-2H-pyran-4-yl)-1H-pyrazol-4-yl)oxazole-4-carboxamide; N-(1-(2-ethoxyethyl)-3-(pyridin-2-yl)-1H-pyrazol-4-yl)-2-(1H-pyrazol-4-yl)oxazole-4-carboxamide; N-(1-((1s,3s)-3-ethoxycyclobutyl)-3-(pyridin-2-yl)-1H-pyrazol-4-yl)-2-(1H-pyrazol-4-yl)oxazole-4-carboxamide; N-(1-cyclobutyl-3-(pyridin-2-yl)-1H-pyrazol-4-yl)-2-(1H-pyrazol-4-yl)oxazole-4-carboxamide; N-(1-(2-(2-methoxyethoxy)ethyl)-3-(pyridin-2-yl)-1H-pyrazol-4-yl)-2-(1H-pyrazol-4-yl)oxazole-4-carboxamide; 2-(1H-pyrazol-3-yl)-N-(3-(pyridin-2-yl)-1-(2-(2,2,2-trifluoroethoxy)ethyl)-1H-pyrazol-4-yl)oxazole-4-carboxamide; N-(1-(2-(2,2-difluoroethoxy)ethyl)-3-(pyridin-2-yl)-1H-pyrazol-4-yl)-2-(1H-pyrazol-4-yl)oxazole-4-carboxamide; N-(3-(3,6-difluoropyridin-2-yl)-1-((1r,3r)-3-ethoxycyclobutyl)-1H-pyrazol-4-yl)-2-(1H-pyrazol-4-yl)oxazole-4-carboxamide; N-(1-((1r,4r)-4-hydroxycyclohexyl)-3-(pyrazin-2-yl)-1H-pyrazol-4-yl)-2-(1H-pyrazol-4-yl)oxazole-4-carboxamide; N-(1-((1r,4r)-4-ethoxycyclohexyl)-3-(3,5,6-trifluoropyridin-2-yl)-1H-pyrazol-4-yl)-2-(1H-pyrazol-4-yl)oxazole-4- carboxamide; N-(3-(4,6-difluoropyridin-2-yl)-1-((1r,4r)-4-ethoxycyclohexyl)-1H-pyrazol-4-yl)-2-(1H-pyrazol-4-yl)oxazole-4-carboxamide; N-(1-((1r,4r)-4-morpholinocyclohexyl)-3-(pyrazin-2-yl)-1H-pyrazol-4-yl)-2-(1H-pyrazol-4-yl)oxazole-4-carboxamide; N-(1-((1r,4r)-4-ethoxycyclohexyl)-3-(3-fluoro-6-(trifluoromethyl)pyridin-2-yl)-1H-pyrazol-4-yl)-2-(1H-pyrazol-4-yl)oxazole-4-carboxamide; N-(1-((1r,4r)-4-ethoxycyclohexyl)-3-(pyrazin-2-yl)-1H-pyrazol-4-yl)-2-(5-fluoro-1H-pyrazol-4-yl)oxazole-4-carboxamide; N-(1-((1r,3r)-3-morpholinocyclobutyl)-3-(pyrazin-2-yl)-1H-pyrazol-4-yl)-2-(1H-pyrazol-4-yl)oxazole-4-carboxamide; N-(1-((1s,3s)-3-morpholinocyclobutyl)-3-(pyrazin-2-yl)-1H-pyrazol-4-yl)-2-(1H-pyrazol-4-yl)oxazole-4-carboxamide; 2-(3-fluoro-1H-pyrazol-4-yl)-N-(1-((1r,4r)-4-morpholinocyclohexyl)-3-(pyrazin-2-yl)-1H-pyrazol-4-yl)oxazole-4-carboxamide formic acid salt; N-(3-(3,6-difluoropyridin-2-yl)-1-((1s,4s)-4-(4-methylpiperazin-1-yl)cyclohexyl)-1H-pyrazol-4-yl)-2-(1H-pyrazol-4-yl)oxazole-4-carboxamide; N-(3-(3,6-difluoropyridin-2-yl)-1-((1r,4r)-4-morpholinocyclohexyl)-1H-pyrazol-4-yl)-2-(1H-pyrazol-4-yl)oxazole-4-carboxamide; N-(1-((1 s,3s)-3-hydroxycyclobutyl)-3-(pyrazin-2-yl)-1H-pyrazol-4-yl)-2-(1H-pyrazol-4-yl)oxazole-4-carboxamide; and 2-(3-fluoro-1H-pyrazol-4-yl)-N-(1-((1r,4r)-4-morpholinocyclohexyl)-3-(pyrazin-2-yl)-1H-pyrazol-4-yl)oxazole-4-carboxamide.

For certain embodiments, the compound is not 2-(1-(cyclopropylmethyl)-1H-pyrazol-4-yl)-N-(1-methyl-3-(pyridin-2-yl)-1H-pyrazol-4-yl)oxazole-4-carboxamide; 2-(1H-pyrazol-4-yl)-N-(3-(pyridin-2-yl)-1-(tetrahydro-2H-pyran-4-yl)-1H-pyrazol-4-yl)oxazole-4-carboxamide; N-(1-(2-ethoxyethyl)-3-(pyridin-2-yl)-1H-pyrazol-4-yl)-2-(1H-pyrazol-4-yl)oxazole-4-carboxamide; N-(1-((1s,3s)-3-ethoxycyclobutyl)-3-(pyridin-2-yl)-1H-pyrazol-4-yl)-2-(1H-pyrazol-4-yl)oxazole-4-carboxamide; N-(1-cyclobutyl-3-(pyridin-2-yl)-1H-pyrazol-4-yl)-2-(1H-pyrazol-4-yl)oxazole-4-carboxamide; N-(1-(2-(2-methoxyethoxy)ethyl)-3-(pyridin-2-yl)-1H-pyrazol-4-yl)-2-(1H-pyrazol-4-yl)oxazole-4-carboxamide; N-(1-(2-(2,2-difluoroethoxy)ethyl)-3-(pyridin-2-yl)-1H-pyrazol-4-yl)-2-(1H-pyrazol-4-yl)oxazole-4-carboxamide; N-(1-(2-(2,2-difluoroethoxy)ethyl)-3-(pyridin-2-yl)-1H-pyrazol-4-yl)-2-(1H-pyrazol-4-yl)oxazole-4-carboxamide; N-(3-carbamoyl-1-(tetrahydro-2H-pyran-4-yl)-1H-pyrazol-4-yl)-2-(1H-pyrazol-4-yl)oxazole-4-carboxamide; or 2-(1H-pyrazol-3-yl)-N-(3-(pyridin-2-yl)-1-(2-(2,2-trifluoroethoxy)ethyl)-1H-pyrazol-4-yl)oxazole-4-carboxamide.

Compounds according to the present disclosure also may be formulated as compositions comprising one or more compounds according to any of formulas 1-12, and a pharmaceutically acceptable excipient. Such compositions also may include an additional therapeutic agent.

Methods for making and using such compounds and compositions also are disclosed. For example, one disclosed embodiment of a method for using compounds within formulas 1-12 comprises administering to a subject in need thereof an effective amount of a compound, two or more compounds, or a composition comprising at least one compound, according to any or all of formulas 1-12. The method may be particularly suitable for treating a disease or condition for which an IRAK inhibitor is indicated, including an IRAK1, IRAK2, IRAK3 and/or IRAK4 inhibitor. The disease may be an auto-immune disease, an inflammatory disorder, a cardiovascular disease, a neurodegenerative disorder, an allergic disorder, a multi-organ failure, a kidney disease, a platelet aggregation malady, cancer, transplantation, sperm motility, erythrocyte deficiency, graft rejection, lung injury, respiratory disease, ischemic condition, bacterial infection, viral infection, immune regulatory disorder, or a combination thereof.

Disclosed embodiments of a method for using compounds according to formulas 1-12 also include inhibiting an IRAK protein by contacting the IRAK protein with an effective amount of a compound or compounds, or composition comprising a compound or compounds, according to any or all of formulas 1-12 wherein the compound has an $EC_{50}$ of from greater than 0 to 5 µM, typically from 0 to 1 µM, and with many disclosed compounds having an $EC_{50}$ substantially lower than 1 µM. The IRAK protein may be in a subject, or the method may comprise contacting the IRAK protein in vitro.

Additional features of disclosed embodiments of the present invention are provided by U.S. patent application Ser. No. 15/136,508, which is incorporated herein by reference.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four.

For example, in the structure on the left-hand side of the schematic below there are nine hydrogen atoms implied. The nine hydrogen atoms are depicted in the right-hand structure.

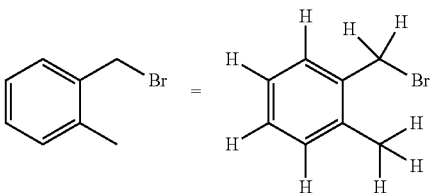

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

If a group R is depicted as "floating" on a ring system, as for example in the group:

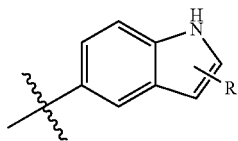

then, unless otherwise defined, a substituent R can reside on any atom of the fused bicyclic ring system, excluding the atom carrying the bond with the "〰" symbol, so long as a stable structure is formed. In the example depicted, the R group can reside on an atom in either the 5-membered or the 6-membered ring of the indolyl ring system.

When there are more than one such depicted "floating" groups, as for example in the formulae:

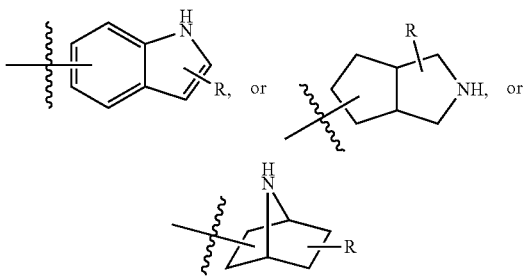

where there are two groups, namely, the R and the bond indicating attachment to a parent structure; then, unless otherwise defined, the "floating" groups can reside on any atoms of the ring system, again assuming each replaces a depicted, implied, or expressly defined hydrogen on the ring system and a chemically stable compound would be formed by such an arrangement.

When a group R is depicted as existing on a ring system containing saturated carbons, as for example in the formula:

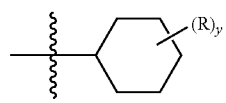

where, in this example, y can be more than one, assuming each replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can form a ring, thus creating a spirocyclic ring (a "spirocyclyl" group) structure. For example, shown below two Rs can form a piperidine ring in a spirocyclic arrangement with the cyclohexane, as

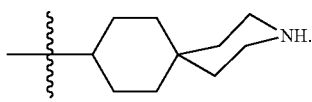

As used herein, the term "substituted" refers to all subsequent modifiers in a term, for example in the term "substituted arylC$_{1-8}$alkyl," substitution may occur on the "C$_{1-8}$alkyl" portion, the "aryl" portion or both portions of the arylC$_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" or a "pyrazolyl" moiety may be unsubstituted or substituted, but an "unsubstituted alkyl" or an "unsubstituted pyrazolyl" is not substituted.

"Substituents" or "substituent groups" for substituting for one or more hydrogen atoms on saturated carbon atoms in the specified group or moiety are, unless otherwise specified, —R$^{60}$, halo, =O, —OR$^{70}$, —SR$^{70}$, —N(R$^{80}$)$_2$, haloalkyl, perhaloalkyl, —CN, —NO$_2$, =N$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —P(O)(O$^-$)$_2$(M$^+$)$_2$, —P(O)(O$^-$)$_2$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)N(R$^{80}$)$_2$, —C(NR$^{70}$)(R$^{80}$)$_2$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$ is C$_{1-10}$ aliphatic, heteroaliphatic, or cycloaliphatic, typically C$_{1-6}$aliphatic, more typically C$_{1-6}$alkyl, where R$^{60}$ optionally may be substituted; each R$^{70}$ is independently for each occurrence hydrogen or R$^{60}$; each R$^{80}$ is independently for each occurrence R$^{70}$ or alternatively, two R$^{80}$ groups, taken together with the nitrogen atom to which they are bonded, form a 3- to 7-membered heterocycloaliphatic, which optionally includes from 1 to 4 of the same or different additional heteroatoms selected from O, N and S, of which N optionally has R$^{70}$ substitution, such as H or C$_1$-C$_3$alkyl substitution; and each M$^+$ is a counter ion with a net single positive charge. Each M$^+$ is independently for each occurrence, for example, an alkali metal ion, such as K$^+$, Na$^+$, Li$^+$; an ammonium ion, such as $^+$N(R$^{60}$)$_4$; a protonated amino acid ion, such as a lysine ion, or an arginine ion; or an alkaline metal earth ion, such as [Ca$^{2+}$]$_{0.5}$, [Mg$^{2+}$]$_{0.5}$, or [Ba$^{2+}$]$_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —N($R^{80}$)$_2$ includes —NH$_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, =O, =N$R^{70}$, =N—O$R^{70}$, =N$_2$ or =S.

Substituent groups for replacing hydrogen atoms on unsaturated carbon atoms in groups containing unsaturated carbons are, unless otherwise specified, —$R^{60}$, halo, —O$^-$M$^+$, —O$R^{70}$, —S$R^{70}$, —S$^-$M$^+$, —N($R^{80}$)$_2$, haloalkyl, perhaloalkyl, —CN, —OCN, —SCN, —NO, —NO$_2$, —N$_3$, —SO$_2R^{70}$, —SO$_3^-$M$^+$, —SO$_3R^{70}$, —OSO$_2R^{70}$, —OSO$_3^-$M$^+$, —OSO$_3R^{70}$, —PO$_3^{-2}$(M+)$_2$, —PO$_3^{-2}$M$^{2+}$, —P(O)(O$R^{70}$)O$^-$M$^+$, —P(O)(O$R^{70}$)$_2$, —C(O)$R^{70}$, —C(S)$R^{70}$, —C(N$R^{70}$)$R^{70}$, —CO$_2^-$M$^+$, —CO$_2R^{70}$, —C(S)O$R^{70}$, —C(O)NR$^{80}R^{80}$, —C(N$R^{70}$)N($R^{80}$)$_2$, —OC(O)$R^{70}$, —OC(S)$R^{70}$, —OCO$_2^-$M$^+$, —OCO$_2R^{70}$, —OC(S)O$R^{70}$, —N$R^{70}$C(O)$R^{70}$, —N$R^{70}$C(S)$R^{70}$, —N$R^{70}$CO$_2^-$M$^+$, —N$R^{70}$CO$_2R^{70}$, —N$R^{70}$C(S)O$R^{70}$, —N$R^{70}$C(O)N($R^{80}$)$_2$, —N$R^{70}$C(N$R^{70}$)$R^{70}$ and —N$R^{70}$C(N$R^{70}$)N($R^{80}$)$_2$, where $R^{60}$, $R^{70}$, $R^{80}$ and M$^+$ are as previously defined, provided that in case of substituted alkene or alkyne, the substituents are not —O$^-$M$^+$, —O$R^{70}$, —S$R^{70}$, or —S$^-$M$^+$.

Substituent groups for replacing hydrogen atoms on nitrogen atoms in groups containing such nitrogen atoms are, unless otherwise specified, —$R^{60}$, —O$^-$M$^+$, —O$R^{70}$, —S$R^{70}$, —S$^-$M$^+$, —N($R^{80}$)$_2$, haloalkyl, perhaloalkyl, —CN, —NO, —NO$_2$, —S(O)$_2R^{70}$, —SO$_3^-$M+, —SO$_3R^{70}$, —OS(O)$_2R^{70}$, —OSO$_3^-$M+, —OSO$_3R^{70}$, —PO$_3^{2-}$(M$^+$)$_2$, —PO$_3^{2-}$M$^{2+}$, —P(O)(O$R^{70}$)O$^-$M$^+$, —P(O)(O$R^{70}$)(O$R^{70}$), —C(O)$R^{70}$, —C(S)$R^{70}$, —C(N$R^{70}$)$R^{70}$, —CO$_2R^{70}$, —C(S)O$R^{70}$, —C(O)NR$^{80}R^{80}$, —C(N$R^{70}$)NR$^{80}R^{80}$, —OC(O)$R^{70}$, —OC(S)$R^{70}$, —OCO$_2R^{70}$, —OC(S)O$R^{70}$, —N$R^{70}$C(O)$R^{70}$, —N$R^{70}$C(S)$R^{70}$, —N$R^{70}$CO$_2R^{70}$, —N$R^{70}$C(S)O$R^{70}$, —N$R^{70}$C(O)N($R^{80}$)$_2$, —N$R^{70}$C(N$R^{70}$)$R^{70}$ and —N$R^{70}$C(N$R^{70}$)N($R^{80}$)$_2$, where $R^{60}$, $R^{70}$, $R^{80}$ and M$^+$ are as previously defined.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, heterocyclic or aromatic. Exemplary acyl moieties include, but are not limited to, —C(O)H, —C(O)alkyl, —C(O)C$_1$-C$_6$alkyl, —C(O)C$_1$-C$_6$haloalkyl-C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms (C$_{1-25}$); for example, from one to fifteen (C$_{1-15}$), from one to ten (C$_{1-10}$) from one to six (C$_{1-6}$), or from one to four carbon atoms (C$_{1-4}$) for an acyclic aliphatic group or moiety, or from three to fifteen (C$_{3-15}$) from three to ten (C$_{3-10}$), from three to six (C$_{3-6}$), or from three to four (C$_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

"Lower aliphatic" refers to an aliphatic group containing from one to ten carbon atoms (C$_{1-10}$), such as from one to six (C$_{1-6}$), or from one to four (C$_{1-4}$) carbon atoms; or from three to ten (C$_3$10), such as from three to six (C$_3$ 6) carbon atoms for a lower cycloaliphatic group.

"Alkoxy" refers to the group —OR, where R is a substituted or unsubstituted alkyl or a substituted or unsubstituted cycloalkyl group. In certain examples R is a C$_{1-6}$ alkyl group or a C$_{3-6}$cycloalkyl group. Methoxy (—OCH$_3$) and ethoxy (—OCH$_2$CH$_3$) are exemplary alkoxy groups.

In a substituted alkoxy, R is substituted alkyl or substituted cycloalkyl, examples of which in the presently disclosed compounds include haloalkoxy groups, such as —OCF$_2$H.

"Alkoxyalkyl" refers to the group -alkyl-OR, where R is a substituted or unsubstituted alkyl group or a substituted or unsubstituted cycloalkyl; —CH$_2$CH$_2$—O—CH$_2$CH$_3$ is an exemplary alkoxyalkyl group.

"Alkyl" refers to a saturated aliphatic hydrocarbyl group having from 1 to at least 25 (C$_{1-25}$) carbon atoms, more typically 1 to 10 (C$_{1-10}$) carbon atoms such as 1 to 6 (C$_{1-6}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —(CH$_2$)$_{2-5}$-ring optionally interrupted by one or two heteroatom groups, such as —O— or —N(R$^g$) such as in the groups

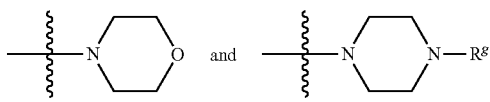

wherein $R^g$ is $R^{70}$, —C(O)$R^{70}$, —C(O)O$R^{60}$ or —C(O)N$(R^{80})_2$.

"Amide" or "carboxamide" refers to the group —N(R)acyl, or —C(O)amino, where R is hydrogen, heteroaliphatic or aliphatic, such as alkyl, particularly $C_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

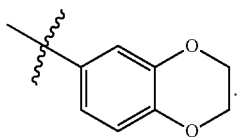 [SMILES: *c1ccc2c(c1)OCCO2]

However, in certain examples, context or express disclosure may indicate that the point of attachment is through a non-aromatic portion of the condensed ring system. For example,

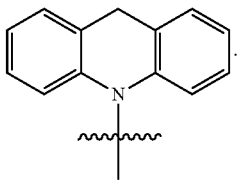 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl" or "carboxylate" refers to —$CO_2H$, —C(O)$O^-$ or salts thereof.

"Carboxyl ester" or "carboxy ester" refers to the group —C(O)OR, where R is aliphatic, heteroaliphatic, cyclic, heterocyclic, and aromatic, including both aryl and heteroaryl.

"Cyano" refers to the group —CN.

"Cycloaliphatic" refers to a cyclic aliphatic group having a single ring (e.g., cyclohexyl), or multiple rings, such as in a fused, bridged or spirocyclic system, at least one of which is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —$CH_2F$, —$CHF_2$ and —$CF_3$.

"Heteroaliphatic" refers to an aliphatic compound or group having at least one heteroatom and at least one carbon atom, i.e., one or more carbon atoms from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety of, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings which are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —O$^-$M$^+$, where each M$^+$ is a positively charged counterion. By way of example, M$^+$ may be an alkali ion, such as K$^+$, Na$^+$, Li$^+$; an ammonium ion, such as $^+$N(R")$_4$ where R" is H, aliphatic, heterocyclyl or aryl; or an alkaline earth ion, such as [Ca$^{2+}$]$_{0.5}$, [Mg$^{2+}$]$_{0.5}$, or [Ba$^{2+}$]$_{0.5}$. Phosphonooxyalkyl refers to the group -alkyl-phosphate, such as, for example, —CH$_2$OP(O)(OH)$_2$, or a salt thereof, such as —CH$_2$OP(O)(O$^-$Na$^+$)$_2$, and (((dialkoxyphosphoryl)oxy)alkyl) refers to the dialkyl ester of a phosphonooxyalkyl group, such as, for example, —CH$_2$OP(O)(O-tert-butyl)$_2$.

"Phosphonate" refers to the group —P(O)(OR')$_2$, where each —OR' independently is —OH; —O-aliphatic such as —O-alkyl or —O-cycloalkyl; —O-aromatic, including both —O-aryl and —O-heteroaryl; or —O-aralkyl; or —OR' is —O$^-$M$^+$, where each M$^+$ is a positively charged counterion. By way of example, M$^+$ may be an alkali metal ion, such as K$^+$, Na$^+$, Li$^+$; an ammonium ion, such as $^+$N(R")$_4$ where R" is H, aliphatic, heterocyclyl or aryl; or an alkaline earth metal ion, such as [Ca$^{2+}$]$_{0.5}$, [Mg$^{2+}$]$_{0.5}$, or [Ba$^{2+}$]$_{0.5}$. Phosphonoalkyl refers to the group -alkyl-phosphonate, such as, for example, —CH$_2$P(O)(OH)$_2$, or —CH$_2$P(O)(O$^-$Na$^+$)$_2$, and ((dialkoxyphosphoryl)alkyl) refers to the dialkyl ester of a phosphonoalkyl group, such as, for example, —CH$_2$P(O)(O-tert-butyl)$_2$.

"Patient" or "Subject" refers to mammals and other animals, particularly humans. Thus disclosed methods are applicable to both human therapy and veterinary applications.

"Pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition.

Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, Pa., 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

"Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzenesulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compounds may be a formate, trifluoroactate, hydrochloride or sodium salt.

"Effective amount" with respect to a compound or composition refer to an amount of the compound or composition sufficient to achieve a particular desired result, such as to inhibit a protein or enzyme, particularly an IRAK kinase; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the age of the patient to be treated, and the like.

"Prodrug" refers to compounds that are transformed in vivo to yield a biologically active compound, particularly the parent compound, for example, by hydrolysis in the gut or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R' is H or $C_{1-6}$alkyl.

Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Some examples of solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —N(R)sulfonyl, where R is H, aliphatic, heteroaliphatic, cyclic, heterocyclic, including aromatic, both aryl and heteroaryl.

"Sulfanyl" refers to the group or —SH, —S-aliphatic, —S-heteroaliphatic, —S-cyclic, —S-heterocyclyl, including —S-aromatic, both-S-aryl and —S-heteroaryl.

"Sulfinyl" refers to the group or moiety —S(O)H, —S(O)aliphatic, —S(O)heteroaliphatic, —S(O)cyclic, —S(O)heterocyclyl, including aromatic, both —S(O)aryl and —S(O)heteroaryl.

"Sulfonyl" refers to the group: —$SO_2$H, —$SO_2$aliphatic, —$SO_2$heteroaliphatic, —$SO_2$cyclic, —$SO_2$heterocyclyl, including aromatic sulfonyls including both —$SO_2$aryl and —$SO_2$heteroaryl.

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substituents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the pyrazolyl and pyridinyl rings, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$.

II. IRAK-active Compounds and Compositions Comprising IRAK-active Compounds

A. Oxazoles

Disclosed herein are oxazole compounds, methods of making the compounds, and methods of using the compounds. In one embodiment the disclosed compounds are tyrosine kinase inhibitors. In a particular embodiment the compounds useful in blocking one or more cytokine signaling pathways, such as the IL-17 signaling pathway. For certain embodiments, the oxazole compounds are useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3, IRAK4, or a combination thereof.

Exemplary oxazole compounds within the scope of the present invention have a general formula 1

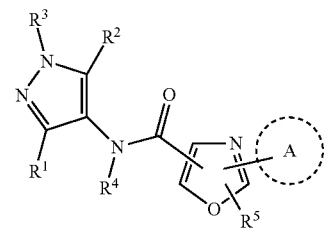

1 and/or salts, prodrugs, N-oxides or solvates thereof. With reference to formula 1, at least one of $R^1$ and $R^2$ is aromatic, such as heteroaryl. In some embodiments, one of $R^1$ and $R^2$ is heteroaryl, and may be a nitrogen-containing heteroaryl, such as pyridine, pyrimidine or pyrazine, and the other of $R^1$ and $R^2$ is H, alkyl, haloalkyl, nitro, cyano, amide, amino, hydroxyl, carboxyl, carboxyl ester, or acyl. In certain disclosed examples, one of $R^1$ and $R^2$ is H. In some examples, one of $R^1$ and $R^2$ is a 6-membered nitrogen-containing heteroaryl, and the other is H. In certain embodiments, $R^1$ is a 6-membered nitrogen-containing heteroaryl, and $R^2$ is H.

$R^3$ is H; aliphatic, including alkyl, alkenyl, alkynyl, cycloalkyl, and cycloalkenyl; heteroaliphatic; aromatic, including both aryl and heteroaryl; heterocyclyl, such as heterocycloaliphatic; amide; aryl; or araliphatic. In some embodiments of formula 1, $R^3$ is H, alkyl, cycloaliphatic, typically cycloalkyl, such as cyclopropyl, cyclobutyl, cyclopentyl or cyclohexyl, heteroaliphatic, or heterocycloaliphatic.

In some embodiments, $R^3$ is cyclohexyl, optionally substituted with OH, alkoxy or heterocycloaliphatic.

In other embodiments, $R^3$ is cyclobutyl, optionally substituted with OH, alkoxy or heterocycloaliphatic.

In particular embodiments, one of $R^1$ and $R^2$ is a 6-membered, nitrogen-containing heteroaryl selected from pyridinyl, pyrimidinyl or pyrazinyl, the other of $R^1$ and $R^2$ is H, and $R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, or cyclohexyl substituted with —OH, alkoxy or heterocycloaliphatic.

$R^4$ is H, aliphatic, such as alkyl, including $C_{1-6}$ alkyl, or heteroaliphatic. Alternatively, one of $R^1$ or $R^2$ together with $R^4$, and together with the atoms to which they are attached, form a ring, such as a heterocyclyl ring, having 3, 4, 5, 6, 7, 8 or more ring atoms, particularly 5, 6, or 7 ring atoms.

In particular embodiments, one of $R^1$ and $R^2$ is a 6-membered, nitrogen-containing heteroaryl selected from pyridinyl, pyrimidinyl or pyrazinyl, the other of $R^1$ and $R^2$ is H; $R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, or cyclohexyl substituted with —OH, alkoxy or heterocycloaliphatic; and $R^4$ is H.

$R^5$ is H; aliphatic, including alkyl, alkenyl, alkynyl, or haloaliphatic. $R^5$ may be H, alkyl, such as $C_{1-6}$alkyl, or haloalkyl, such as fluoroalkyl. And in some embodiments $R^5$ is H.

In particular embodiments, one of $R^1$ and $R^2$ is a 6-membered, nitrogen-containing heteroaryl selected from pyridinyl, pyrimidinyl or pyrazinyl, the other of $R^1$ and $R^2$ is H; $R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, or cyclohexyl substituted with —OH, alkoxy or heterocycloaliphatic; $R^4$ is H; and $R^5$ is H.

Ring A is heterocyclic, such as heteroaryl or heterocycloaliphatic. In some embodiments, ring A is heteroaryl, and may be a nitrogen-containing heteroaryl, such as a 5-membered nitrogen-containing heteroaryl. In any of the above embodiments, ring A may be pyrazolyl.

In some embodiments, ring A is unsubstituted. In other embodiments, ring A is substituted, and may be substituted with from one to the number of possible substituents on the particular system in question, such as from 1 to 2, 3 or 4 substituents. Possible substituents for ring A include, but at not limited to, halogen, including F, Cl, Br, or I, aliphatic, including alkyl, alkenyl, and alkynyl, alkylphosphate, alkylphosphonate, or salts thereof.

In particular embodiments, one of $R^1$ and $R^2$ is a 6-membered, nitrogen-containing heteroaryl selected from pyridinyl, pyrimidinyl or pyrazinyl, the other of $R^1$ and $R^2$ is H; $R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, or cyclohexyl substituted with —OH, alkoxy or heterocycloaliphatic; $R^4$ is H; $R^5$ is H; and ring A is pyrazolyl, optionally substituted with halogen, aliphatic, including alkyl, alkenyl, and alkynyl, alkylphosphate, alkylphosphonate, and/or salts thereof.

In certain embodiments, $R^3$ is $R^a$, $R^b$, $R^a$ substituted with 1, 2, or 3 $R^b$, $R^a$ substituted with $R^b$ and $R^c$, $R^a$ substituted with $R^c$, —$(CR^aR^a)_n$—$R^a$, —$(CH_2)_n$—$R^a$, —$(CR^aR^a)_n$—$R^b$, —$(CH_2)_n$—$R^b$, —$[(CH_2)_m$—O—$]_n$—$R^a$, —$[(CH_2)_m$—O—$]_n$-[$R^a$ substituted with 1, 2 or 3 $R^b$], or —$(CH_2)_m$—O—$(CH_2)_m$—O—$R^a$, wherein each m and n independently are 1, 2 or 3;

In some embodiments, $R^4$ is $R^a$, —$(CR^aR^a)_m$—O—$R^a$, —$(CH_2)_m$—O—$R^a$, —$(CR^aR^a)_m$—O—$(CR^aR^a)_m$—O—$R^a$, —$[(CH_2)_m$—O—$]_n$—$R^a$ or —$(CH_2)_m$—O—$(CH_2)_m$—O—$R^a$ wherein each m and n independently are 1, 2 or 3;

$R^5$ is $R^a$ or Rb;

$R^a$ is independently for each occurrence H, D, $C_{1-6}$alkyl, $C_{1-6}$haloalkyl $C_{3-6}$cycloalkyl, $C_{3-6}$heteroalicyclyl,

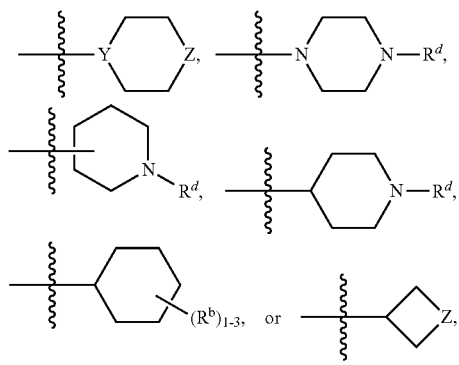

where Y and Z independently are —$CH_2$, —$CHR^b$, O or $NR^d$.

$R^b$ is independently for each occurrence —OH, —$CF_3$, —$OR^c$, —$NR^dR^d$ or halogen;

$R^c$ is independently for each occurrence $C_{1-6}$alkyl, $C_{3-6}$heteroalicyclyl, $C_{1-6}$alkyl substituted with 1, 2 or 3 $R^e$, or $C_{3-6}$heteroalicyclyl substituted with 1, 2 or 3 $R^e$;

$R^d$ is independently for each occurrence —C(O)$R^a$, $C_{1-6}$alkyl optionally substituted with 1, 2 or 3 $R^e$, or two $R^d$ groups together with the nitrogen bound thereto form a $C_{3-6}$heteroalicyclyl moiety optionally substituted with $C_{1-6}$alkyl and optionally interrupted with one or two —O— or —N($R^g$) wherein $R^g$ is $R^{7o}$; and $R^e$ is independently for each occurrence $C_{1-6}$alkyl or —$OR^a$.

With respect to formula 1, $R^1$ may be: 1A) heteroaryl; 1B) nitrogen-containing heteroaryl; 1C) 6-membered nitrogen-containing heteroaryl; 1D) pyridinyl; 1E) pyrimidinyl; 1F) pyrazinyl; 1G) pyridin-2-yl; 1H) pyrimidin-2-yl; 1I) pyrimidin-4-yl; 1J) pyrazin-2-yl; 1K) pyridin-2-yl substituted at least at the 6-position; 1L) pyridin-2-yl substituted at least at the 3-position; 1M) 6-(difluoromethyl)pyridin-2-yl; 1N) 3-fluoro-6-(trifluoromethyl)pyridin-2-yl; 1O) 3,6-difluoropyridin-2-yl; 1P) 3,5-difluoropyridin-2-yl; 1Q) 3,5,6-trifluoropyridin-2-yl; or 1R) 4,6-difluoropyridin-2-yl.

With respect to embodiments where $R^1$ is 1A to 1R, $R^3$ may be, in any combination with 1A to 1R: 2A) aliphatic; 2B) cycloaliphatic; 2C) cycloalkyl; 2E) cycloalkyl substituted with O-alkyl, heterocyclyl, or OH; 2F) cyclohexyl; 2G) cyclobutyl; 2H) cyclohexyl substituted with O—$C_{1-6}$alkyl; 2I) cyclobutyl substituted with O—$C_{1-6}$alkyl; 2J) cyclohexyl substituted with heteroalicyclyl; 2K) cyclohexyl substituted with OH; 2L) cyclobutyl substituted with OH; 2M) cyclobutyl substituted with heteroalicyclyl; 2M) (1r,4r)-4-morpholinocyclohexyl; 2N) (1s,4s)-4-morpholinocyclohexyl; 2O) (1r,3r)-3-ethoxycyclobutyl; 2P) (1s,3s)-3-ethoxycyclobutyl; 2Q) (1r,4r)-4-ethoxycyclohexyl; 2S) (1s,4s)-4-ethoxycyclohexyl; 2T) (1r,4r)-4-hydroxycyclohexyl; 2U) (1s,4s)-4-hydroxycyclohexyl; 2V) ((1R,4r)-4-(2R,6S)-2,6-dimethylmorpholino) cyclohexyl; 2W) (1r,3r)-3-morpholinocyclobutyl; 2×) (1s,3s)-3-morpholinocyclobutyl; 2Y) (1s,4s)-4-(4-methylpiperazin-1-yl)cyclohexyl; 2Z) (1r,4r)-4-(4-methylpiperazin-1-yl)cyclohexyl; 2AA) (1r,3r)-3-hydroxycyclobutyl; or 2AB) (1s,3s)-3-hydroxycyclobutyl.

A person of ordinary skill in the art will understand that any of 2A to 2AB may be combined with any of 1A to 1R to form any and all combinations between such substituents.

With respect to embodiments where $R^1$ is 1A to 1R and the $R^3$ embodiments 2A to 2AB, ring A may be, in any combination with 1A to 1R and 2A to 2AB: 3A) heteroaryl; 3B) nitrogen-containing heteroaryl; 3C) 5-membered heteroaryl; 3D) pyrazolyl; 3E) pyrazol-4-yl; 3F) 1-((phosphonooxy)methyl)pyrazol-4-yl; 3G) 1-((phosphonooxy)methyl) pyrazol-4-yl sodium salt; 3H) 5-fluoropyrazol-4-yl; or 3I) 3-fluoropyrazol-4-yl.

A person of ordinary skill in the art will understand that any of 3A to 3I may be combined with any of 1A to 1R and any of 2A to 2AB, to form any and all combinations between such substituents.

With respect to embodiments where $R^1$ is 1A to 1R, the $R^3$ embodiments 2A to 2AB, and the ring A embodiments 3A to 3I, $R^2$, $R^4$ and $R^5$ may be H.

In some embodiments of formula 1, the compound has a general formula 2

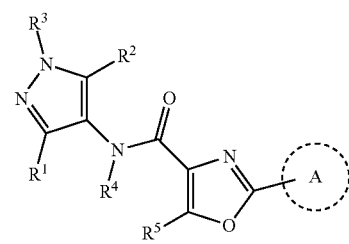

2 and/or a salt, prodrug, N-oxide or solvate thereof, where $R^1$, $R^2$, $R^3$, $R^4$, $R^5$ and ring A are as defined above with respect to formula 1.

In some embodiments of formulas 1 and 2, ring A is pyrazolyl. In certain embodiments of formulas 1 and 2, the compound has a general formula 3

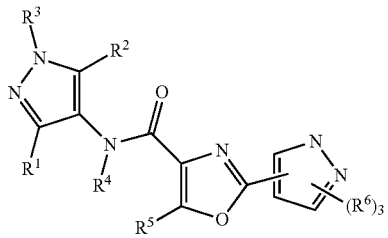

and/or a salt, prodrug, N-oxide or solvate thereof. With respect to formula 3, $R^1$, $R^2$, $R^3$, $R^4$ and $R^5$ are as previously defined with respect to formulas 1 and 2. Each $R^6$ independently is H, halogen, such as F, Cl, Br, or I, aliphatic, heteroaliphatic, aryl, —O-aliphatic, such as alkoxy, araliphatic, such as aralkyl, heterocyclyl, sulfonyl, nitro, OH, haloalkyl, carboxyl ester, cyano, acyl, amino, alkyl phosphate or alkylphosphonate. In some embodiments, at least one $R^6$ is alkylphosphonate, or a salt thereof, such as a sodium salt. In other embodiments, one, two or all three $R^6$ is or are H. In certain embodiments, at least one $R^6$ is halogen, such as F.

$R^6$ may be $R^a$, $R^b$, $R^a$ substituted with —OP(O)$(R^f)_2$, $R^a$ substituted with 1, 2 or 3 $R^b$, $R^a$ substituted with $R^c$, $R^a$ substituted with $C_{1-6}$cycloalkyl, $R^a$ substituted with —P(O)$(R^f)_2$, aralkyl, —(CR$^a$R$^a)_n$—$R^a$, —(CH$_2)_n$—$R^a$ or —C(O)C(R$^a)_2$NR$^a$R$^b$, wherein n, $R^a$, $R^b$ and $R^c$ are as previously defined, and $R^f$ is independently for each occurrence —OR$^a$, —O$^-$M$^+$ where each M$^+$ independently is an alkali metal ion, such as K$^+$, Na$^+$, Li$^+$ or an ammonium ion, such as $^+$NH$_4$ or $^+$N(R$^a)_4$, or —O$^-$[M$^{2+}]_{0.5}$ where M$^{2+}$ is an alkaline metal earth ion, such as Mg$^{2+}$, Ca$^{2+}$ or Ba$^{2+}$. In particular embodiments, $R^6$ is alkylphosphonate or cyclopropylmethyl, and in other embodiments, $R^6$ is H. In certain disclosed examples, $R^6$ is —CH$_2$OP(O)(OH)$_2$, or a salt thereof.

In particular embodiments of formula 3, the compound, and/or salt, prodrug, N-oxide or solvate thereof, has a general formula 4

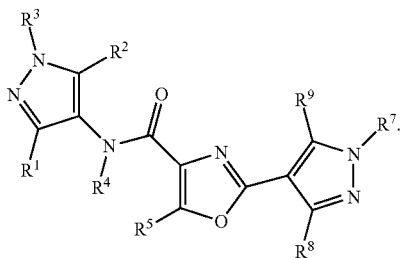

With reference to formula 4, $R^1$, $R^2$, $R^3$, $R^4$ and $R^5$ are as previously defined with respect to formulas 1, 2 and 3. $R^7$, $R^8$, and $R^9$ are each independently H, halogen, aliphatic, heteroaliphatic, aryl, —O-aliphatic, such as alkoxy, araliphatic, such as aralkyl, heterocyclyl, sulfonyl, nitro, OH, haloalkyl, carboxyl ester, cyano, acyl, amino, alkyl phosphate or alkylphosphonate. $R^7$ may be H, aliphatic, —O-aliphatic, such as alkoxy, heteroaliphatic, carboxyl ester, acyl, araliphatic, such as aralkyl, NO$_2$, CN, OH, haloalkyl, such as CF$_3$, alkyl phosphate, or alkylphosphonate. In some examples, $R^7$ is H, alkyl, carboxyl ester, acyl, alkyl phosphate, alkyl phosphonate, heterocycloalkyl or aralkyl. In particular embodiments, $R^7$ is H, alkyl, carboxyl ester, acyl, alkyl phosphate, or alkyl phosphonate.

$R^7$ may be $R^a$, $R^b$, $R^a$ substituted with —OP(O)$(R^f)_2$, $R^a$ substituted with 1, 2 or 3 $R^b$, $R^a$ substituted with $R^c$, $R^a$ substituted with —P(O)$(R^f)_2$, aralkyl, —(CR$^a$R$^a)_n$—$R^a$, —(CH$_2)_n$—$R^a$ or —C(O)C(R$^a)_2$NR$^a$R$^b$, wherein n, $R^a$, $R^b$ and $R^c$ are as previously defined, and $R^f$ is independently for each occurrence —OR$^a$, —O$^-$M$^+$ where each M$^+$ independently is an alkali metal ion, such as K$^+$, Na$^+$, Li$^+$ or an ammonium ion, such as $^+$NH$_4$ or $^+$N(R$^a)_4$, or —O$^-$[M$^{2+}]_{0.5}$ where M$^{2+}$ is an alkaline metal earth ion, such as Mg$^{2+}$, Ca$^{2+}$ or Ba$^{2+}$. In particular embodiments, $R^7$ is alkylphosphonate, and in other embodiments, $R^7$ is H. In certain disclosed examples, $R^7$ is —CH$_2$OP(O)(OH)$_2$, or a salt thereof.

$R^8$ and $R^9$ independently are $R^a$ or $R^b$.

In certain examples, $R^8$ and $R^9$ are each independently, H, halogen, such as F, alkyl or haloalkyl, such as trifluoromethyl, and in particular embodiments, $R^8$ and $R^9$ are both H; one of $R^8$ and $R^9$ is H and the other is lower alkyl, such as methyl, halogen, or trifluoromethyl; or both of $R^8$ and $R^9$ are lower alkyl. In particular embodiments, one of $R^8$ and $R^9$ is H and the other is F.

In some embodiments of formulas 1-4, $R^1$ is pyridinyl, pyrimidinyl, or pyrazinyl, and $R^2$ is H. In other embodiments of formulas 1-4, $R^2$ is pyridinyl, pyrimidinyl, or pyrazinyl, and $R^1$ is H. In some embodiments of formulas 1-4, $R^1$ is pyridinyl, pyrimidinyl, or pyrazinyl, and $R^2$, $R^4$ and $R^5$ are H. In any of these embodiments, the pyrimidinyl may be pyrimidin-2-yl or pyrimidin-4-yl, and may be substituted or unsubstituted; the pyrazinyl may be pyrazine-2-yl and may be substituted or unsubstituted; and the pyridinyl may be pyridine-2-yl and may be unsubstituted or substituted, such as with haloalkyl, halogen, or a combination thereof. In certain embodiments, the pyridinyl is a substituted pyridine-2-yl, and may be 6-(difluoromethyl)pyridin-2-yl, 3-fluoro-6-(trifluoromethyl)pyridin-2-yl, 3,6-difluoropyridin-2-yl, 3,5-difluoropyridin-2-yl, 3,5,6-trifluoropyridin-2-yl, or 4,6-difluoropyridin-2-yl. In any of these embodiments, $R^3$ may be a 1,4-substituted cyclohexyl, or a 1,3-substituted cyclobutyl.

In other embodiments, one of $R^1$ and $R^2$ is H, and the other is pyridin-3-yl or pyridin-4-yl.

In some embodiments of formulas 1-4, $R^1$ is pyrazinyl and $R^2$ is H. In other embodiments of formulas 1-4, $R^1$ is pyrimidinyl, such as pyrimidin-2-yl, and $R^2$ is H. In other embodiments, $R^1$ is pyridinyl and $R^2$ is H.

In some embodiments of formulas 1-4, $R^3$ is 1,4-substituted cyclohexyl, $R^2$ is H, and $R^1$ is pyrazinyl. In other embodiments of formulas 1-4, $R^3$ is 1,4-substituted cyclohexyl, $R^2$ is H, and $R^1$ is pyrimidin-2-yl. In other embodiments of formulas 1-4, $R^3$ is 1,3-substituted cyclobutyl, $R^2$ is H, and $R^1$ is pyrazinyl. In other embodiments of formulas 1-4, $R^3$ is 1,3-substituted cyclobutyl, $R^2$ is H, and $R^1$ is pyrimidin-2-yl. In further embodiments of formulas 1-4, $R^3$ is 1,4-substituted cyclohexyl, $R^2$ is H, and $R^1$ is pyridin-2-yl. In still further embodiments of formulas 1-4, $R^3$ is 1,4-substituted cyclobutyl, $R^2$ is H, and $R^1$ is pyridin-2-yl.

In any of the above embodiments of formulas 1-4, $R^1$ may be

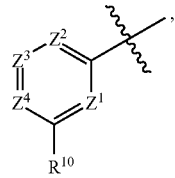

wherein $Z^1$, $Z^2$, $Z^3$ and $Z^4$ independently are N or $CR^{10}$, where each $R^{10}$ independently is H, halogen, or aliphatic, such as alkyl, and at least one, such as one, two, three or four of $Z^1$, $Z^2$, $Z^3$ and $Z^4$ is N. In some embodiments, each $R^{10}$ independently is H, halogen or haloalkyl, such as H, F, $CF_3$, or $CF_2$.

In some embodiments, $Z^1$ is N, and none or one of $Z^2$, $Z^3$ and $Z^4$ is N. In certain embodiments, $Z^1$ and $Z^2$ are N, and $Z^3$ and $Z^4$ are $CR^{10}$. In other embodiments, $Z^1$ and $Z^3$ are N, and $Z^2$ and $Z^4$ are $CR^{10}$. In further embodiments, $Z^1$ and $Z^4$ are N, and $Z^2$ and $Z^3$ are $CR^{10}$.

In some embodiments of formulas 1-4, the compound, and/or salt, prodrug, N-oxide or solvate thereof, has a general formula selected from formulas 5-8:

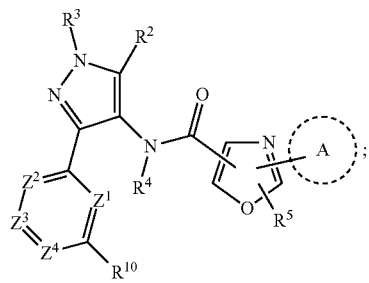

5

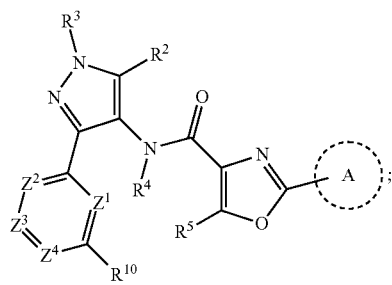

6

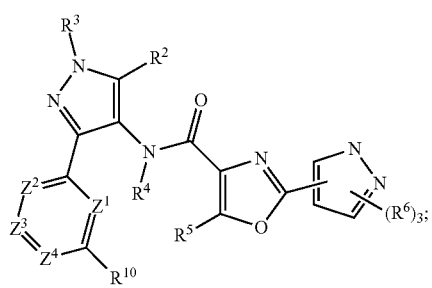

7

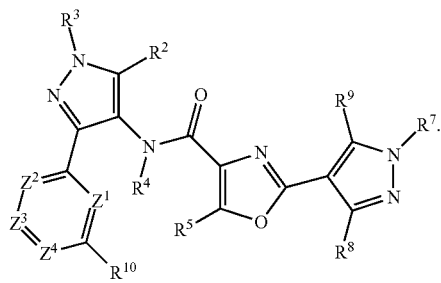

8

With respect to formulas 5-8, $R^2$, $R^3$, $R^4$, $R^5$, $R^6$, $R^7$, $R^8$, $R^9$, $R^{10}$, $Z^1$, $Z^2$, $Z^3$, $Z^4$ and ring A, if present, are as previously defined for formulas 1-4.

In certain embodiments of formulas 1-8, the compound, and/or salt, prodrug, N-oxide or solvate thereof, has a general formula selected from

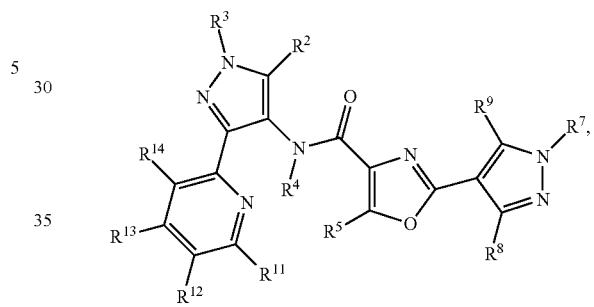

9

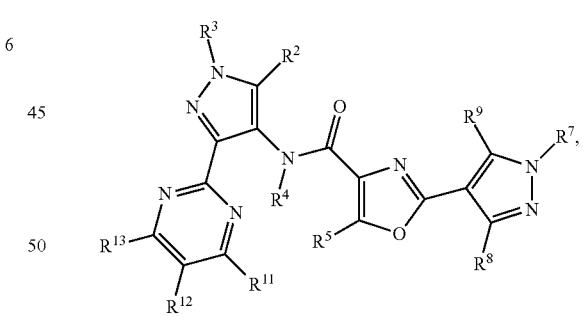

10

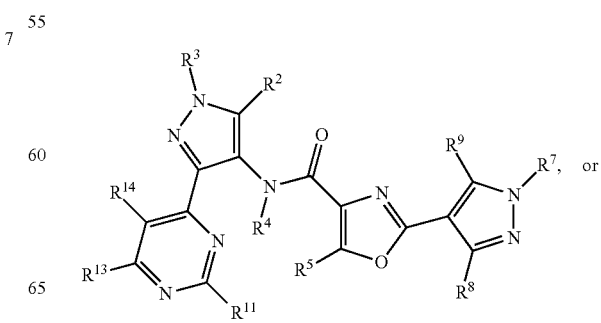

11

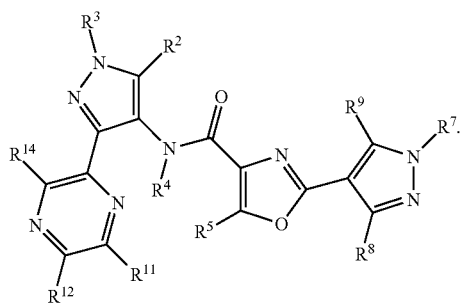

With respect to formulas 9-12, $R^2$, $R^3$, $R^4$, $R^5$, $R^7$, $R^8$, and $R^9$ are as defined for formulas 1-8, and $R^{11}$, $R^{12}$, $R^{13}$, and $R^{14}$, if present, are independently H, halogen, or aliphatic, such as alkyl. In certain embodiments, $R^{11}$, $R^{12}$, $R^{13}$, and $R^{14}$, if present, are independently H, halogen, or haloalkyl, and independently may be H, F, $CF_3$, or $CF_2$.

In some embodiments of formulas 1-12, $R^4$ is H, $R^5$ is H, or both $R^4$ and $R^5$ are H.

In some embodiments of formulas 1-12, $R^3$ is a $C_{5-10}$cycloalkyl, and in certain embodiments, $R^3$ is cyclohexyl, such as 1,4-substituted cyclohexyl. In other embodiments of formulas 1-12, $R^3$ is cyclobutyl, such as 1,3-substituted cyclobutyl.

Exemplary compound according to formula 1 include:

I-1

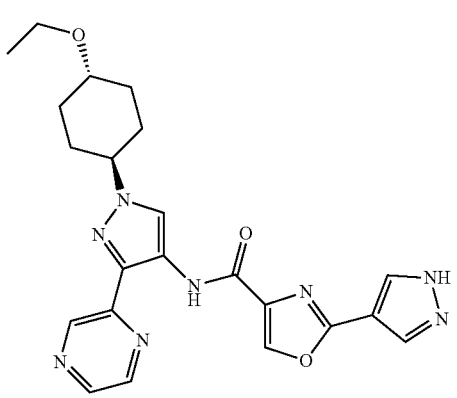

I-2

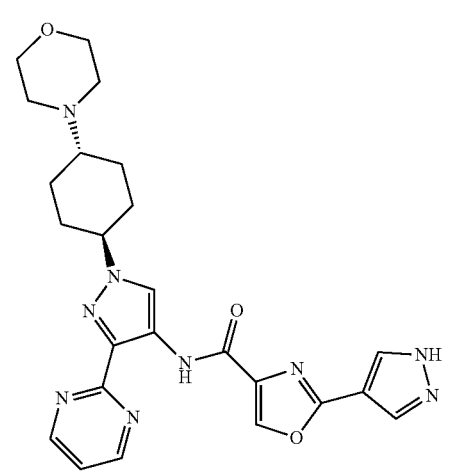

I-3

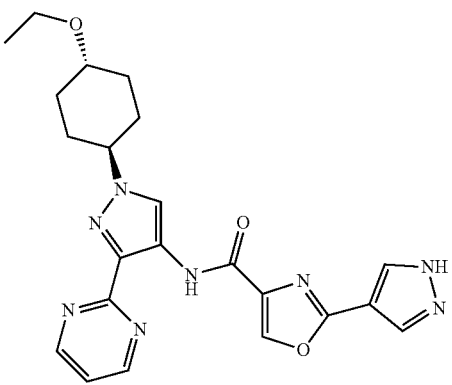

I-4

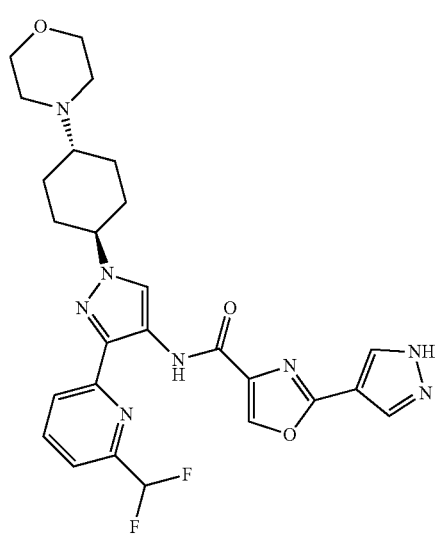

I-5

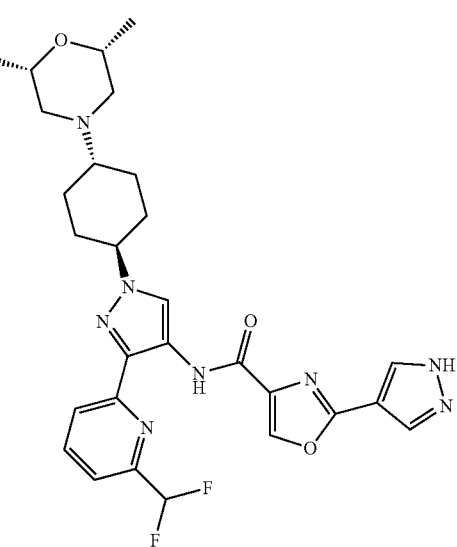

I-6
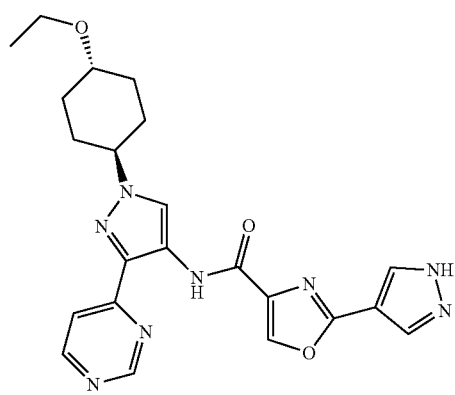
I-7
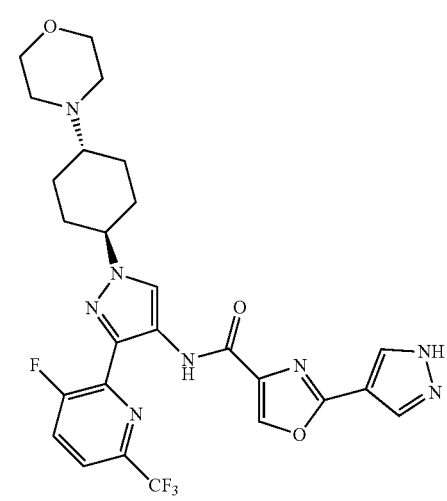
I-8
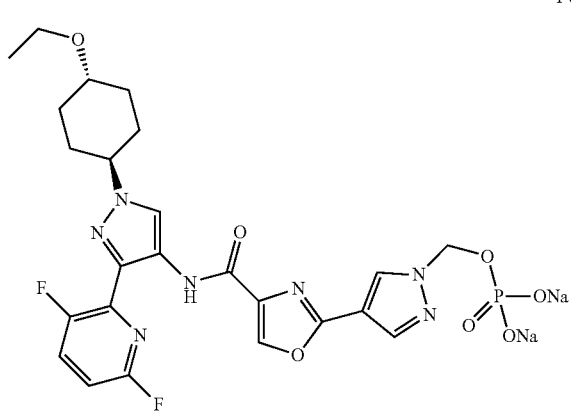
I-9
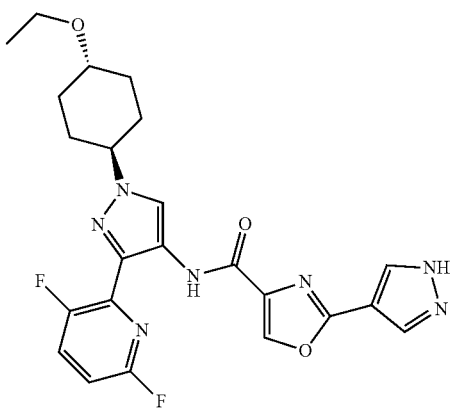
I-10
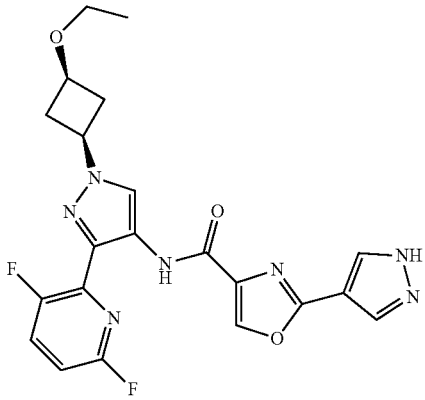
I-11
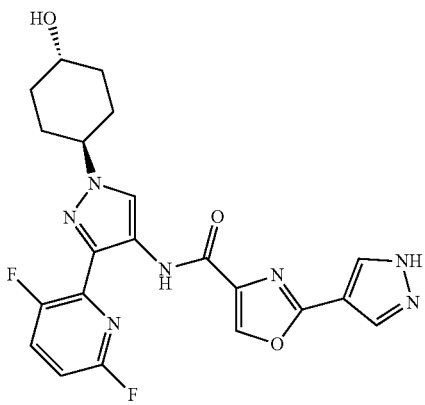
I-12
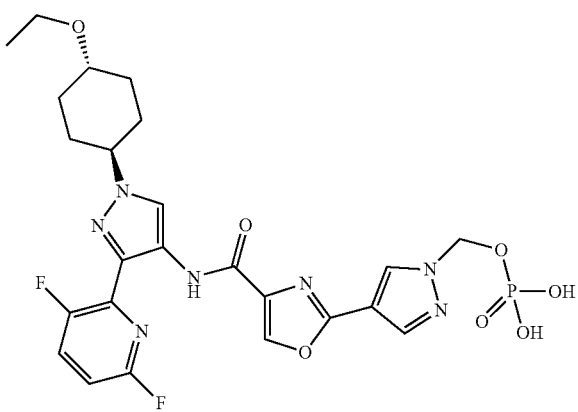

-continued
I-13
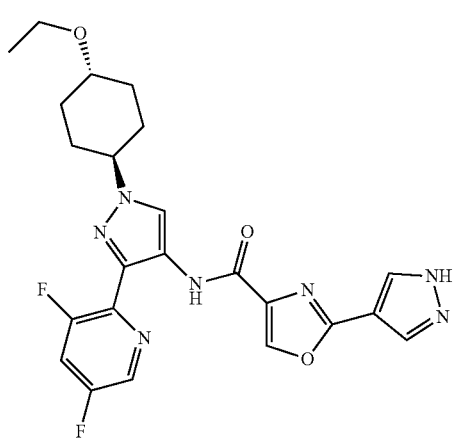
I-14
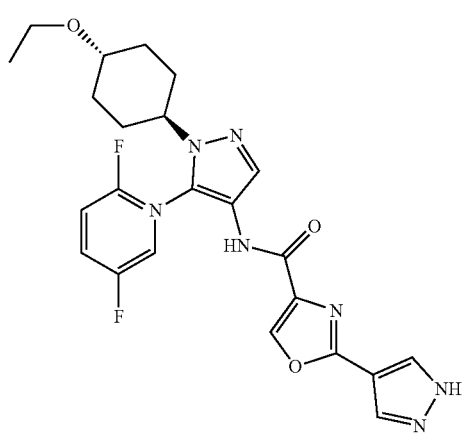
I-15
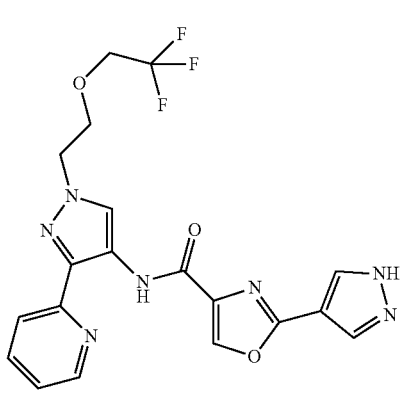
I-16
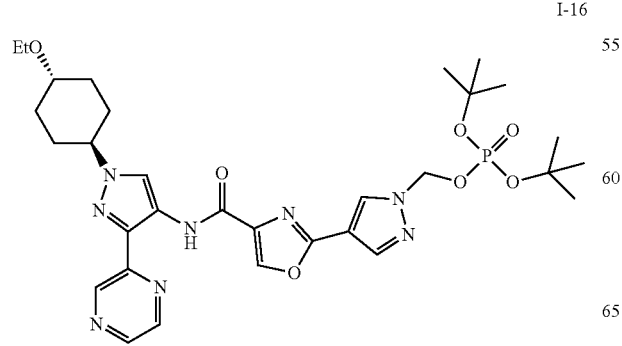
-continued
I-17
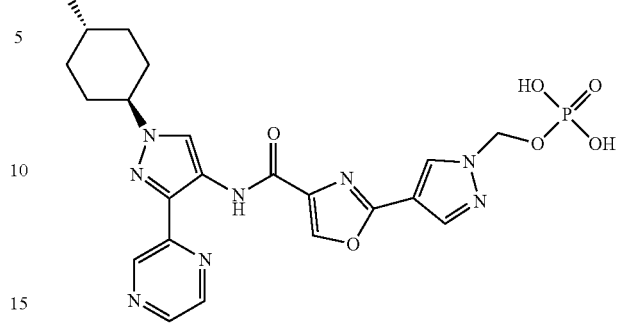
I-18
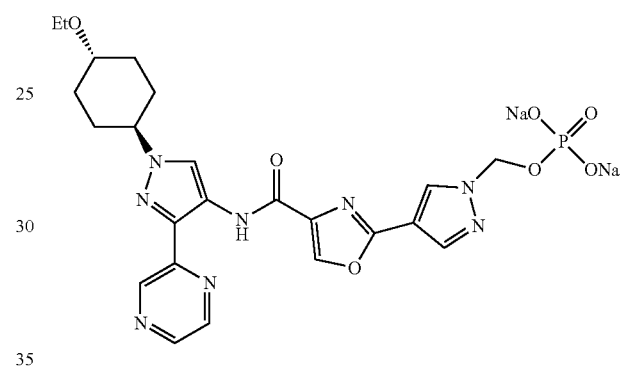
I-19
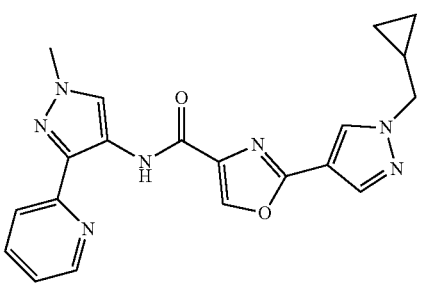
I-20
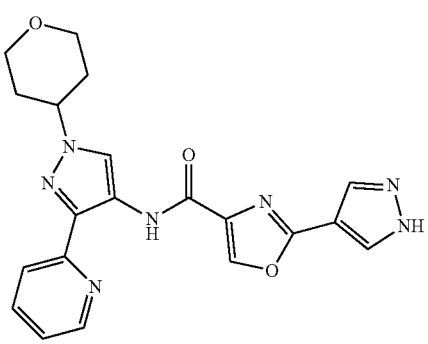

I-21
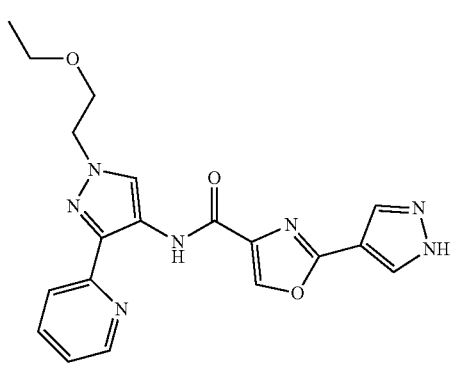
I-22
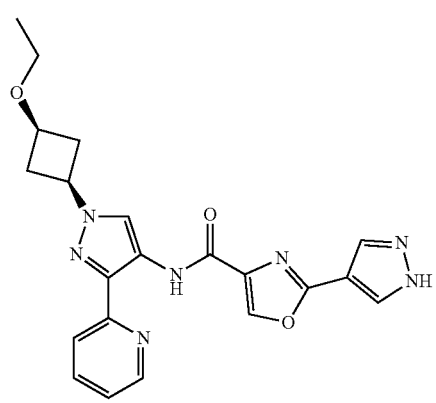
I-23
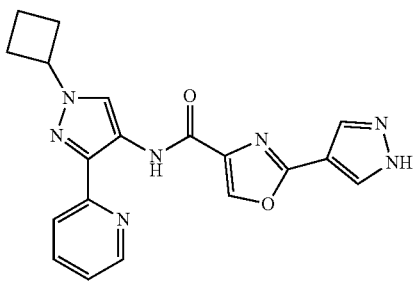
I-24
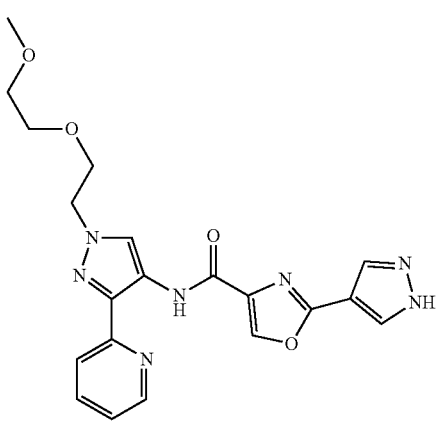
I-25
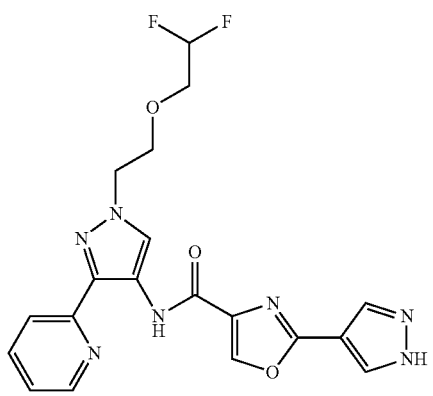
I-26
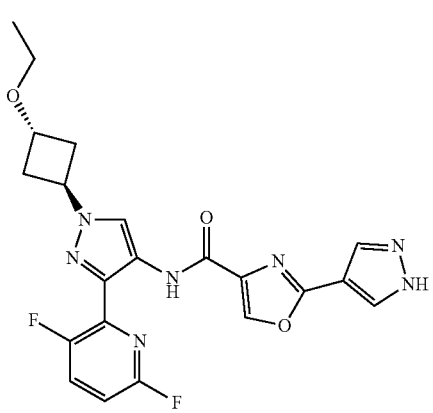
I-27
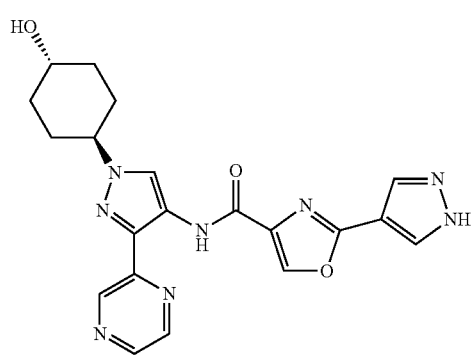
I-28
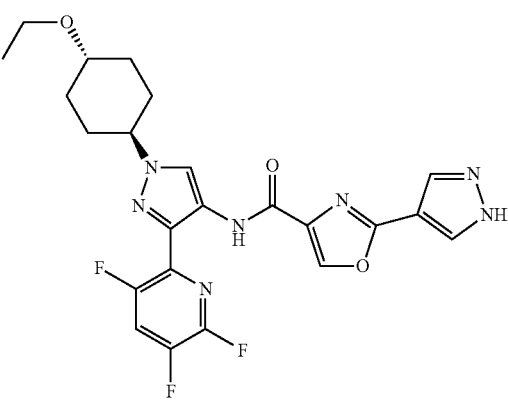

I-29
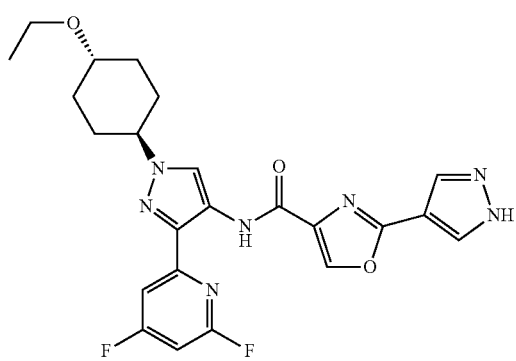
I-30
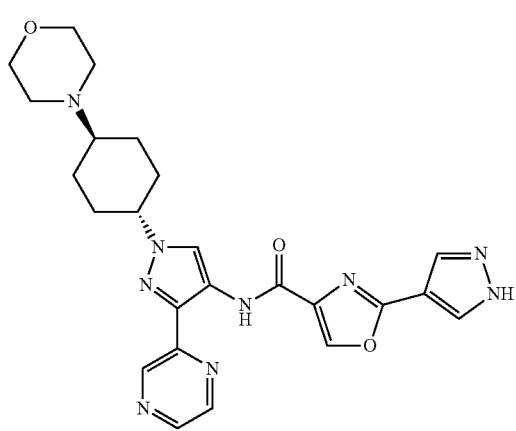
I-31
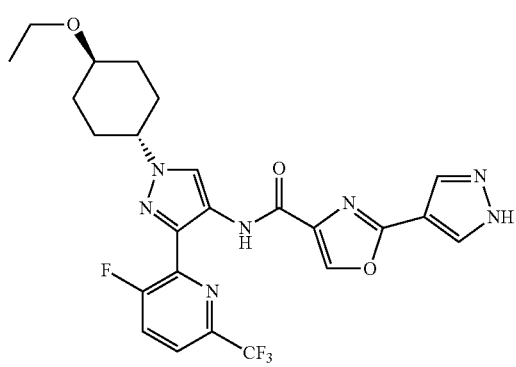
I-32
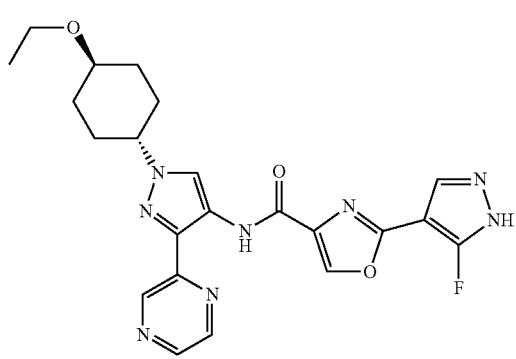
I-33
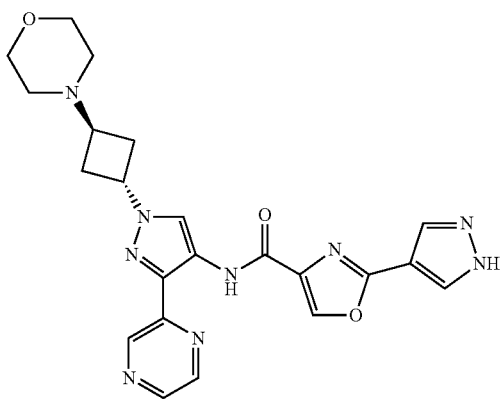
I-34
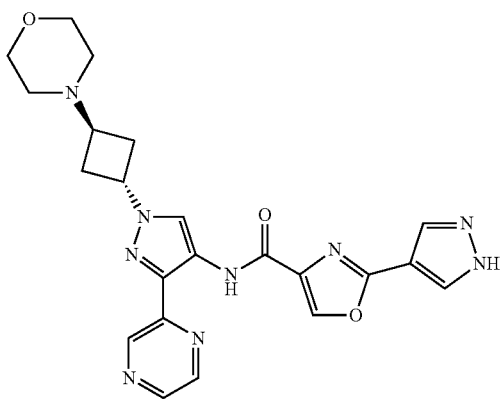
I-35
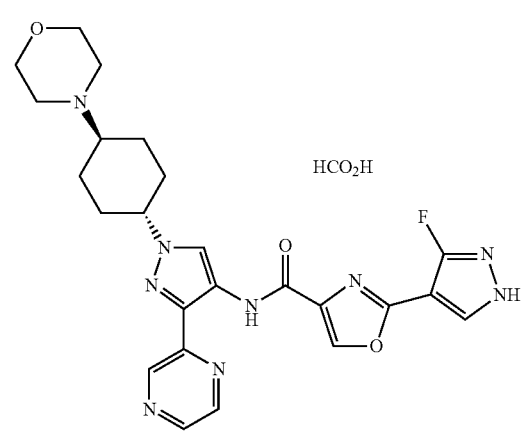

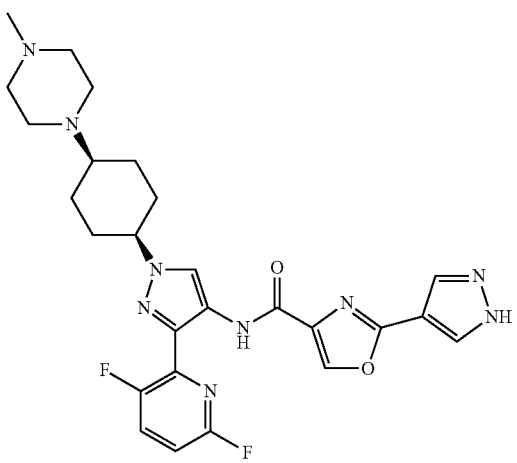

I-36

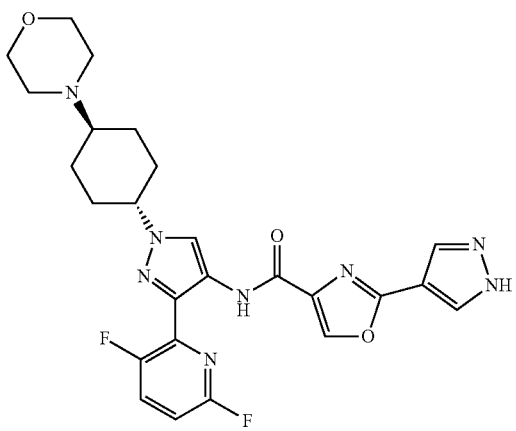

I-37

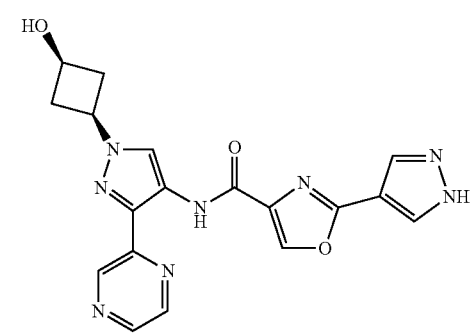

I-38

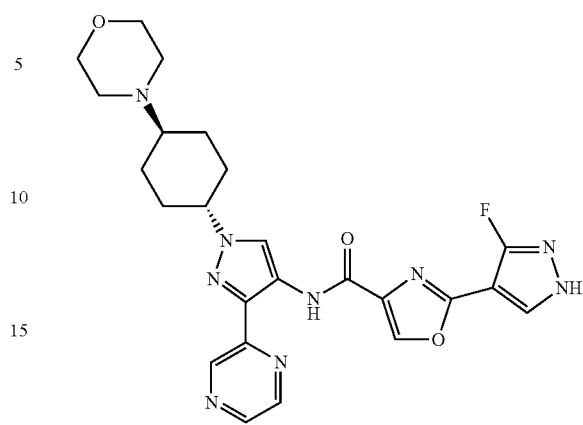

I-39

In certain embodiments, exemplary compound according to formula 1 include:

I-1: N-(1-((1r,4r)-4-ethoxycyclohexyl)-3-(pyrazin-2-yl)-1H-pyrazol-4-yl)-2-(1H-pyrazol-4-yl)oxazole-4-carboxamide;

I-2: N-(1-((1r,4r)-4-morpholinocyclohexyl)-3-(pyrimidin-2-yl)-1H-pyrazol-4-yl)-2-(1H-pyrazol-4-yl)oxazole-4-carboxamide;

I-3: N-(1-((1r,4r)-4-ethoxycyclohexyl)-3-(pyrimidin-2-yl)-1H-pyrazol-4-yl)-2-(1H-pyrazol-4-yl)oxazole-4-carboxamide;

I-4: N-(3-(6-(difluoromethyl)pyridin-2-yl)-1-((1r,4r)-4-morpholinocyclohexyl)-1H-pyrazol-4-yl)-2-(1H-pyrazol-4-yl)oxazole-4-carboxamide;

I-5: N-(3-(6-(difluoromethyl)pyridin-2-yl)-1-((1R,4r)-4-((2R,6S)-2,6-dimethylmorpholino)cyclohexyl)-1H-pyrazol-4-yl)-2-(1H-pyrazol-4-yl)oxazole-4-carboxamide;

I-6: N-(1-((1r,4r)-4-ethoxycyclohexyl)-3-(pyrimidin-4-yl)-1H-pyrazol-4-yl)-2-(1H-pyrazol-4-yl)oxazole-4-carboxamide;

I-7: N-(3-(3-fluoro-6-(trifluoromethyl)pyridin-2-yl)-1-((1r,4r)-4-morpholinocyclohexyl)-1H-pyrazol-4-yl)-2-(1H-pyrazol-4-yl)oxazole-4-carboxamide;

I-8: sodium (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl)methyl phosphate;

I-9: N-(3-(3,6-difluoropyridin-2-yl)-1-((1r,4r)-4-ethoxycyclohexyl)-1H-pyrazol-4-yl)-2-(1H-pyrazol-4-yl)oxazole-4-carboxamide;

I-10: N-(3-(3,6-difluoropyridin-2-yl)-1-((1s,3s)-3-ethoxycyclobutyl)-1H-pyrazol-4-yl)-2-(1H-pyrazol-4-yl)oxazole-4-carboxamide;

I-11: N-(3-(3,6-difluoropyridin-2-yl)-1-((1r,4r)-4-hydroxycyclohexyl)-1H-pyrazol-4-yl)-2-(1H-pyrazol-4-yl)oxazole-4-carboxamide;

I-12: (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl)methyl dihydrogen phosphate;

I-13: N-(3-(3,5-difluoropyridin-2-yl)-1-((1r,4r)-4-ethoxycyclohexyl)-1H-pyrazol-4-yl)-2-(1H-pyrazol-4-yl)oxazole-4-carboxamide;

I-14: N-(5-(3,6-difluoropyridin-2-yl)-1-((1r,4R)-4-ethoxycyclohexyl)-1H-pyrazol-4-yl)-2-(1H-pyrazol-4-yl)oxazole-4-carboxamide;

I-15: 2-(1H-pyrazol-4-yl)-N-(3-(pyridin-2-yl)-1-(2-(2,2,2-trifluoroethoxy)ethyl)-1H-pyrazol-4-yl)oxazole-4-carboxamide;

I-16: di-tert-butyl ((4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl) phosphate;

I-17: (4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl dihydrogen phosphate;

I-18: sodium (4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl phosphate;

I-19: 2-(1-(cyclopropylmethyl)-1H-pyrazol-4-yl)-N-(1-methyl-3-(pyridin-2-yl)-1H-pyrazol-4-yl)oxazole-4-carboxamide;

I-20: 2-(1H-pyrazol-4-yl)-N-(3-(pyridin-2-yl)-1-(tetrahydro-2H-pyran-4-yl)-1H-pyrazol-4-yl)oxazole-4-carboxamide;

I-21: N-(1-(2-ethoxyethyl)-3-(pyridin-2-yl)-1H-pyrazol-4-yl)-2-(1H-pyrazol-4-yl)oxazole-4-carboxamide;

I-22: N-(1-((1s,3s)-3-ethoxycyclobutyl)-3-(pyridin-2-yl)-1H-pyrazol-4-yl)-2-(1H-pyrazol-4-yl)oxazole-4-carboxamide;

I-23: N-(1-cyclobutyl-3-(pyridin-2-yl)-1H-pyrazol-4-yl)-2-(1H-pyrazol-4-yl)oxazole-4-carboxamide;

I-24: N-(1-(2-(2-methoxyethoxy)ethyl)-3-(pyridin-2-yl)-1H-pyrazol-4-yl)-2-(1H-pyrazol-4-yl)oxazole-4-carboxamide;

I-25: N-(1-(2-(2,2-difluoroethoxy)ethyl)-3-(pyridin-2-yl)-1H-pyrazol-4-yl)-2-(1H-pyrazol-4-yl)oxazole-4-carboxamide;

I-26: N-(3-(3,6-difluoropyridin-2-yl)-1-((1r,3r)-3-ethoxycyclobutyl)-1H-pyrazol-4-yl)-2-(1H-pyrazol-4-yl)oxazole-4-carboxamide;

I-27: N-(1-((1r,4r)-4-hydroxycyclohexyl)-3-(pyrazin-2-yl)-1H-pyrazol-4-yl)-2-(1H-pyrazol-4-yl)oxazole-4-carboxamide;

I-28: N-(1-((1r,4r)-4-ethoxycyclohexyl)-3-(3,5,6-trifluoropyridin-2-yl)-1H-pyrazol-4-yl)-2-(1H-pyrazol-4-yl)oxazole-4-carboxamide;

I-29: N-(3-(4,6-difluoropyridin-2-yl)-1-((1r,4r)-4-ethoxycyclohexyl)-1H-pyrazol-4-yl)-2-(1H-pyrazol-4-yl)oxazole-4-carboxamide;

I-30: N-(1-((1r,4r)-4-morpholinocyclohexyl)-3-(pyrazin-2-yl)-1H-pyrazol-4-yl)-2-(1H-pyrazol-4-yl)oxazole-4-carboxamide;

I-31: N-(1-((1r,4r)-4-ethoxycyclohexyl)-3-(3-fluoro-6-(trifluoromethyl)pyridin-2-yl)-1H-pyrazol-4-yl)-2-(1H-pyrazol-4-yl)oxazole-4-carboxamide;

I-32: N-(1-((1r,4r)-4-ethoxycyclohexyl)-3-(pyrazin-2-yl)-1H-pyrazol-4-yl)-2-(5-fluoro-1H-pyrazol-4-yl)oxazole-4-carboxamide;

I-33: N-(1-((1r,3r)-3-morpholinocyclobutyl)-3-(pyrazin-2-yl)-1H-pyrazol-4-yl)-2-(1H-pyrazol-4-yl)oxazole-4-carboxamide;

I-34: N-(1-((1s,3s)-3-morpholinocyclobutyl)-3-(pyrazin-2-yl)-1H-pyrazol-4-yl)-2-(1H-pyrazol-4-yl)oxazole-4-carboxamide;

I-35: 2-(3-fluoro-1H-pyrazol-4-yl)-N-(1-((1r,4r)-4-morpholinocyclohexyl)-3-(pyrazin-2-yl)-1H-pyrazol-4-yl)oxazole-4-carboxamide formic acid salt;

I-36: N-(3-(3,6-difluoropyridin-2-yl)-1-((1s,4s)-4-(4-methylpiperazin-1-yl)cyclohexyl)-1H-pyrazol-4-yl)-2-(1H-pyrazol-4-yl)oxazole-4-carboxamide;

I-37: N-(3-(3,6-difluoropyridin-2-yl)-1-((1r,4r)-4-morpholinocyclohexyl)-1H-pyrazol-4-yl)-2-(1H-pyrazol-4-yl)oxazole-4-carboxamide;

I-38: N-(1-((1s,3s)-3-hydroxycyclobutyl)-3-(pyrazin-2-yl)-1H-pyrazol-4-yl)-2-(1H-pyrazol-4-yl)oxazole-4-carboxamide; or I-39: 2-(3-fluoro-1H-pyrazol-4-yl)-N-(1-((1r,4r)-4-morpholinocyclohexyl)-3-(pyrazin-2-yl)-1H-pyrazol-4-yl)oxazole-4-carboxamide.

Some exemplary compounds according to formula 1 include:

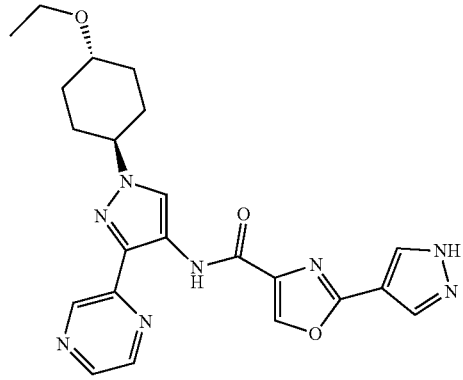

II-1

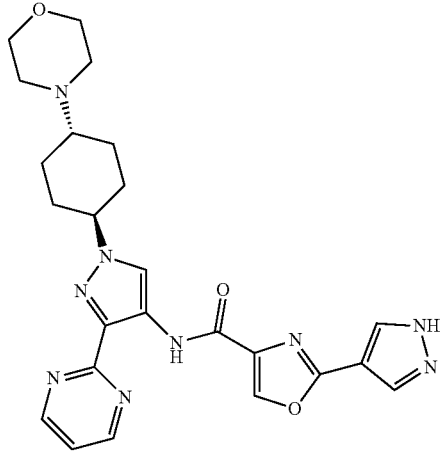

II-2

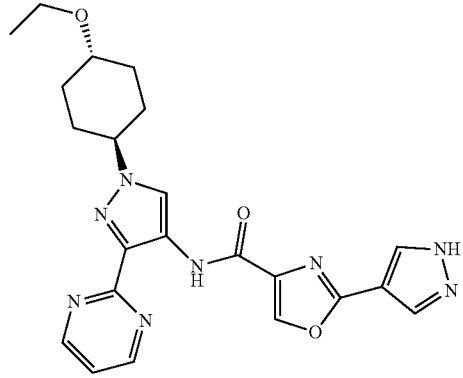

II-3

II-4
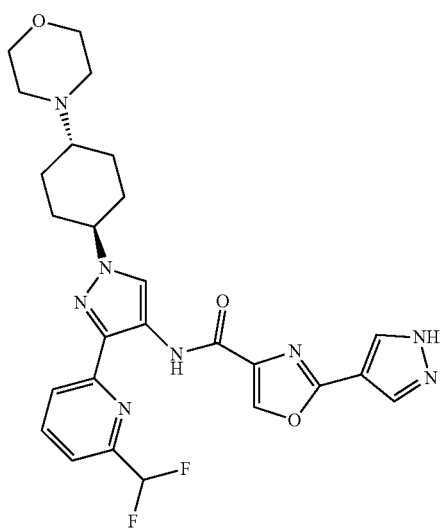
II-5
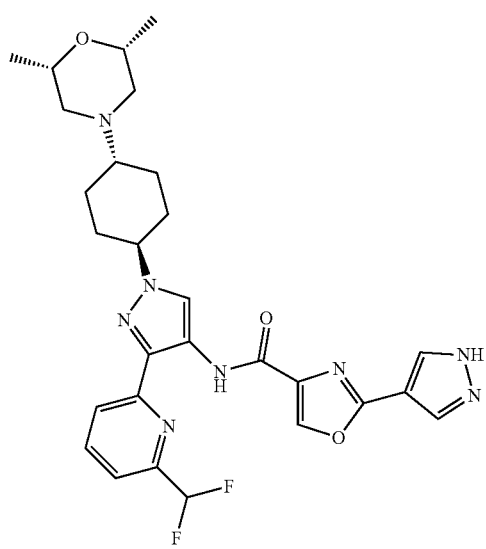
II-6
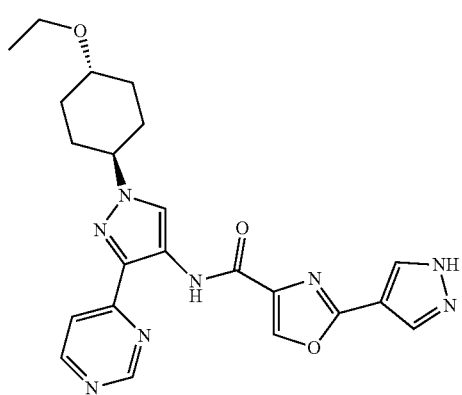
II-7
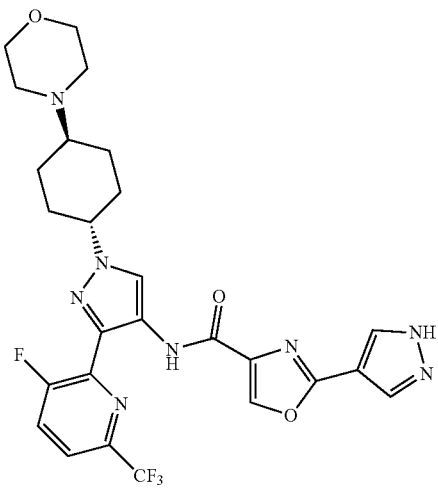
II-8
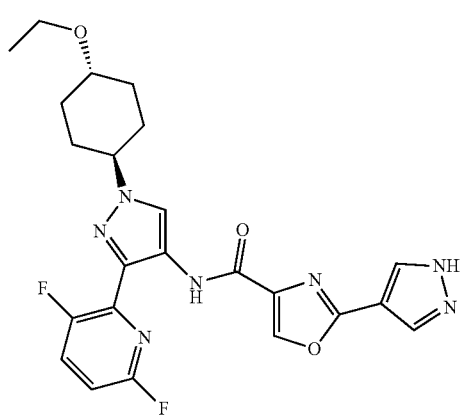
II-9

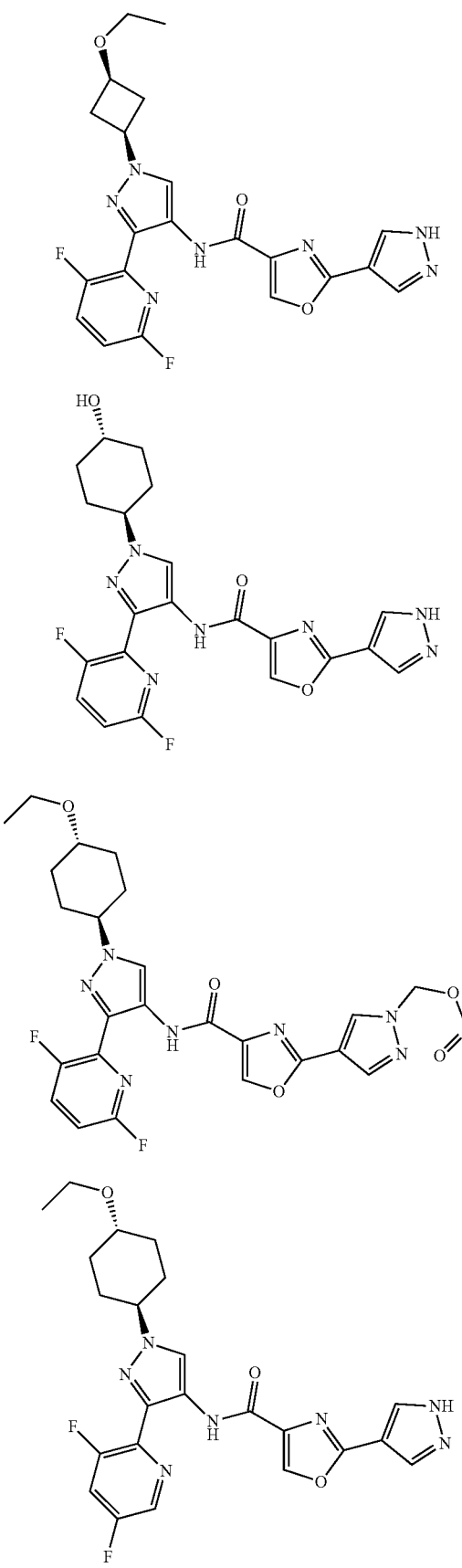
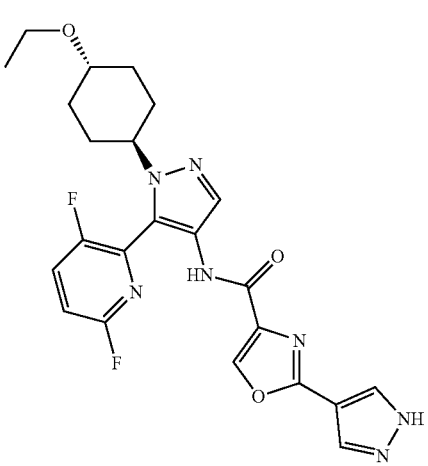
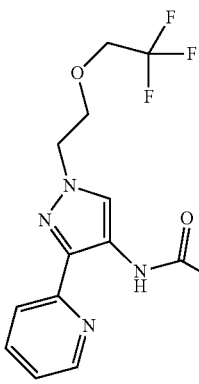
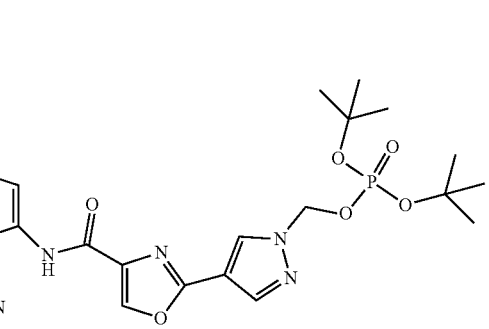
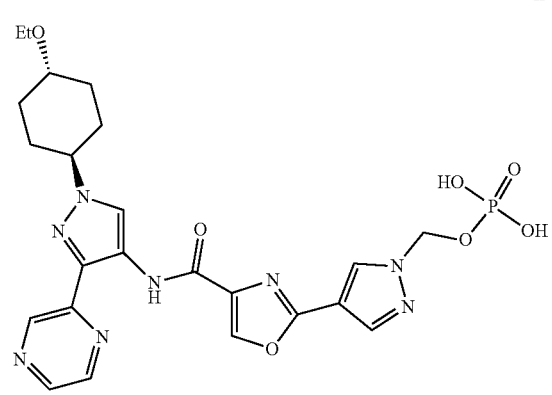

II-18
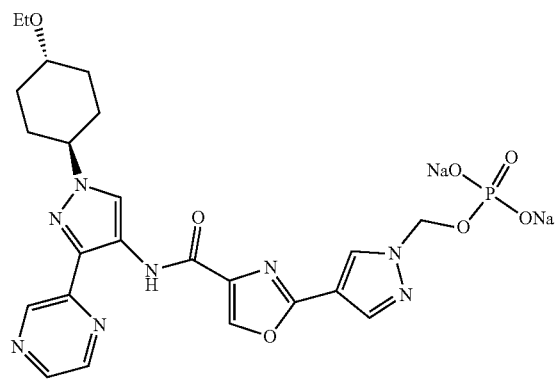
II-22
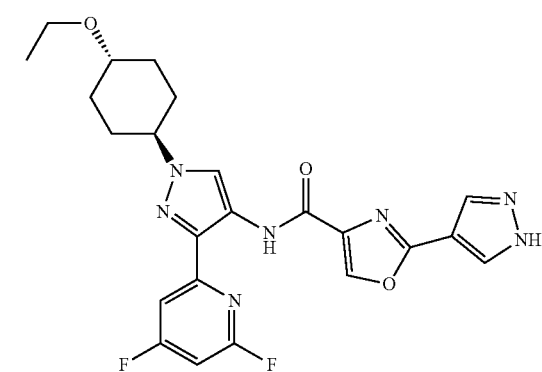
II-19
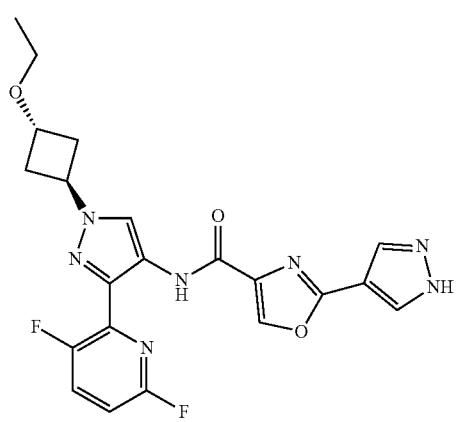
II-23
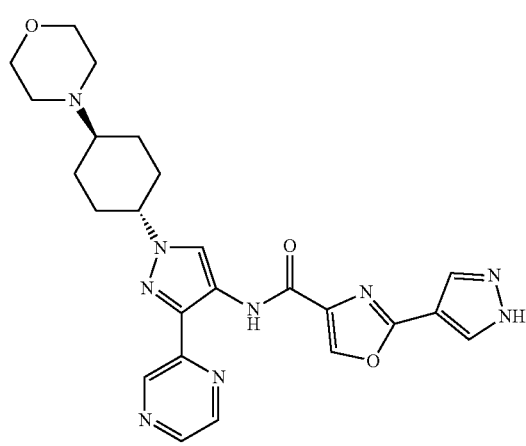
II-20
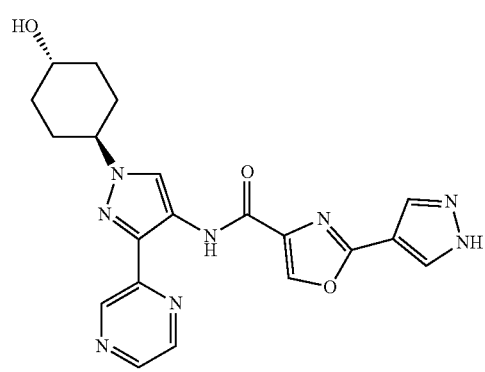
II-24
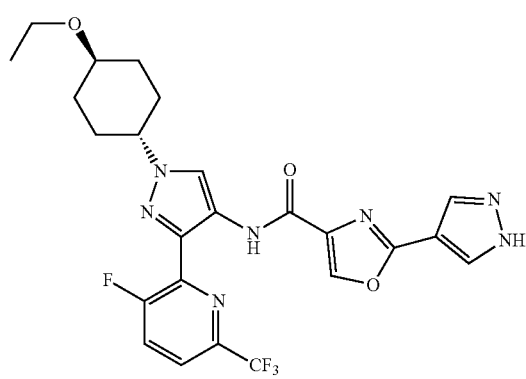
II-21
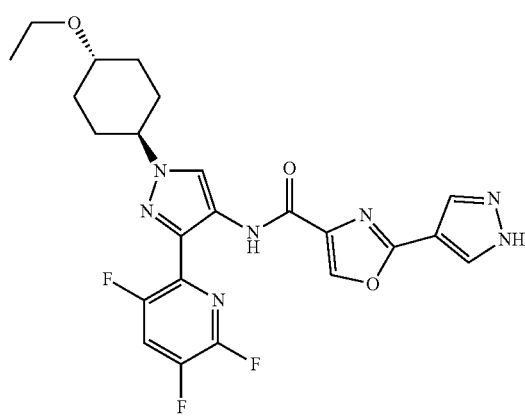
II-25
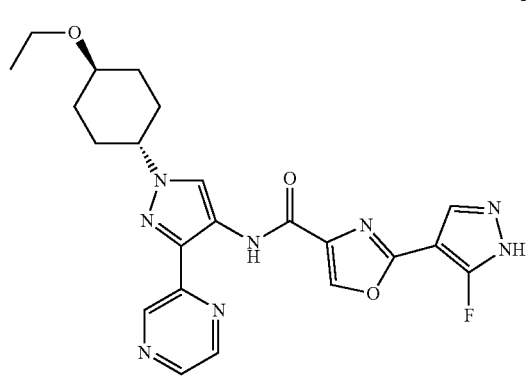

II-26
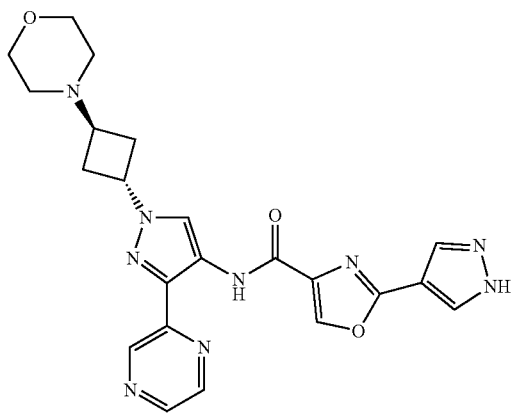
II-29
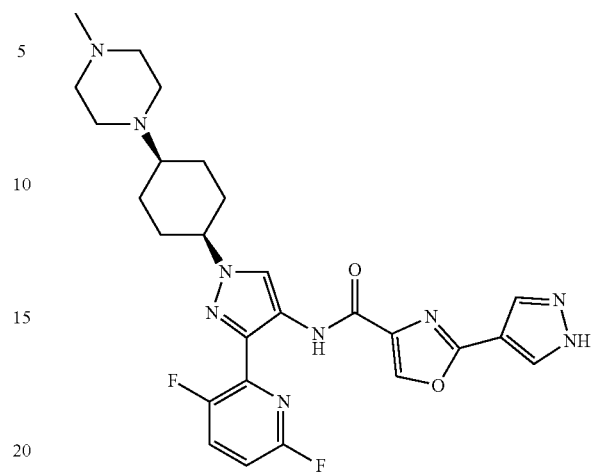
II-27
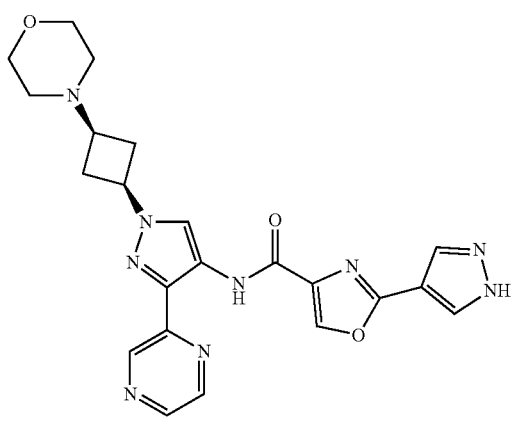
II-30
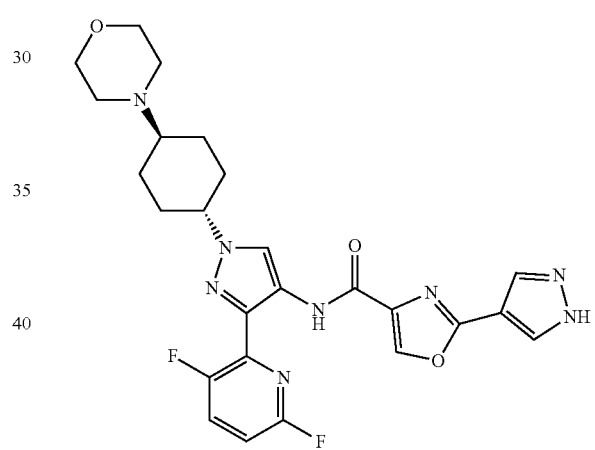
II-28
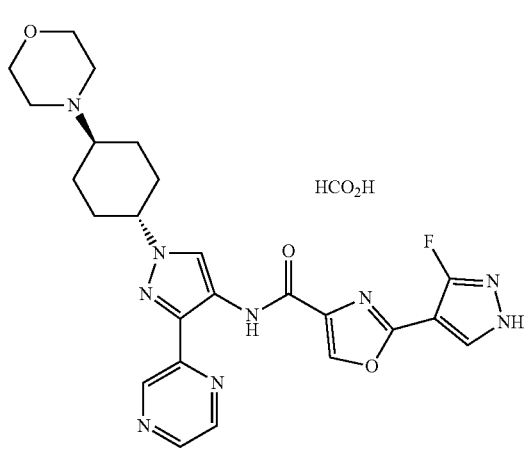
II-31
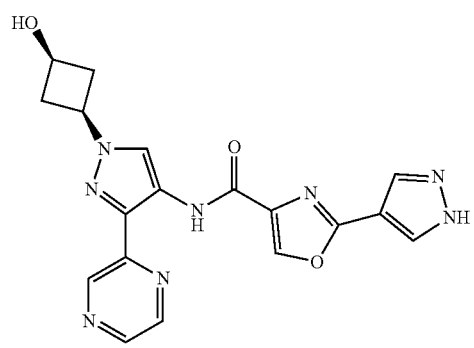

-continued

II-32

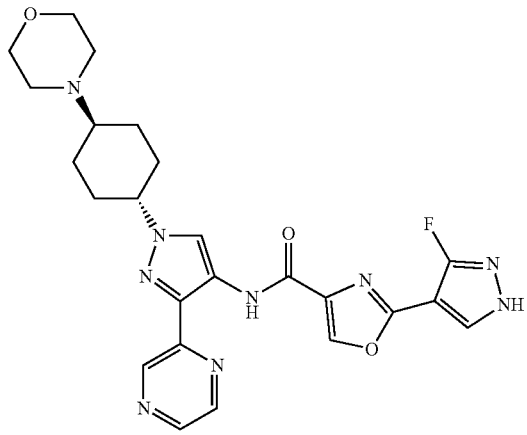

Exemplary compounds according to formula 1 include:

II-1: N-(1-((1r,4r)-4-ethoxycyclohexyl)-3-(pyrazin-2-yl)-1H-pyrazol-4-yl)-2-(1H-pyrazol-4-yl)oxazole-4-carboxamide;

II-2: N-(1-((1r,4r)-4-morpholinocyclohexyl)-3-(pyrimidin-2-yl)-1H-pyrazol-4-yl)-2-(1H-pyrazol-4-yl)oxazole-4-carboxamide;

II-3: N-(1-((1r,4r)-4-ethoxycyclohexyl)-3-(pyrimidin-2-yl)-1H-pyrazol-4-yl)-2-(1H-pyrazol-4-yl)oxazole-4-carboxamide;

II-4: N-(3-(6-(difluoromethyl)pyridin-2-yl)-1-((1r,4r)-4-morpholinocyclohexyl)-1H-pyrazol-4-yl)-2-(1H-pyrazol-4-yl)oxazole-4-carboxamide;

II-5: N-(3-(6-(difluoromethyl)pyridin-2-yl)-1-((1R,4r)-4-((2R,6S)-2,6-dimethylmorpholino)cyclohexyl)-1H-pyrazol-4-yl)-2-(1H-pyrazol-4-yl)oxazole-4-carboxamide;

II-6: N-(1-((1r,4r)-4-ethoxycyclohexyl)-3-(pyrimidin-4-yl)-1H-pyrazol-4-yl)-2-(1H-pyrazol-4-yl)oxazole-4-carboxamide;

II-7: N-(3-(3-fluoro-6-(trifluoromethyl)pyridin-2-yl)-1-((1r,4r)-4-morpholinocyclohexyl)-H-pyrazol-4-yl)-2-(1H-pyrazol-4-yl)oxazole-4-carboxamide;

II-8: sodium (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl)methyl phosphate;

II-9: N-(3-(3,6-difluoropyridin-2-yl)-1-((1r,4r)-4-ethoxycyclohexyl)-1H-pyrazol-4-yl)-2-(1H-pyrazol-4-yl)oxazole-4-carboxamide;

II-10: N-(3-(3,6-difluoropyridin-2-yl)-1-((1s,3s)-3-ethoxycyclobutyl)-1H-pyrazol-4-yl)-2-(1H-pyrazol-4-yl)oxazole-4-carboxamide;

II-11: N-(3-(3,6-difluoropyridin-2-yl)-1-((1r,4r)-4-hydroxycyclohexyl)-1H-pyrazol-4-yl)-2-(1H-pyrazol-4-yl)oxazole-4-carboxamide;

II-12: (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl)methyl dihydrogen phosphate;

II-13: N-(3-(3,5-difluoropyridin-2-yl)-1-((1r,4r)-4-ethoxycyclohexyl)-1H-pyrazol-4-yl)-2-(1H-pyrazol-4-yl)oxazole-4-carboxamide;

II-14: N-(5-(3,6-difluoropyridin-2-yl)-1-((1r,4R)-4-ethoxycyclohexyl)-1H-pyrazol-4-yl)-2-(1H-pyrazol-4-yl)oxazole-4-carboxamide;

II-15: 2-(1H-pyrazol-4-yl)-N-(3-(pyridin-2-yl)-1-(2-(2,2,2-trifluoroethoxy)ethyl)-1H-pyrazol-4-yl)oxazole-4-carboxamide;

II-16: di-tert-butyl ((4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl) phosphate;

II-17: (4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl dihydrogen phosphate;

II-18: sodium (4-(4-((1-((1 r,4r)-4-ethoxycyclohexyl)-3-(pyrazin-2-yl)-1H-pyrazol-4-yl)carbamoyl)oxazol-2-yl)-1H-pyrazol-1-yl)methyl phosphate;

II-19: N-(3-(3,6-difluoropyridin-2-yl)-1-((1r,3r)-3-ethoxycyclobutyl)-1H-pyrazol-4-yl)-2-(1H-pyrazol-4-yl)oxazole-4-carboxamide;

II-20: N-(1-((1r,4r)-4-hydroxycyclohexyl)-3-(pyrazin-2-yl)-1H-pyrazol-4-yl)-2-(1H-pyrazol-4-yl)oxazole-4-carboxamide;

II-21: N-(1-((1r,4r)-4-ethoxycyclohexyl)-3-(3,5,6-trifluoropyridin-2-yl)-1H-pyrazol-4-yl)-2-(1H-pyrazol-4-yl)oxazole-4-carboxamide;

II-22: N-(3-(4,6-difluoropyridin-2-yl)-1-((1r,4r)-4-ethoxycyclohexyl)-1H-pyrazol-4-yl)-2-(1H-pyrazol-4-yl)oxazole-4-carboxamide;

II-23: N-(1-((1r,4r)-4-morpholinocyclohexyl)-3-(pyrazin-2-yl)-1H-pyrazol-4-yl)-2-(1H-pyrazol-4-yl)oxazole-4-carboxamide;

II-24: N-(1-((1r,4r)-4-ethoxycyclohexyl)-3-(3-fluoro-6-(trifluoromethyl)pyridin-2-yl)-1H-pyrazol-4-yl)-2-(1H-pyrazol-4-yl)oxazole-4-carboxamide;

II-25: N-(1-((1r,4r)-4-ethoxycyclohexyl)-3-(pyrazin-2-yl)-1H-pyrazol-4-yl)-2-(5-fluoro-1H-pyrazol-4-yl)oxazole-4-carboxamide;

II-26: N-(1-((1r,3r)-3-morpholinocyclobutyl)-3-(pyrazin-2-yl)-1H-pyrazol-4-yl)-2-(1H-pyrazol-4-yl)oxazole-4-carboxamide;

II-27: N-(1-((1s,3s)-3-morpholinocyclobutyl)-3-(pyrazin-2-yl)-1H-pyrazol-4-yl)-2-(1H-pyrazol-4-yl)oxazole-4-carboxamide;

II-28: 2-(3-fluoro-1H-pyrazol-4-yl)-N-(1-((1r,4r)-4-morpholinocyclohexyl)-3-(pyrazin-2-yl)-1H-pyrazol-4-yl)oxazole-4-carboxamide formic acid salt;

II-29: N-(3-(3,6-difluoropyridin-2-yl)-1-((1s,4s)-4-(4-methylpiperazin-1-yl)cyclohexyl)-1H-pyrazol-4-yl)-2-(1H-pyrazol-4-yl)oxazole-4-carboxamide;

II-30: N-(3-(3,6-difluoropyridin-2-yl)-1-((1r,4r)-4-morpholinocyclohexyl)-1H-pyrazol-4-yl)-2-(1H-pyrazol-4-yl)oxazole-4-carboxamide;

II-31: N-(1-((1 s,3s)-3-hydroxycyclobutyl)-3-(pyrazin-2-yl)-1H-pyrazol-4-yl)-2-(1H-pyrazol-4-yl)oxazole-4-carboxamide; or II-32: 2-(3-fluoro-1H-pyrazol-4-yl)-N-(1-((1r,4r)-4-morpholinocyclohexyl)-3-(pyrazin-2-yl)-1H-pyrazol-4-yl)oxazole-4-carboxamide.

Other exemplary compounds according to formula 1 may include:

III-1

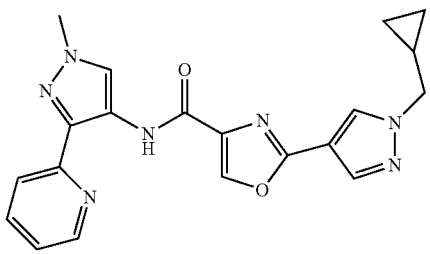

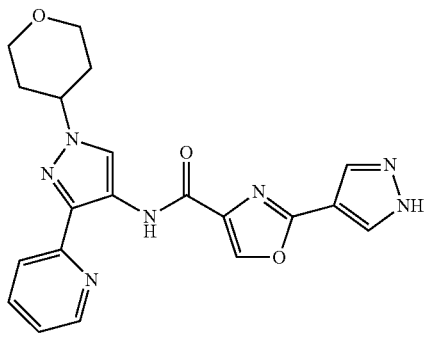
III-2

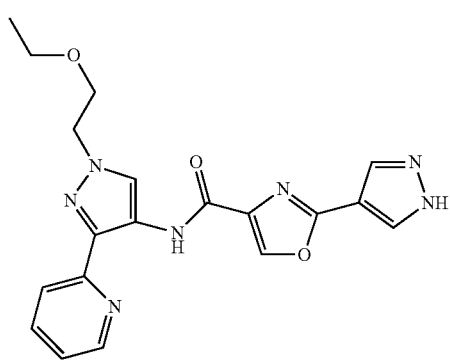
III-3

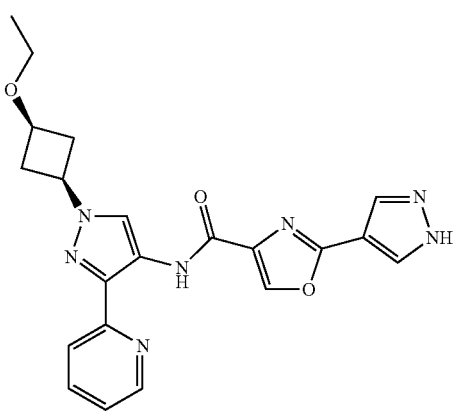
III-4

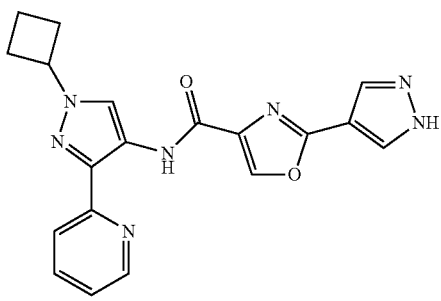
III-5

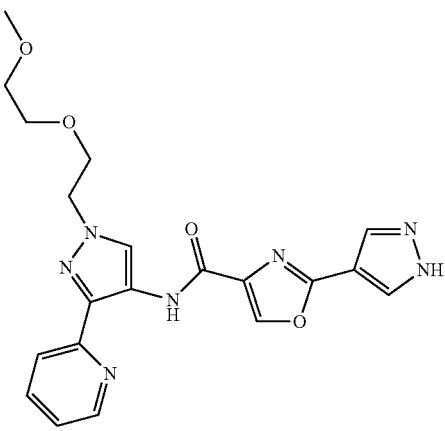
III-6

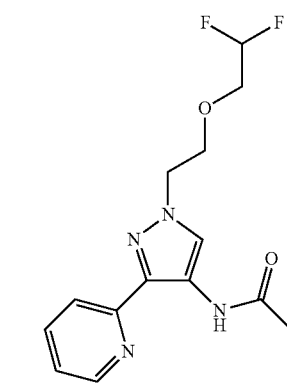
III-7

Additional exemplary compounds according to formula 1 may include:

III-1: 2-(1-(cyclopropylmethyl)-1H-pyrazol-4-yl)-N-(1-methyl-3-(pyridin-2-yl)-1H-pyrazol-4-yl)oxazole-4-carboxamide;

III-2: 2-(1H-pyrazol-4-yl)-N-(3-(pyridin-2-yl)-1-(tetrahydro-2H-pyran-4-yl)-1H-pyrazol-4-yl)oxazole-4-carboxamide;

III-3: N-(1-(2-ethoxyethyl)-3-(pyridin-2-yl)-1H-pyrazol-4-yl)-2-(1H-pyrazol-4-yl)oxazole-4-carboxamide;

III-4: N-(1-((1s,3s)-3-ethoxycyclobutyl)-3-(pyridin-2-yl)-1H-pyrazol-4-yl)-2-(1H-pyrazol-4-yl)oxazole-4-carboxamide;

III-5: N-(1-cyclobutyl-3-(pyridin-2-yl)-1H-pyrazol-4-yl)-2-(1H-pyrazol-4-yl)oxazole-4-carboxamide;

III-6: N-(1-(2-(2-methoxyethoxy)ethyl)-3-(pyridin-2-yl)-1H-pyrazol-4-yl)-2-(1H-pyrazol-4-yl)oxazole-4-carboxamide; or III-7: N-(1-(2-(2,2-difluoroethoxy)ethyl)-3-(pyridin-2-yl)-1H-pyrazol-4-yl)-2-(1H-pyrazol-4-yl)oxazole-4-carboxamide.

In some embodiments of formulas 1-12, the compound is not:

2-(1-(cyclopropylmethyl)-1H-pyrazol-4-yl)-N-(1-methyl-3-(pyridin-2-yl)-1H-pyrazol-4-yl)oxazole-4-carboxamide;

2-(1H-pyrazol-4-yl)-N-(3-(pyridin-2-yl)-1-(tetrahydro-2H-pyran-4-yl)-1H-pyrazol-4-yl)oxazole-4-carboxamide;

N-(1-(2-ethoxyethyl)-3-(pyridin-2-yl)-1H-pyrazol-4-yl)-2-(1H-pyrazol-4-yl)oxazole-4-carboxamide;

N-(1-((1s,3s)-3-ethoxycyclobutyl)-3-(pyridin-2-yl)-1H-pyrazol-4-yl)-2-(1H-pyrazol-4-yl)oxazole-4-carboxamide;

N-(1-cyclobutyl-3-(pyridin-2-yl)-1H-pyrazol-4-yl)-2-(1H-pyrazol-4-yl)oxazole-4-carboxamide;

N-(1-(2-(2-methoxyethoxy)ethyl)-3-(pyridin-2-yl)-1H-pyrazol-4-yl)-2-(1H-pyrazol-4-yl)oxazole-4-carboxamide;

N-(1-(2-(2,2-difluoroethoxy)ethyl)-3-(pyridin-2-yl)-1H-pyrazol-4-yl)-2-(1H-pyrazol-4-yl)oxazole-4-carboxamide;

N-(3-carbamoyl-1-(tetrahydro-2H-pyran-4-yl)-1H-pyrazol-4-yl)-2-(1H-pyrazol-4-yl)oxazole-4-carboxamide;

2-(1H-pyrazol-3-yl)-N-(3-(pyridin-2-yl)-1-(2-(2,2,2-trifluoroethoxy)ethyl)-1H-pyrazol-4-yl)oxazole-4-carboxamide; or N-(1-(2-(2-methoxyethoxy)ethyl)-3-(pyridin-2-yl)-1H-pyrazol-4-yl)-2-(1H-pyrazol-3-yl)oxazole-4-carboxamide.

B. Synthesis

Disclosed oxazole compounds can be prepared as exemplified below, and as will be understood by a person of ordinary skill in the art in organic synthesis. An exemplary synthesis may include the following 1$^{st}$ reaction step according to Scheme 1.

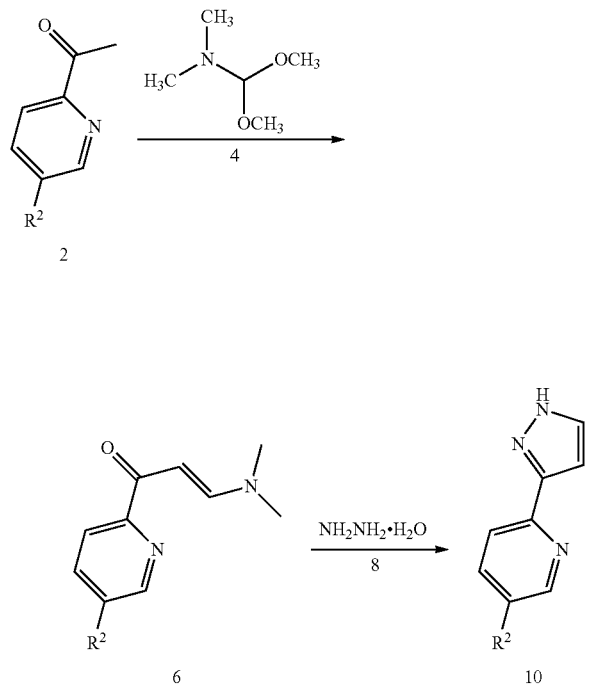

Acetyl compound 2 is reacted with dimethylformamide dimethylacetal 4 at a suitable reaction temperature, such as from about 85° C. to about 130° C., to form intermediate compound 6. Intermediate compound 6 is then reacted with hydrazine hydrate 8 to form pyrazole compound 10. The reaction is performed in a suitable solvent, for example, an alcohol such as ethanol, methanol or isopropanol, and is typically heated, such as to reflux.

A 2$^{nd}$ reaction step in the exemplary synthesis is provided below according to Scheme 2.

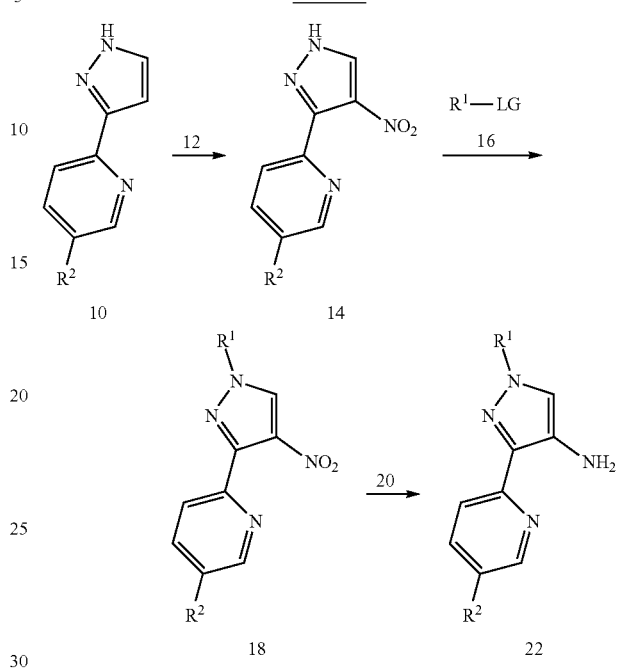

Compound 10 is nitrated using a suitable nitrating reagent or mixture of reagents 12 to form compound 14. Suitable nitrating conditions include reacting compound 10 with nitric acid, such as fuming nitric acid, optionally in the presence of sulfuric acid. Typically, compound 10 and the nitric acid are added slowly, one to the other. Cooling, such as by using an ice bath, may be used to maintain the reaction temperature within a suitable range, such as from about 0° C. to less than 50° C., from 0° C. to 20° C., or from 0 C to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from the aqueous and purified if required. Purification techniques suitable for purifying a product from any reaction disclosed herein include, but are not limited to, crystallization, distillation and/or chromatography.

With continued reference to Scheme 2, compound 14 is then reacted with compound 16 to form compound 18. Compound 16 comprises a desired R$^1$ moiety and a suitable leaving group, LG. Suitable leaving groups include any group that will act as a leaving group to facilitate the addition of the R$^1$ moiety to compound 14. Suitable leaving groups include, but are not limited to, halogens, typically bromo, chloro or iodo, and tosylate or mesylate groups. Compound 14 is reacted with compound 16 in a suitable solvent and typically in the presence of a base. Suitable solvents include any solvent that facilitates the reaction, such as aprotic solvents. Suitable solvents include, but are not limited to, DMF (dimethylformamide), THF (tetrahydrofuran), DMSO (dimethylsulfoxide), acetonitrile, chlorinated solvents such as dichloromethane and chloroform, DMA (dimethylacetamide), dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may proceed at room temperature, or the reaction mixture may be heated, such as to 50° C., 100° C. or higher, as required. Compound 18 is then isolated from the reaction mixture and purified if required.

Compound 18 is then reacted with a reducing agent 20 suitable to reduce the nitro moiety to an amine. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used in combination with a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 22 is isolated and purified if necessary.

A 3$^{rd}$ step of the exemplary reaction sequence is provided below according to Scheme 3.

Scheme 3

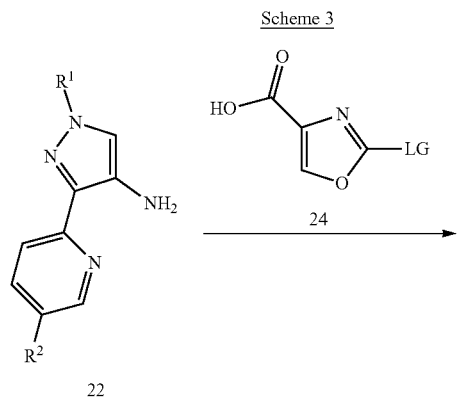

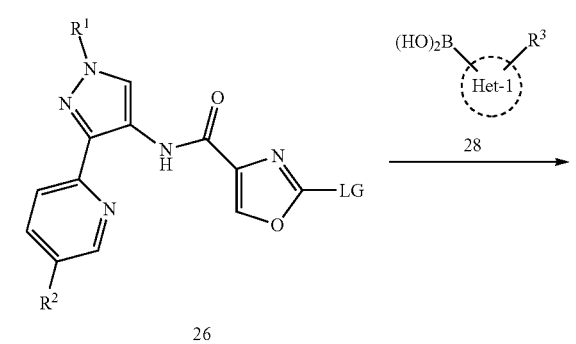

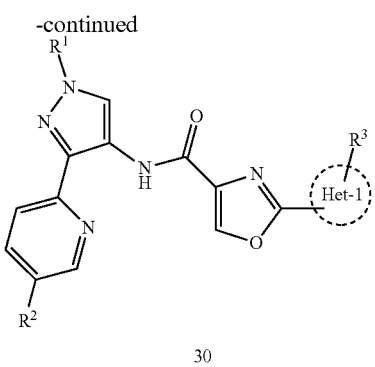

30

Compound 22 is reacted with a carboxylic acid 24 to form compound 26. The carboxylic acid 24 is activated by any suitable method and then reacted with the amine on compound 22. Suitable activation methods include, but are not limited to: forming the acid chloride, such as by treatment with thionyl chloride; treatment with 1-[Bis(dimethylamino)methylene]-1H-1,2,3-triazolo[4,5-b]pyridinium 3-oxid hexafluorophosphate (HATU) and a base such as diisopropylethylamine (DIPEA); treatment with carbonyldiimidazole (CDI); or treatment with a carbodiimide, such as dicyclohexylcarbodiimide (DCC) or 1-ethyl-3-(3-dimethylaminopropyl)carbodiimide (EDC).

Compound 26 is then coupled with compound 28 to form compound 30 using any coupling reaction suitable to form a bond between two rings. In the example of Scheme 3, a boronic acid coupling is shown using boronic acid 28, where the leaving group LG on compound 26 is typically bromo or iodo. Other suitable coupling functional groups include trialkyl tin or boronic esters. The coupling reaction typically proceeds in the presence of a suitable catalyst. For a boronic acid coupling, the catalyst typically is a palladium catalyst, such as PdCl$_2$(dppf)$_2$, Pd[P(Ph)$_3$]$_2$Cl$_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME (dimethoyethane)/ethanol/water. The reaction may be heated at a suitable temperature, such as to a temperature within the range of greater than room temperature up to the boiling point of the selected solvent, such as at a temperature of 50° C. to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 30 is then isolated from the reaction mixture and purified by a suitable technique.

An alternative exemplary synthesis may include the following 1$^{st}$ reaction step according to Scheme 4.

Scheme 4

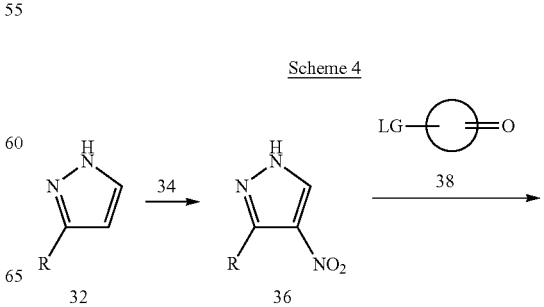

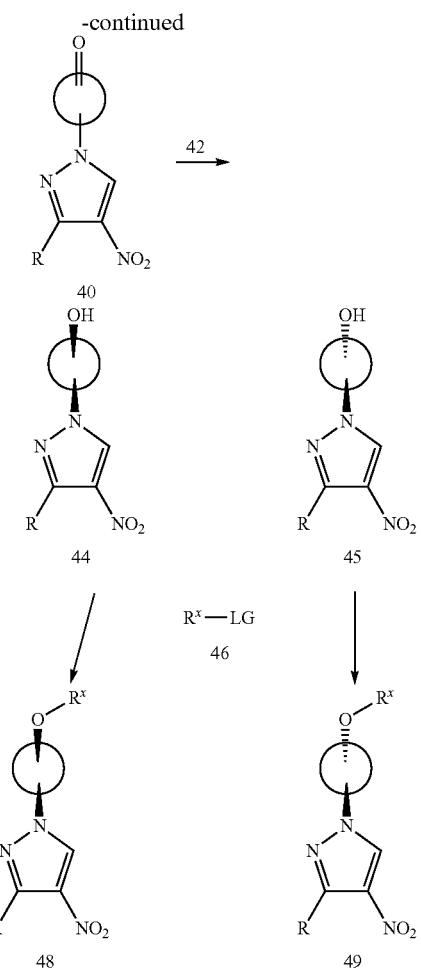

Compound 32 is nitrated using a suitable nitrating reagent or mixture of reagents 34 to form compound 36. Suitable nitrating conditions include reacting compound 32 with nitric acid, such as fuming nitric acid, optionally in the presence of sulfuric acid. Typically, compound 32 and the nitric acid are added slowly, one to the other. Cooling, such as by using an ice bath, may be used to maintain the reaction temperature within a suitable range, such as from about 0° C. to less than 50° C., from 0° C. to 20° C., or from 0 ° C to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from an aqueous phase and purified if required. Purification techniques suitable for purifying a product from any reaction disclosed herein include, but are not limited to, crystallization, distillation and/or chromatography.

With continued reference to Scheme 4, compound 36 is then reacted with compound 38 to form compound 40. Compound 38 comprises a desired ring, such as a cyclobutyl, cyclopentyl, or cyclohexyl ring, and a suitable leaving group, LG. Suitable leaving groups include any group that will act as a leaving group to facilitate the addition of the ring to compound 36. Suitable leaving groups include, but are not limited to, halogens, typically bromo, chloro or iodo, and tosylate or mesylate groups. Compound 36 is reacted with compound 38 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reaction, such as a hydride, typically sodium hydride, or a carbonate, such as potassium carbonate, sodium carbonate, or cesium carbonate. The reaction may proceed at room temperature, or the reaction mixture may be heated, such as to a temperature within the range of greater than room temperature up to the boiling point of the selected solvent, such as at 50° C., 100° C. or higher, as required. Compound 40 is then isolated from the reaction mixture and purified if required.

Compound 40 is then reacted with a reducing agent 42 suitable to reduce the carbonyl moiety to a hydroxyl group. Suitable reducing agents include, but are not limited to, sodium borohydride, di-isobutyl aluminum hydride, or lithium aluminum hydride. The reaction is performed in a solvent suitable to facilitate the reaction, such as an alcohol, particularly methanol or ethanol, THF, or diethyl ether. The reaction may proceed at room temperature, or the reaction mixture may be heated, such as to a temperature of greater than room temperature up to the boiling point of the selected solvent, such as a temperature of 50° C., 100° C. or higher. Alternatively, the reaction mixture may be cooled as required, such as to below 20° C., below 10° C., or below 0° C. Once the reaction is complete, as indicated by an analytical technique such as LC-MS, TLC or HPLC, the product compound 44 is isolated and purified if necessary, by a suitable technique, such as column chromatography. Alternatively, or additionally, compound 45 may isolated.

Optionally, compound 44, and/or compound 45, may be reacted with compound 46 to form compound 48 and/or compound 49. Compound 46 comprises a desired RX moiety and a suitable leaving group, LG. Suitable leaving groups include any group that will act as a leaving group to facilitate the addition of the RX moiety to compound 44 and/or compound 45. Suitable leaving groups include, but are not limited to, halogens, typically bromo, chloro or iodo, and tosylate or mesylate groups. Compound 44/45 is reacted with compound 46 in a suitable solvent and typically in the presence of a base or other reagent or reagents that facilitate the reaction. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases or reagents that facilitate the reaction include, but are not limited to, silver triflate, 2,6-di-t-butylpyridine, sodium hydride, or combinations thereof. Typically, compound 46 is slowly added to the reaction mixture. Cooling, such as by an ice bath, may be used to maintain the reaction temperature within a suitable range, such as from about 0° C. to less than 50° C., from 0° C. to 20° C., or from 0 ° C to 10° C. After the addition of 46 is complete the reaction is allowed to proceed until the reaction is substantially complete, and may be allowed to warm to room temperature, or the reaction may be heated to a temperature within the range of greater than room temperature up to the boiling point of the selected solvent, such as 50° C., 100° C. or higher, to facilitate the reaction. Once the reaction is complete, as may be indicated by an analytical technique such as LC-MS, TLC or HPLC, the product compound 48 and/or compound 49 is isolated and purified if necessary, by a suitable technique, such as column chromatography.

Another exemplary synthetic route to compound 48 and/or compound 49 is illustrated in Scheme 5.

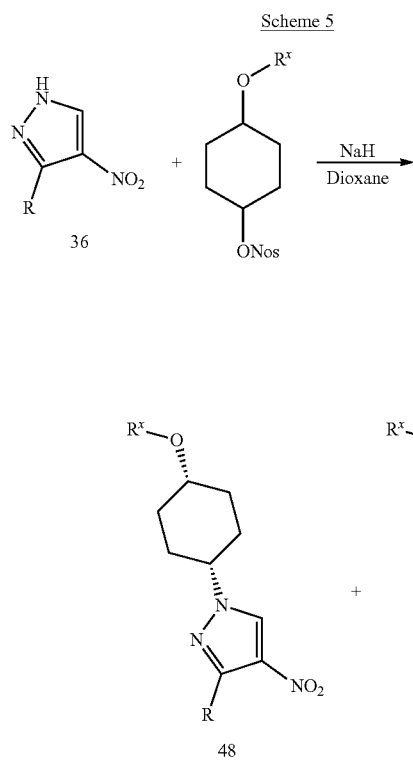

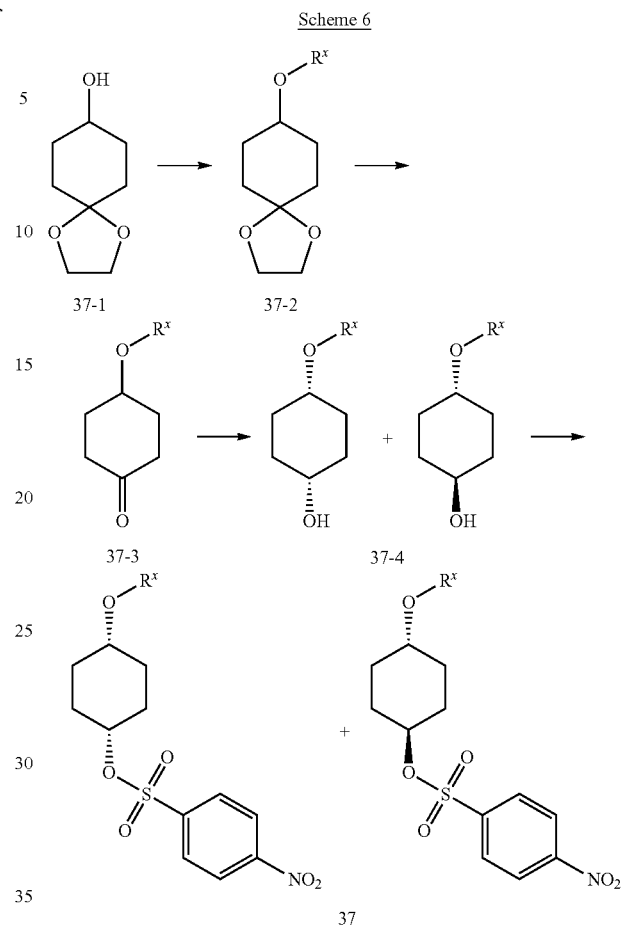

With reference to Scheme 5, compound 36 is dissolved in a suitable solvent with cooling, and treated with a base, such as sodium hydride. Suitable solvents include, but are not limited to, aprotic solvents, such as 1,4-dioxane, THF, DMF, acetonitrile, ether, or a combination thereof. Cyclohexyl compound 37 having a 4-nitrobenzenesulfone leaving group (nosyl, or Nos) is added and the reaction is heated at a temperature suitable to facilitate a reaction, such as at a temperature within a temperature range of greater than room temperature up to the boiling point of the selected solvent, such as from 50° C. to 200° C. or higher, typically from 90° C. to 150° C. The reaction may be agitated, such as by shaking or stirring. Additional compound 37 may be added if necessary, to facilitate the reaction proceeding to completion.

The reaction mixture is quenched, such as by the addition of sodium bicarbonate solution, and the products are extracted into an organic solvent, such as ethyl acetate or chloroform. The compounds 48 and 49 can be separated and/or purified by any suitable technique, or combination of techniques, such as chromatography or trituration. 4-Nitrobenzensulfonate compound 37 may be prepared according to an exemplary synthetic route according to Scheme 6

With reference to Scheme 6, 1,4-dioxaspiro[4.5]decan-8-ol 37-1 is treated first with a base, such as sodium hydride or potassium tert-butoxide, in a suitable solvent, and then with $R^x$-LG to form compound 37-2, where LG is a suitable leaving group, such as chloride, bromide, iodide, tosylate or mesylate. Suitable solvents include, but are not limited to, aprotic solvents, such as THF, DMF, acetonitrile, dioxane, ether, or a combination thereof. After the reaction has proceeded substantially to completion, aqueous acid, such as HCl, is added to quench the reaction and form compound 37-3.

Compound 37-3 is then treated with a reducing agent to form compound 37-4. Compound 37-4 may be substantially one isomer, or alternatively, compound 37-4 may be a mixture of cis and trans isomers, and in some embodiments, the compound 37-4 comprises about a 2:1 mixture of cis:trans isomers. The reducing agent may be any agent that can reduce the carbonyl moiety to an alcohol moiety. Suitable reducing agents include, but are not limited to, lithium aluminum hydride, diisobutylaluminum hydride, borane-THF, or a borohydride reagent, such as sodium borohydride. Solvents suitable to facilitate the reaction include, but are not limited to, THF, ether, or a combination thereof.

Compound 37-4 is then treated with 4-nitrobenzenesulfonyl chloride (nosyl) in the presence of a base, to form compound 37. The base may be any suitable base that facilitates the reaction, and may be an organic base, such as trimethylamine, 1,4-diazabicyclo[2.2.2]octane (DABCO), pyridine, or Hunig's base; or an inorganic base, such as potassium carbonate, sodium carbonate, or cesium carbonate. The reaction may proceed in a suitable solvent, typically an aprotic solvent such as pyridine, THF or a chlorinated solvent, such as dichloromethane or chloroform. Compound 37 may be substantially one isomer, or alternatively, compound 37 may be a mixture of isomers. The ratio of isomers may be modified by a suitable technique, such as chromatography or trituration. In some embodiments, the ratio of isomers is purified to about 8:1 cis to trans by trituration.

Alternatively, compound 40 may be prepared by an exemplary synthetic route according to Scheme 7.

Compound 52 is then reacted with a suitable reagent 54 to form compound 40. Reagent 54 may be any reagent suitable to remove the protecting group and/or form the carbonyl moiety. In the exemplary synthesis shown in Scheme 5, the protecting group is a cyclic ketal, and suitable reagents 54 include, but are not limited to, pyridinium tosylate (PPTS), para-toluene sulfonic acid, hydrochloric acid, or acetic acid. The reaction is performed in a solvent or mixture of solvents suitable to facilitate the reaction, such as acetone, THF, acetic acid, water, or a combination thereof. The reaction may proceed at room temperature, or alternatively the reaction mixture may be heated, such as at a temperature within the range of greater than room temperature up to the boiling point of the selected solvent, such as 50° C., 100° C. or higher, as required. Compound 40 is then isolated from the reaction mixture and purified if required by a suitable technique, such as column chromatography.

A $2^{nd}$ step of the exemplary reaction sequence is provided below according to Scheme 8.

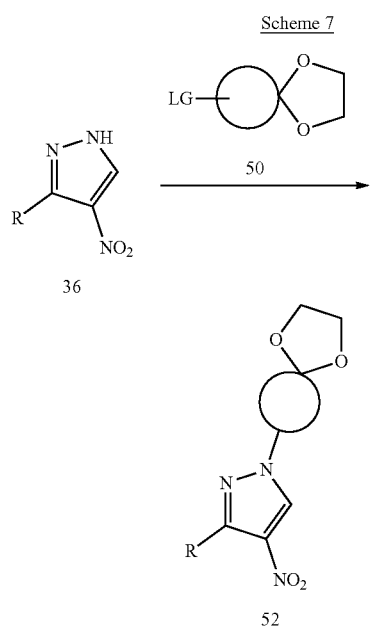

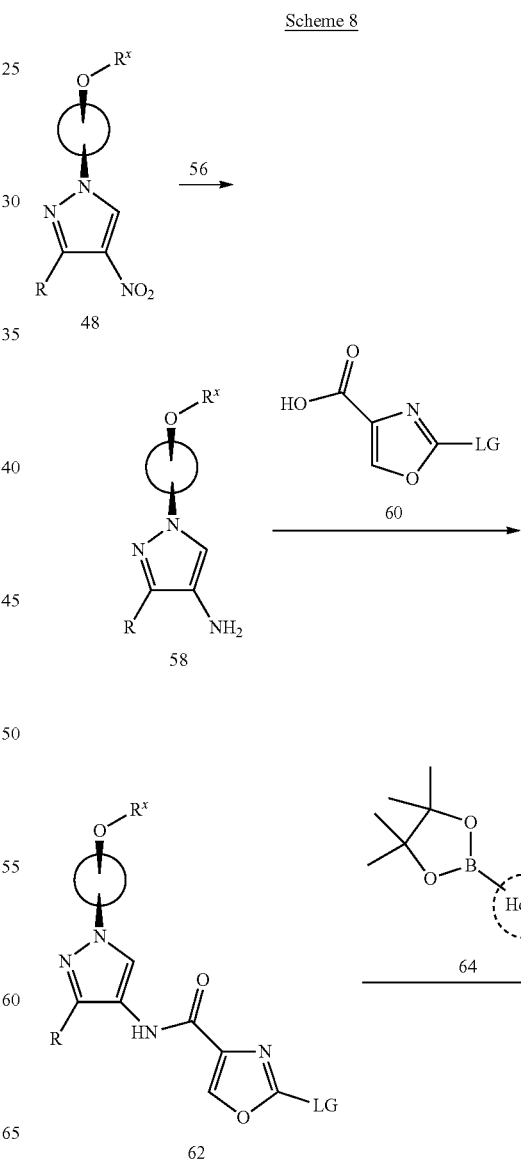

With respect to Scheme 7, compound 36 is reacted with compound 50 to form compound 52. Compound 50 comprises a desired ring, such as a cyclobutyl, cyclopentyl, or cyclohexyl ring, a suitable leaving group, LG, and a protected carbonyl moiety, such as an acetal or a ketal. In the example above a cyclic ketal moiety is shown. Suitable leaving groups include any group that will act as a leaving group to facilitate the addition of the ring to compound 36, and include, but are not limited to, halogens, typically bromo, chloro or iodo, and tosylate or mesylate groups. Compound 36 is reacted with compound 50 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may proceed at room temperature or alternatively the reaction mixture may be heated, such as at a temperature within the range of greater than room temperature up to the boiling point of the selected solvent, such as 50° C., 100° C. or higher, as required. Compound 52 is then isolated from the reaction mixture and purified if required by a suitable technique, such as column chromatography.

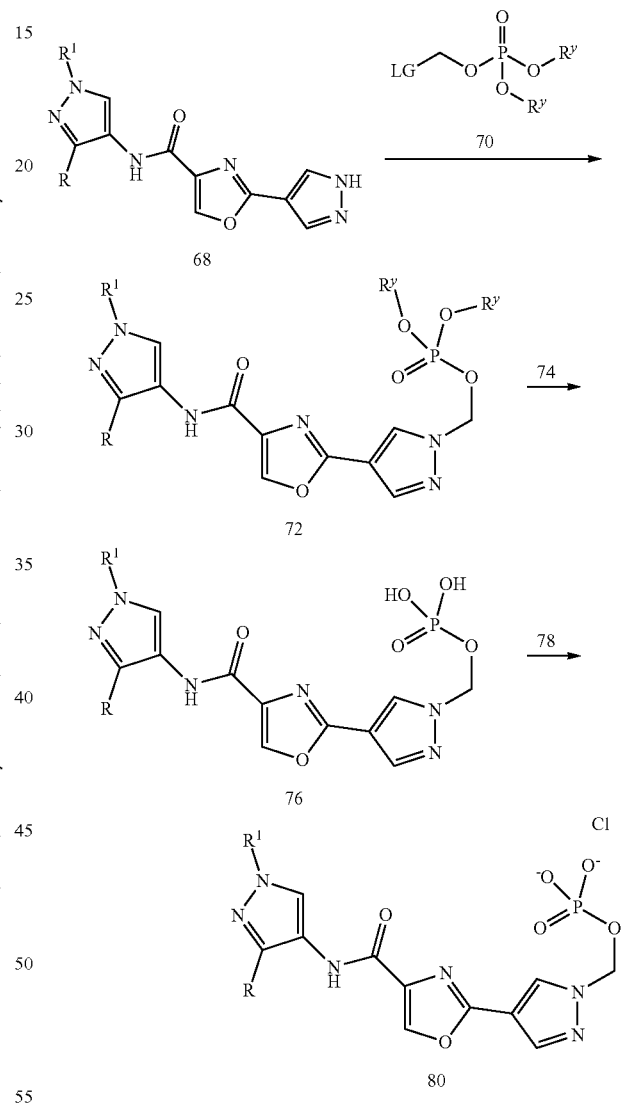

Compound 48 is reacted with a reducing agent 56 suitable to reduce the nitro moiety to an amine. In certain embodiments where the desired product compound comprises a hydroxyl moiety, compound 44 may be used in place of compound 48. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used, in the presence of a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 58 is isolated and purified if necessary.

Compound 58 is reacted with a carboxylic acid 60 to form amide 62. The carboxylic acid 60 is activated by any suitable method and then reacted with the amine functional group of compound 58. Suitable activation methods include, but are not limited to: forming the acid chloride by treatment with thionyl chloride; treatment with 1-[Bis(dimethylamino)methylene]-1H-1,2,3-triazolo[4,5-b]pyridinium 3-oxid hexafluorophosphate (HATU) and a base such as diisopropylethylamine (DIPEA); by treatment with carbonyldiimidazole (CDI); or treatment with a carbodiimide, such as dicyclohexylcarbodiimide (DCC) or 1-Ethyl-3-(3-dimethylaminopropyl)carbodiimide (EDC).

Compound 62 is then coupled with compound 64 to form compound 66 using any coupling reaction suitable to form a bond between two rings. In the example above, a boronic ester coupling is shown, where the leaving group LG on compound 62 is typically bromo or iodo. Other suitable coupling functional groups include trialkyl tin or boronic acids. The coupling reaction typically proceeds in the presence of a suitable catalyst. For a boronic ester or boronic acid coupling, the catalyst typically is a palladium catalyst, such as $PdCl_2(dppf)_2$, $Pd[P(Ph)_3]_2Cl_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME/ethanol/water. The reaction may be heated at a suitable temperature, such as from 50° C. to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 66 is then isolated from the reaction mixture and purified by a suitable technique.

Certain embodiments may comprise a phosphate moiety. Scheme 9 provides an exemplary synthesis of certain such embodiments.

Compound 68 is reacted with compound 70 to form compound 72. Compound 70 comprises desired $R^y$ moieties and a suitable leaving group, LG. Typical $R^y$ moieties include, but are not limited to aliphatic, such as alkyl, typically methyl, ethyl, propyl, isopropyl or t-butyl; aryl; heteroaliphatic; or heterocyclic. The two $R^y$ moieties may be the same or different. Suitable leaving groups include, but are not limited to, halogens, typically bromo, chloro or iodo, and tosylate or mesylate groups. Compound 68 is reacted with compound 70 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may proceed at room temperature, or alternatively the reaction mixture may be heated, such as at a temperature within the range of greater than room temperature up to the boiling point of the selected solvent, such as 50° C., 100° C. or higher, as required. Compound 72 is then isolated from the reaction mixture and purified if required.

Compound 72 is then reacted with compound 74 to form compound 76. Compound 74 may be any compound suitable to form the acid moieties in compound 76. Compound 74 may be an acidic reagent, such as trifluoroacetic acid, hydrochloride acid, or hydrobromic acid, or it may be a basic reagent, such as sodium hydroxide, lithium hydroxide or potassium hydroxide. Suitable solvents include, but are not limited to, chlorinated solvents such as dichloromethane and chloroform, alcohols such as methanol and ethanol, water, or combinations thereof. The reaction may proceed at room temperature, or alternatively the reaction mixture may be heated, such as at a temperature within the range of greater than room temperature up to the boiling point of the selected solvent, such as 50° C., 100° C. or higher, as required. The reaction mixture also may be cooled, such as to below 20° C., below 10° C., below 0° C. or lower. Once the reaction is complete, as indicated by an analytical technique such as LC-MS, TLC or HPLC, the product compound 76 is isolated and purified if necessary, by a suitable technique, such as by agitating, such as by stirring or sonication, in a suitable solvent or solvent system. Suitable solvents or solvent systems include, but are not limited to, acetone/water, acetone, diethyl ether, or alcohol/water.

Compound 76 is then reacted with compound 78 to form the salt compound 80. Compound 78 can be any compound that will provide a suitable counterion (CI) for the salt compound 80, such as calcium hydroxide, sodium hydroxide, potassium hydroxide, lithium hydroxide, ammonia, trimethylamine, tris(hydroxymethyl)aminomethane, or an amino acid such as lysine or arginine. A person of ordinary skill in the art will appreciate that if counter ion CI has a single positive charge, as in Na$^+$, K$^+$, Li$^+$, or NH$_4^+$, then compound 80 will comprise two CI ions, whereas if counter ion CI has two positive charges, as in CI$^{2+}$ compound 80 will comprise one CI ion.

C. Combinations of Therapeutic Agents

The oxazole compounds of the present invention may be used alone, in combination with one another, or as an adjunct to, or in combination with, other established therapies. In another aspect, the compounds of the present invention may be used in combination with other therapeutic agents useful for a particular disorder or condition being treated. These compounds may be administered simultaneously, sequentially in any order, by the same route of administration, or by a different route.

In some embodiments, the second therapeutic agent is an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a non-steroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with other anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an antineoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhbitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present oxazole compounds include proteasome inhibitors, such as bortezomib, carfilzomib, marizomib and the like.

Examples of kinase inhibitors that are useful in combination with the presently disclosed compounds, particularly in treating malignancies include, Btk inhibitors, such as ibrutinib, CDK inhibitors, such as palbociclib, EGFR inhibitors, such as afatinib, erlotinib, gefitinib, lapatinib, osimertinib and vandetinib, Mek inhibitors, such as trametinib, Raf inhibitors, such as dabrafenib, sorafenib and vemurafenib, VEGFR inhibitors, such as axitinib, lenvatinib, nintedanib, pazopanib, BCR-Abl inhibitors, such as bosutinib, dasatinib, imatinib and nilotinib, Syk inhibitors, such as fostamatinib, and JAK inhibitors, such as ruxolitinib, In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides) e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues—for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

D. Compositions Comprising Oxazole Compounds

The disclosed oxazole compounds may be used alone, in any combination, and in combination with, or adjunctive to, at least one second therapeutic agent, and further the oxazole compounds, and the at least one second therapeutic, may be used in combination with any suitable additive useful for forming compositions for administration to a subject. Additives can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. Typical additives include, by way of example and without limitation: pharmaceutically acceptable excipients; pharmaceutically acceptable carriers; and/or adjuvants, such as mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; antiadherents, such as magnesium stearate; binders, such as saccharides (including disaccharides, such as sucrose and lactose,), polysaccharides (such as starches, cellulose, microcrystalline cellulose, cellulose ethers (such as hydroxypropyl cellulose), gelatin, synthetic polymers (such as polyvinylpyrrolidone, polyalkylene gylcols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

III. Methods of Use

A. Diseases/Disorders

The disclosed oxazole compounds, as well as combinations and/or compositions thereof, may be used to ameliorate, treat or prevent a variety of diseases and/or disorders. In particular embodiments, the oxazole compound, combinations of oxazole compounds, or compositions thereof, may be useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3 or IRAK4. In certain embodiments, disclosed oxazole compounds are useful for treating, preventing or ameliorating auto-immune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, and bacterial and viral infections.

In some embodiments, the oxazole compound, combinations of oxazole compounds, or compositions thereof, may be used to treat or prevent allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy or asthma.

The oxazole compound, combinations of oxazole compounds, or compositions thereof, may also be useful for ameliorating, treating or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracts, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the oxazole compound, combinations of oxazole compounds, or compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Cronh's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, Parkinson's disease.

Proliferative diseases that may be treated by the oxazole compound, combinations of oxazole compounds, or compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the oxazole compound, combinations of oxazole compounds, or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The oxazole compound, combinations of oxazole compounds, or compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising one or more active oxazole compounds of the invention (or prodrugs thereof) may be manufactured by mixing, dissolving, granulating, dragee-making, levigating, emulsifying, encapsulating, entrapping or lyophilization processes. The compositions may be formulated using one or more physiologically acceptable excipients, diluents, carriers, adjuvants or auxiliaries to provide preparations which can be used pharmaceutically.

The active compound(s) or prodrug(s) may be formulated in the pharmaceutical compositions per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), hydrate, solvate, N-oxide or pharmaceutically acceptable salt or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, pharmaceutically acceptable salt or prodrug(s) can be conveniently delivered in the form of an aerosol spray from pressurized packs or a nebulizer with the use of a suitable propellant, e.g.,) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (1 4 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL of the oxazole compound(s) or prodrug(s), 1% (v/v) polysorbate 80 (TWEEN® 80), 50 mM citrate and/or 0.9% sodium chloride.

For ocular administration, the active oxazole compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active oxazole compound(s) or prodrug(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s) or prodrug(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The oxazole compound or combinations of oxazole compounds will generally be used in an amount effective to achieve the intended result, for example, in an amount effective to treat, prevent or ameliorate a particular condition. The oxazole compound(s), or compositions thereof, can be administered therapeutically to achieve therapeutic benefit or prophylactically to achieve a prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of oxazole compounds may depend on various factors, including the age, weight, general health, and severity of the condition of the patient or subject being treated. Dosage may also may need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the oxazole compound(s) or compositions thereof, will also depend on whether the oxazole compound(s) are formulated for treatment of acute episodes of a condition or for the prophylactic treatment of a disorder. A person or ordinary skill in the art will be able to determine the optimal dose for a particular individual.

For prophylactic administration, the oxazole compound, combinations of oxazole compounds, or compositions thereof, can be administered to a patient or subject at risk of developing one of the previously described conditions. For example, if it is unknown whether a patient or subject is allergic to a particular drug, the oxazole compound, combinations of oxazole compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, an oxazole compound(s), or composition thereof, can be administered to an allergy sufferer prior to expected exposure to the allergen. An oxazole compound, combinations of oxazole compounds, or compositions thereof, can also be administered prophylactically to healthy individuals who are repeatedly exposed to agents known to one of the above-described maladies to prevent the onset of the disorder. For example, an oxazole compound, combinations of oxazole compounds, or compositions thereof, can be administered to a healthy individual who is repeatedly exposed to an allergen known to induce allergies, such as latex, in an effort to prevent the individual from developing an allergy. Alternatively, an oxazole compound, combinations of oxazole compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, from greater than 0 to 0.1 µM, from greater than 0 to 0.01 µM, such as from greater than zero to 0.004 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed oxazole compounds will typically be in the range of from greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the oxazole compound, its bioavailability, the mode of administration, and various factors discussed above.

Dosage amount and dosage interval can be adjusted for individuals to provide plasma levels of the oxazole compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed oxazole compounds typically comprise from greater than 0 up to 99% of the oxazole compound, or compounds, and/or other therapeutic agent by total weight percent. More typically, compositions comprising one or more of the disclosed oxazole compounds comprise from about 1 to about 20 total weight percent of the oxazole compound and other therapeutic agent, and from about 80 to about 99 weight percent of a pharmaceutically acceptable additive.

Preferably, the oxazole compound, combinations of oxazole compounds, or compositions thereof, will provide therapeutic or prophylactic benefit without causing substantial toxicity. Toxicity of the oxazole compound can be determined using standard pharmaceutical procedures. The dose ratio between toxic and therapeutic (or prophylactic) effect is the therapeutic index. Oxazole compounds that exhibit high therapeutic indices are preferred.

IV. Examples

Example 1

Preparation of 3-fluoro-2-(1H-pyrazol-3-yl)-6-(trifluoromethyl)pyridine 102

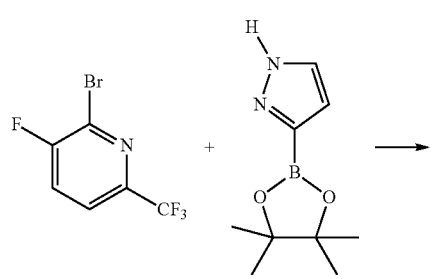

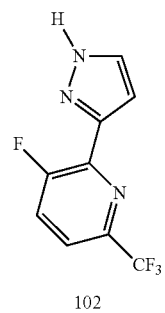

102

A round bottom flask was charged with 2-bromo-3-fluoro-6-(trifluoromethyl)pyridine (20.7 g, 84.7 mM), 3-(4,4,5,5-tetramethyl-1,3,2-dioxaborolan-2-yl)-1H-pyrazole (32.8 g, 169 mM) and Pd(Ph3)4 (9.79 g, 8.47 mM). $Na_2CO_3$ (44.9 g, 423 mM) was dissolved in $H_2O$ (200 ml) and added to the reaction flask together with dioxane (500 ml). The reaction mixture was heated at 100° C. for 4 hours; during this time the reaction turned into a yellow suspension. Analysis by TLC and LCMS indicated complete conversion; solvents were removed under reduced pressure using a rotary evaporator. Water (400 ml) was added to the crude product and the mixture was extracted with EtOAc (3×200 ml). The combined organic phases were filtered through $Na_2SO_4$ and silica gel was added to the filtrate. The mixture was concentrated to dryness adsorbing the crude product onto silica gel. CombiFlash chromatography eluting with DCM/MeOH—$NH_3$ (2 M) (gradient 0 to 2%) resulted in 18.4 g (94% yield) of the title compound 3-fluoro-2-(1H-pyrazol-3-yl)-6-(trifluoromethyl)pyridine 102 in form of an off-white solid.

$^1$H NMR (400 MHz, $CDCl_3$) δ 8.39 (s, 1H), 7.90 (dd, J=8.6, 3.6 Hz, 1H), 7.77 (t, J=8.8 Hz, 1H); MS (ESI) (m/z): 232 $[M+H]^+$.

Example 2

Preparation of 3-fluoro-2-(4-nitro-1H-pyrazol-3-yl)-6-(trifluoromethyl) pyridine 104

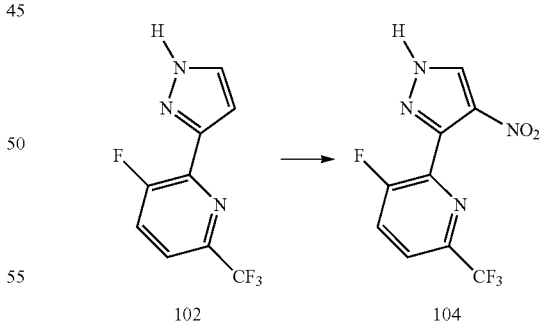

102          104

3-Fluoro-2-(1H-pyrazol-3-yl)-6-(trifluoromethyl)pyridine 102 (18.4 g, 79.6 mM) was dissolved in concentrated $H_2SO_4$ (90 ml) and cooled to 0° C. Fuming $HNO_3$ (17 ml, 398 mM) was added dropwise using a dropping funnel. The reaction mixture was allowed to warm to room temperature overnight. The mixture was then slowly poured on crushed ice and neutralized using a saturated aqueous NaOH solution while maintaining ice-bath cooling throughout the addition. When the mixture approached pH 5-6 a large amount of solid started to precipitate. The pH was adjusted to about 7 and the mixture was then extracted with EtOAc (2×300 ml). The pooled organic layers were filtered through Na₂SO₄, silica gel was added and the solvent was removed under reduced pressure. The resulting material was loaded onto a CombiFlash column and further purified eluting with Hexane/EtOAc (gradient 0 to 100%). The desired product was obtained in form of a white solid (20.6 g, 94% yield).

¹H NMR (400 MHz, CDCl₃) δ 10.39 (s, 1H), 7.75 (d, J=2.0 Hz, 1H), 7.66 (d, J=2.3 Hz, 1H), 7.65 (s, 1H), 6.99 (s, 1H); MS (ESI) (m/z): 277 [M+H]⁺.

Example 3

Preparation of 3-fluoro-2-(4-nitro-1-(1,4-dioxaspiro [4.5]decan-8-yl)-1H-pyrazol-3-yl)-6-(trifluoromethyl)pyridine 106

¹H NMR (400 MHz, CDCl₃) δ 8.32 (d, J=0.4 Hz, 1H), 7.82 (dd, J=8.6, 3.6 Hz, 1H), 7.68 (td, J=8.4, 0.7 Hz, 1H), 4.32 (tt, J=11.6, 4.0 Hz, 1H), 3.98-3.92 (m, 4H), 2.24 (dddd, J=10.2, 4.2, 2.8, 1.6 Hz, 2H), 2.11 (tdd, J=12.9, 11.5, 3.9 Hz, 2H), 1.95-1.84 (m, 2H), 1.72 (td, J=13.3, 4.3 Hz, 2H); MS (ESI) (m/z): 417 [M+H]⁺.

Example 4

Preparation of 4-(3-(3-fluoro-6-(trifluoromethyl) pyridin-2-yl)-4-nitro-1H-pyrazol-1-yl)cyclohexan-1-one 108

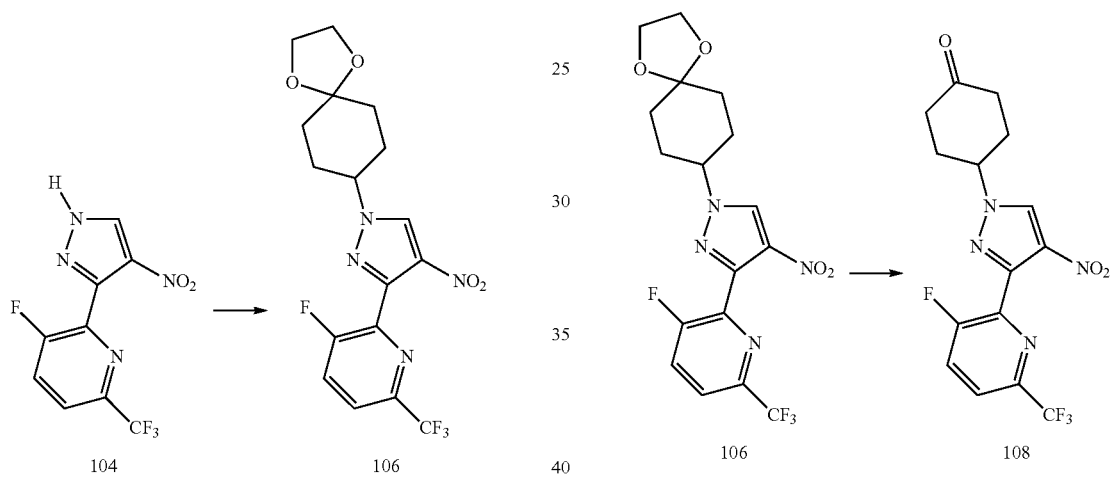

A two-neck round bottom flask was charged with 3-fluoro-2-(4-nitro-1H-pyrazol-3-yl)-6-(trifluoromethyl) pyridine 104 (20.6 g, 74.6 mM). Anhydrous dioxane (500 ml) was added and the mixture was stirred until it became a clear solution. The reaction flask was degassed and backfilled with nitrogen. Subsequently, NaH (in mineral oil, 60 wt %) (4.47 g, 111.9 mM) was slowly added in portions at room temperature and the greyish suspension was stirred for about 10 minutes. 1,4-dioxaspiro[4.5]decan-8-yl 4-methylbenzenesulfonate (69.9 g, 224 mM) was added portion wise and reaction mixture was refluxed for two days. After cooling down to room temperature, the reaction was quenched with MeOH (100 ml) and the solvents were removed under reduced pressure. Water (300 ml) was added to the crude product and the mixture was extracted with EtOAc (2×300 ml). The organic layers were filtered through Na₂SO₄ and the crude product was adsorbed on silica gel. The desired product 106 (off-white solid, 18.3 g, 59% yield) was isolated by flash chromatography eluting with Hexane/EtOAc (gradient 0 to 30%).

3-fluoro-2-(4-nitro-1-(1,4-dioxaspiro[4.5]decan-8-yl)-1H-pyrazol-3-yl)-6-(trifluoromethyl)pyridine 106 (18.0 g, 43.2 mM) was dissolved in acetone (400 ml), then water (100 ml) and p-toluenesulfonic acid monohydrate (20.6 g, 108 mM) were added. The mixture was heated at 80° C. for 6 hours. The acetone was removed under reduced pressure and a saturated aqueous solution of NaHCO₃ (200 ml) was added. The aqueous phase was extracted with EtOAc (2×300 ml) and the combined organic layers were dried over Na₂SO₄. The crude product was further purified by flash chromatography eluting with Hexane/EtOAc (gradient 0 to 50%). The title compound 108 was obtained as an off-white solid (12.5 g, 78% yield).

¹H NMR (400 MHz, CDCl₃) δ 8.36 (d, J=0.4 Hz, 1H), 7.86 (dd, J=8.6, 3.6 Hz, 1H), 7.71 (td, J=8.4, 0.7 Hz, 1H), 4.75 (tt, J=10.8, 3.5 Hz, 1H), 2.73-2.47 (m, 7H), 2.45-2.27 (m, 2H); MS (ESI) (m/z): 373 [M+H]⁺.

Example 5

Preparation of 4-((1r,4r)-4-(3-(3-fluoro-6-(trifluoromethyl)pyridin-2-yl)-4-nitro-1H-pyrazol-1-yl)cyclohexyl)morpholine 110

Example 6

Preparation of 3-(3-fluoro-6-(trifluoromethyl)pyridin-2-yl)-1-((1r,4r)-4-morpholinocyclohexyl)-1H-pyrazol-4-amine 112

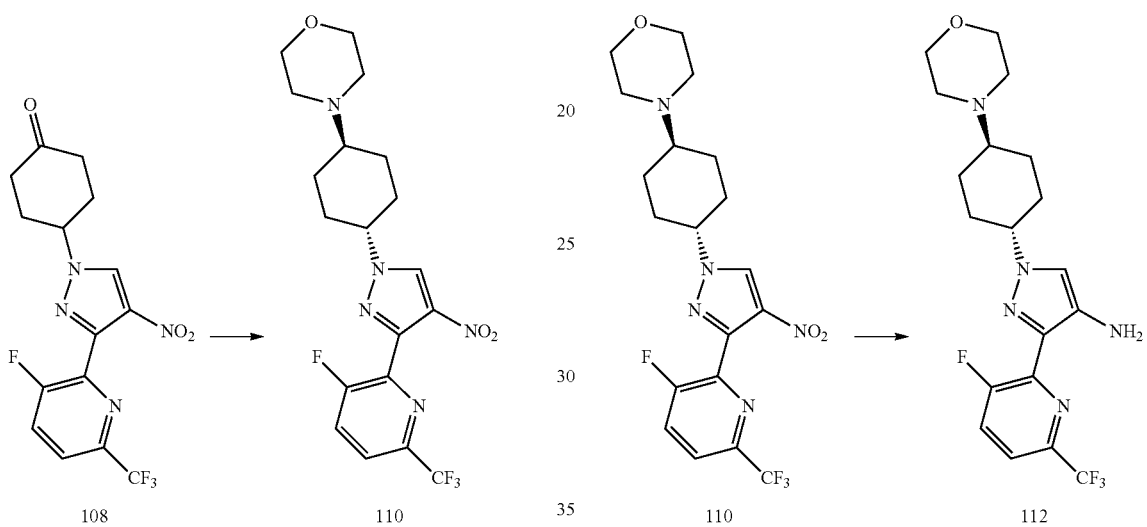

The ketone 108 (12.5 g, 33.6 mM) from Example 4 was dissolved in dry DCM (500 ml) and morpholine (35 ml, 402 mM) was added. NaBH(OAc)$_3$ (14.2 g, 67.2 mM) was added and the yellowish suspension was stirred for 3 days. A saturated aqueous solution of (400 ml) was added and the mixture was extracted with DCM (2×300 ml). The organic layers were filtered through Na$_2$SO$_4$ and solvents were removed under reduced pressure. The crude product was purified by CombiFlash chromatography eluting with DCM/MeOH—NH$_3$ (2 M) (gradient 0 to 2%) furnishing 3.86 g (26% yield) of the title compound 110 in form of an off-white solid.

The nitro compound 110 (3.22 g, 7.79 mM) from Example 5 was dissolved in EtOAc (100 ml) and placed in a Parr pressure vessel together with Pd/C (wet support, loading 10 wt %, Degussa type E101 NE/W, 644 mg). The mixture was degassed and backfilled with hydrogen three times. The reaction mixture was kept under 60 psi hydrogen pressure using a Parr shaker hydrogenation apparatus. After 3 hours, the reduction was complete and the catalyst was filtered off using a frit charged with Celite. Evaporation of the solvent under reduced pressure provided the desired product 112 (2.94 g, 91% yield) as a tan solid.

$^1$H NMR (400 MHz, CDCl$_3$) δ 8.29 (d, J=0.4 Hz, 1H), 7.84 (dd, J=8.6, 3.6 Hz, 1H), 7.69 (td, J=8.4, 0.7 Hz, 1H), 4.23 (tt, J=12.0, 3.9 Hz, 1H), 3.82-3.62 (m, 4H), 2.59 (dd, J=6.5, 3.0 Hz, 4H), 2.48-2.27 (m, 3H), 2.16 (dq, J=12.8, 3.5 Hz, 2H), 1.95-1.75 (m, 3H), 1.46 (qd, J=13.2, 3.4 Hz, 2H); MS (ESI) (m/z): 444 [M+H]$^+$.

$^1$H NMR (400 MHz, DMSO-d$_6$) δ 7.97 (ddd, J=10.8, 8.5, 0.8 Hz, 1H), 7.78 (dd, J=8.5, 3.1 Hz, 1H), 4.96 (s, 2H), 4.06 (tt, J=11.9, 4.0 Hz, 1H), 3.63-3.47 (m, 4H), 2.47 (ddt, J=9.3, 4.7, 2.4 Hz, 4H), 2.27 (tt, J=11.6, 3.5 Hz, 1H), 2.09-1.99 (m, 2H), 1.95-1.86 (m, 2H), 1.80-1.66 (m, 2H), 1.37 (tdd, J=13.8, 11.8, 3.4 Hz, 2H); MS (ESI) (m/z): 414 [M+H]$^+$.

Example 7

Preparation of 2-chloro-N-(3-(3-fluoro-6-(trifluoromethyl)pyridin-2-yl)-1-((1r,4r)-4-morpholinocyclohexyl)-1H-pyrazol-4-yl)oxazole-4-carboxamide 114

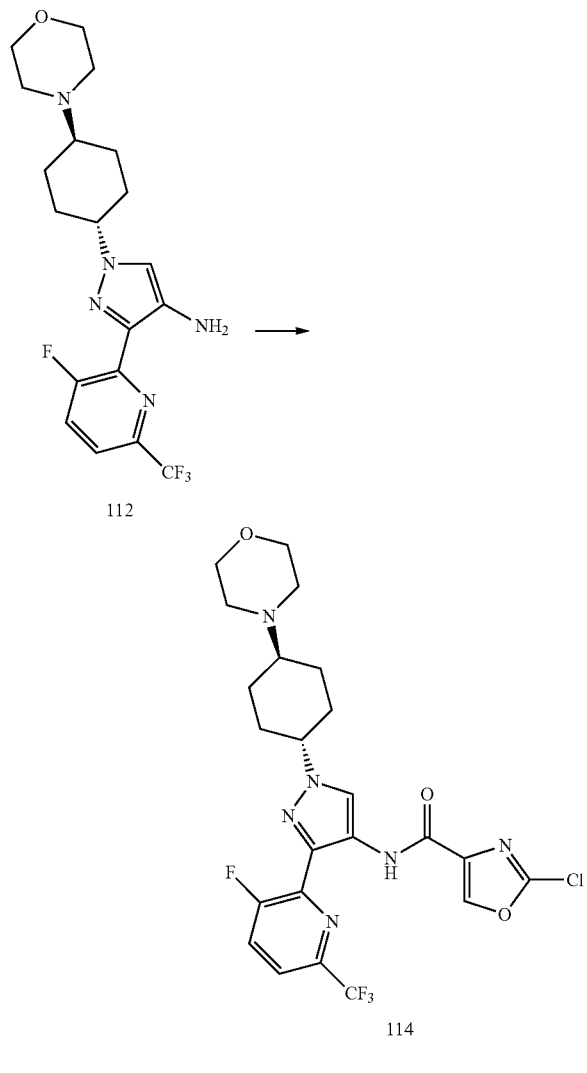

2-chlorooxazole-4-carboxylic acid (1.33 g, 9.02 mM), HATU (4.56 g, 12.0 mM), Hünig's base (6 ml, 34.4 mM) were placed in a round bottom flask and dry DCM (500 ml) was added. The clear solution was then treated with the amine 112 (3.22 g, 7.79 mM) from Example 6. The mixture was stirred for two days at room temperature. Saturated aqueous NaHCO$_3$ (400 ml) was added and the mixture was extracted with DCM (2×300 ml). The organic layers were filtered through Na$_2$SO$_4$ and solvents were removed under reduced pressure. The crude product was purified by CombiFlash chromatography eluting with DCM/MeOH—NH$_3$ (2 M) (gradient 0 to 3%) which yielded 4.05 g (96% yield) of the title compound 114 in form of an off-white solid.

$^1$H NMR (400 MHz, CDCl$_3$) δ 11.27 (s, 1H), 8.46 (d, J=0.8 Hz, 1H), 8.20 (d, J=0.3 Hz, 1H), 7.75-7.56 (m, 2H), 4.22 (tt, J=12.0, 3.9 Hz, 1H), 3.83-3.68 (m, 4H), 2.72-2.53 (m, 4H), 2.48-2.25 (m, 2H), 2.23-2.04 (m, 2H), 1.89 (qd, J=12.9, 3.4 Hz, 2H), 1.60-1.35 (m, 2H); MS (ESI) (m/z): 543 [M+H]$^+$.

Example 8

Preparation of N-(3-(3-fluoro-6-(trifluoromethyl)pyridin-2-yl)-1-((1r,4r)-4-morpholinocyclohexyl)-1H-pyrazol-4-yl)-2-(1H-pyrazol-4-yl)oxazole-4-carboxamide 11-7

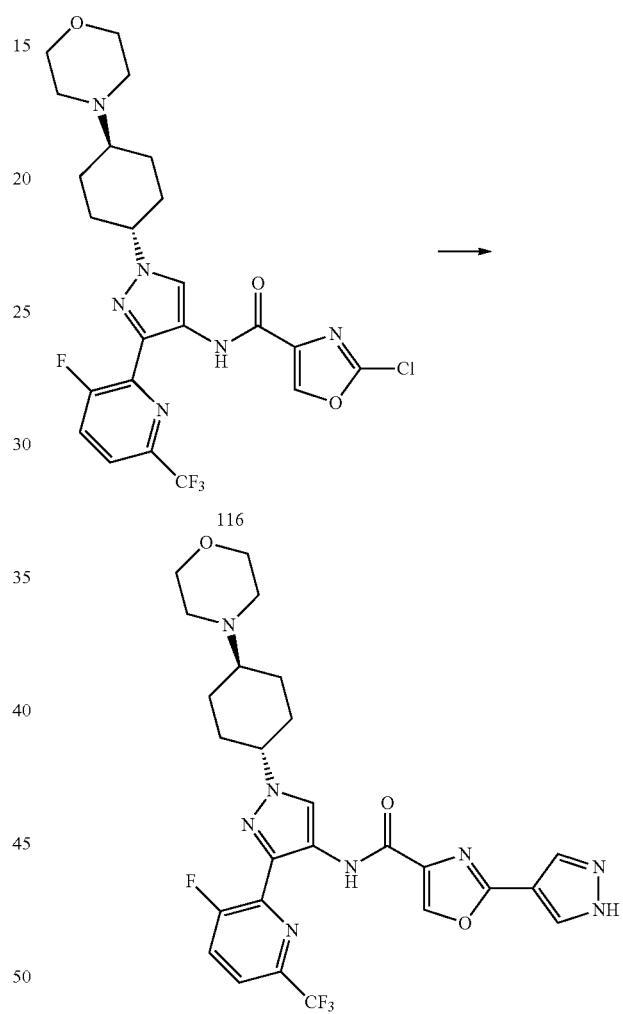

The oxazole chloride 116 (3.70 g, 6.82 mM) from Example 8 was dissolved in dioxane (400 ml) to give a clear, yellow solution. (1H-pyrazol-4-yl)boronic acid (3.05 g, 27.3 mM), tetrakis(triphenylphosphane)palladium (630 mg, 8 mol %) and Na$_2$CO$_3$ (3.61 g, 34.1 mM) dissolved in H$_2$O (80 ml) were added to the flask. The reaction mixture was degassed, backfilled with nitrogen and subsequently refluxed for 2 hours. Analysis by TLC and LCMS showed complete conversion, the solvents were removed under reduced pressure. Water (400 ml) was added and the mixture was extracted with EtOAc (6×500 ml). The product has low solubility in organic solvents; hence a large amount of EtOAc was required. The combined organic phases were filtered through Na₂SO₄, silica gel was added and solvents were removed under reduced pressure. Further purification by CombiFlash chromatography eluting with DCM/MeOH—NH₃ (3.5 M) (gradient 0 to 5%) resulted in 3.71 g (93% yield) of the title compound II-7 in form of an off-white solid.

¹H NMR (400 MHz, DMSO-d₆) δ 13.52 (s, 1H), 10.82 (s, 1H), 8.76 (s, 1H), 8.69-8.47 (m, 1H), 8.49-8.23 (m, 1H), 8.25-7.92 (m, 2H), 4.31 (tt, J=11.7, 4.0 Hz, 1H), 3.57 (t, J=4.6 Hz, 4H), 2.41-2.29 (m, 1H), 2.14 (d, J=11.4 Hz, 2H), 1.96 (d, J=12.2 Hz, 2H), 1.91-1.78 (m, 2H), 1.43 (q, J=11.9, 11.3 Hz, 2H); MS (ESI) (m/z): 575 [M+H]⁺.

Example 9

Preparation of 1-(3,6-difluoropyridin-2-yl)ethan-1-one 118

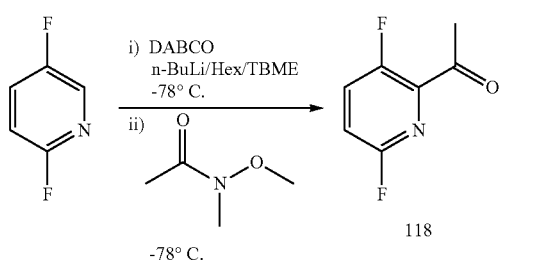

1-(3,6-difluoropyridin-2-yl)ethan-1-one 118 was prepared according to the method of J. Med. Chem. 56(5), 2013, 1799-1810, incorporated herein by reference. Briefly, a suspension of DABCO (49.7 g, 442.8 mmol) in TBME (600 mL) was prepared in a three-neck flask fitted with an overhead stirrer. Upon cooling to −78° C., an n-butyl lithium solution (2.5M in Hexane, 164 mL) was added via dropping funnel over 90 minutes. After two hours and while maintaining the temperature at −78° C., a solution of 2,5-difluoropyridine (40 g, 340.6 mmol) in TBME (20 mL) was via dropping funnel over 30 minutes. After another hour at −78° C., a solution of N-Methoxy-N-methylacetamide (44.3 mL, 341.8 mmol) in TBME (45 mL) was added via dropping funnel over 20 minutes. After two hours, the reaction was complete based on LC-MS. The reaction was carefully quenched with a saturated solution of NH₄Cl (400 mL) then diluted with ethyl acetate (400 mL). The aqueous layer was further extracted twice with ethyl acetate. The combined organic phases were washed with saturated NaHCO₃ solution, brine, dried over solid sodium sulfate, then concentrated in vacuo. After drying on high vacuum, 47.2 g of 1-(3,6-difluoropyridin-2-yl)ethan-1-one 118 was obtained. 1H NMR (300 MHz, Chloroform-d) δ 7.69 (td, J=8.9, 5.8 Hz, 1H), 7.23-7.14 (m, 1H), 2.66 (s, 3H); LCMS (m/z): 158.1 (MH+).

Example 10

Preparation of (E)-1-(3,6-difluoropyridin-2-yl)-3-(dimethylamino) prop-2-en-1-one 120

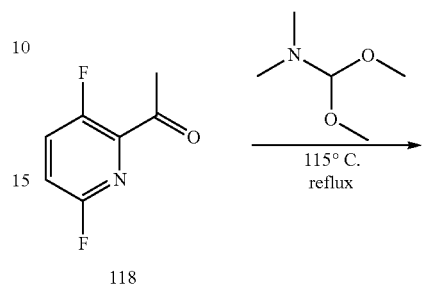

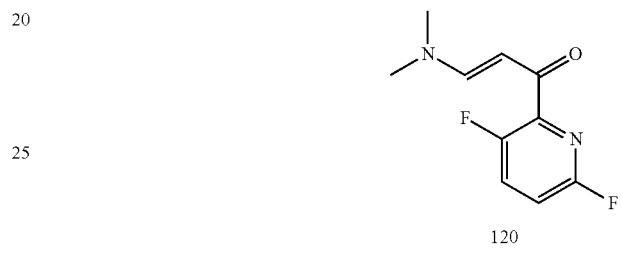

A solution of 1-(3,6-difluoropyridin-2-yl)ethan-1-one 118 (47.2 g, 300.2 mmol) in N,N-dimethylformamide dimethyl acetal (80.0 mL, 600.4 mmol) was refluxed at 103° C. After 1 hour, the reaction was complete based on LC-MS. The solution was concentrated in vacuo and dried on high vacuum to yield 61.6 g of (E)-1-(3,6-difluoropyridin-2-yl)-3-(dimethylamino)prop-2-en-1-one 120 as a dark orange solid.

¹H NMR (300 MHz, Chloroform-d) δ 7.81 (d, J=12.6 Hz, 1H), 7.63-7.51 (m, 1H), 7.02-6.94 (m, 1H), 5.89 (d, J=12.6 Hz, 1H), 3.16 (s, 3H), 2.94 (s, 3H); LCMS (m/z): 213.1 (MH+).

Example 11

Preparation of 3,6-difluoro-2-(1H-pyrazol-3-yl)pyridine 122

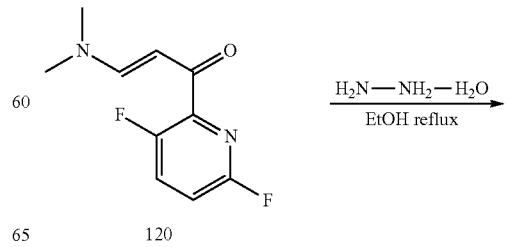

-continued

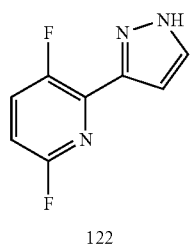

122

(E)-1-(3,6-difluoropyridin-2-yl)-3-(dimethylamino)prop-2-en-1-one 120 (61.6 g, 290.3 mmol) was heated in hydrazine hydrate (64% hydrazine, 18.3 mL) at 98° C. for 30 minutes. After concentration in vacuo and drying on high vacuum overnight. The residue was triturated twice from isopropyl alcohol yielding 37.3 g of 3,6-difluoro-2-(1H-pyrazol-3-yl)pyridine 122 as a tan solid.

$^1$H NMR (300 MHz, Chloroform-d) δ 7.76 (d, J=2.0 Hz, 1H), 7.62 (td, J=8.9, 6.0 Hz, 1H), 6.95 (dd, J=3.7, 2.0 Hz, 1H), 6.88 (ddd, J=8.8, 3.7, 2.8 Hz, 1H); LCMS (m/z): 182.1 (MH+).

Example 12

Preparation of 3,6-difluoro-2-(4-nitro-1H-pyrazol-3-yl)pyridine 124

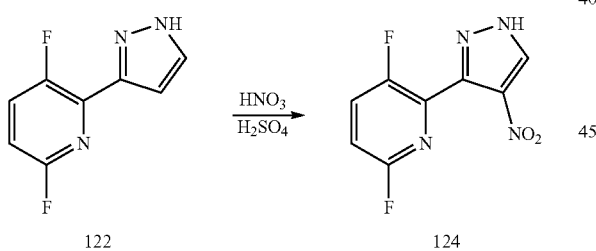

122  124

To a solution of 3,6-difluoro-2-(1H-pyrazol-3-yl)pyridine 122 (37.3 g, 205.9 mmol) in 180 mL H$_2$SO$_4$ cooled to 0° C. was added HNO$_3$ (90% fuming, 19.4 mL) dropwise over 40 minutes. The reaction was allowed to gradually warm to room temperature overnight. The solution was poured over ice and neutralized with aqueous NaOH to pH 8. The solid was filtered then taken up into ethyl acetate. The aqueous layer was extracted twice with ethyl acetate, combined organic layers washed once with brine then dried over sodium sulfate. This was combined with the first ethyl acetate solution, filtered, and concentrated in vacuo. The resulting solid was triturated with ethyl acetate and hexanes to yield 39.9 g of 3,6-difluoro-2-(4-nitro-1H-pyrazol-3-yl)pyridine 124 as a light yellow solid.

$^1$H NMR (300 MHz, Chloroform-d) δ 8.46 (s, 1H), 7.72 (td, J=8.2, 5.8 Hz, 1H), 7.15 (dt, J=8.9, 3.3 Hz, 1H), 1.25 (s, 1H); LCMS (m/z): 227.1 (MH+).

Example 13

Preparation of 2-(1-((1r,4r)-4-ethoxycyclohexyl)-4-nitro-1H-pyrazol-3-yl)-3,6-difluoropyridine 126

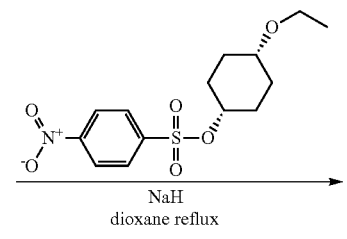

124

To a solution of 3,6-difluoro-2-(4-nitro-1H-pyrazol-3-yl)pyridine 124 (39.8 g, 176 mmol) in 1 L dioxane cooled to 0° C. was added NaH (60% dispersion in mineral oil, 10.56 g, 264 mmol). After allowing to warm to room temperature for two hours, 4-ethoxycyclohexyl 4-nitrobenzenesulfonate (2:1 ratio of 1s,4s:1r,4r; 69.5 g, 221 mmol) was added portionwise. The reaction was heated to gentle reflux for 48 hrs. Upon cooling to room temperature, the reaction was quenched with ice and concentrated in vacuo. The crude material was purified by silica gel chromatography eluting with ethyl acetate and hexanes, then further triturated with ethyl acetate to yield 30.1 g of 2-(1-((r,4r)-4-ethoxycyclohexyl)-4-nitro-1H-pyrazol-3-yl)-3,6-difluoropyridine 126 as a light yellow solid.

¹H NMR (300 MHz, Chloroform-d) δ 8.26 (s, 1H), 7.64 (ddd, J=8.9, 7.7, 5.9 Hz, 1H), 7.06 (ddd, J=8.8, 3.6, 2.9 Hz, 1H), 4.25 (tt, J=11.8, 3.9 Hz, 1H), 3.54 (q, J=7.0 Hz, 2H), 3.34 (tt, J=10.6, 4.1 Hz, 1H), 2.36-2.19 (m, 4H), 1.94-1.79 (m, 2H), 1.52-1.38 (m, 2H), 1.21 (t, J=7.0 Hz, 3H); LCMS (m/z): 353.2 (MH+).

Example 14

Preparation of 3-(3,6-difluoropyridin-2-yl)-1-((1r,4r)-4-ethoxycyclohexyl)-1H-pyrazol-4-amine hydrochloride 128

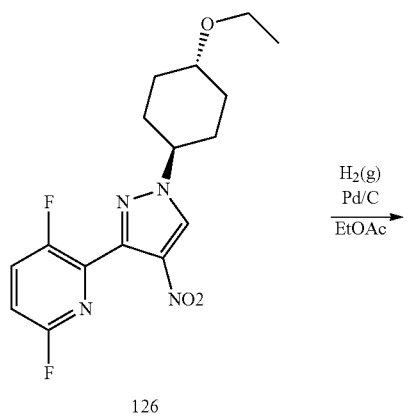

126

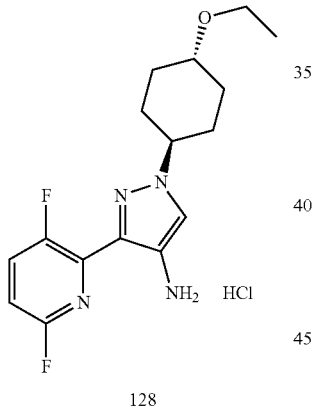

128

A Parr shaker flask with 2-(1-((1r,4r)-4-ethoxycyclohexyl)-4-nitro-1H-pyrazol-3-yl)-3,6-difluoropyridine 126 (6.24 g, 17.7 mmol) dissolved in ethyl acetate (200 mL) was charged with 10% palladium on carbon (627 mg). The mixture was shaken under hydrogen gas at 40 psi overnight. The mixture was filtered through celite into a receiving flask with HCl (1.46 mL of 12.1 N aqueous solution). Upon concentration by rotovap and after drying on high vacuum overnight, 3-(3,6-difluoropyridin-2-yl)-1-((1r,4r)-4-ethoxycyclohexyl)-1H-pyrazol-4-amine hydrochloride 128 (6.2 g) was obtained as a light yellow solid. LCMS (m/z): 323.2 (MH+).

Example 15

Preparation of 2-bromo-N-(3-(3,6-difluoropyridin-2-yl)-1-((1r,4r)-4-ethoxycyclohexyl)-1H-pyrazol-4-yl)oxazole-4-carboxamide 130

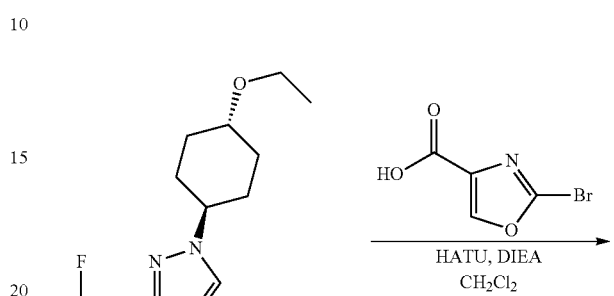

128

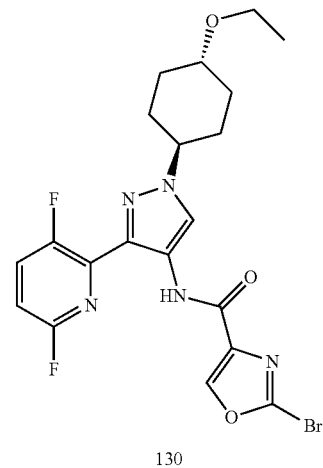

130

In a vial were combined 3-(3,6-difluoropyridin-2-yl)-1-((1r,4r)-4-ethoxycyclohexyl)-1H-pyrazol-4-amine hydrochloride 128 (110 mg, 0.306 mmol), 2-bromooxazole-4-carboxylic acid (73 mg, 0.369 mmol), N,N-diisopropylethylamine (160 μL, 0.920 mmol), and HATU (175 mg, 0.461 mmol) in CH₂Cl₂ (4 mL). After 3 hours, the reaction mixture was diluted with ethyl acetate and water. The organic phase was washed twice with water then a brine solution, dried over sodium sulfate, filtered, then concentrated. The compound was purified by silica gel chromatography eluting with ethyl acetate and hexanes yielding 2-bromo-N-(3-(3,6-difluoropyridin-2-yl)-1-((1r,4r)-4-ethoxycyclohexyl)-1H-pyrazol-4-yl)oxazole-4-carboxamide 130 (148 mg, 0.298 mmol) as a white solid.

¹H NMR (300 MHz, Chloroform-d) δ 11.43 (s, 1H), 8.41 (s, 1H), 8.28 (s, 1H), 7.64 (ddd, J=9.4, 8.8, 6.1 Hz, 1H), 6.86 (ddd, J=8.8, 3.7, 2.6 Hz, 1H), 4.26 (tt, J=11.9, 3.7 Hz, 1H), 3.56 (q, J=7.0 Hz, 2H), 3.37 (tt, J=10.5, 3.9 Hz, 1H), 2.25 (t, J=14.9 Hz, 4H), 1.96-1.81 (m, 2H), 1.54-1.39 (m, 2H), 1.22 (t, J=7.0 Hz, 3H); LCMS (m/z): 497.9 (MH+).

Example 16

Preparation of 2-chloro-N-(3-(3,6-difluoropyridin-2-yl)-1-((1r,4r)-4-ethoxycyclohexyl)-1H-pyrazol-4-yl)oxazole-4-carboxamide 132

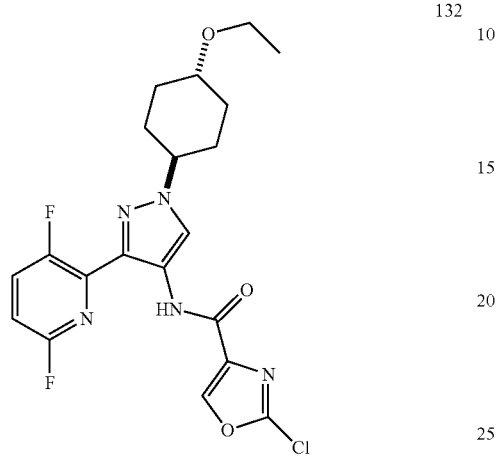

132

Compound 132 was made according to the method of Example 16, using 2-chlorooxazole-4-carboxylic acid.

$^1$H NMR (300 MHz, Chloroform-d) δ 11.38 (s, 1H), 8.40 (s, 1H), 8.22 (s, 1H), 7.64 (ddd, J=9.4, 8.8, 6.0 Hz, 1H), 6.85 (ddd, J=8.8, 3.7, 2.6 Hz, 1H), 4.26 (tt, J=11.9, 3.8 Hz, 1H), 3.56 (q, J=7.0 Hz, 2H), 3.36 (tt, J=10.6, 4.0 Hz, 1H), 2.24 (t, J=14.6 Hz, 4H), 1.96-1.80 (m, 2H), 1.54-1.38 (m, 2H), 1.22 (t, J=7.0 Hz, 3H); LCMS (m/z): 452.2 (MH+).

Example 17

Preparation of N-(3-(3,6-difluoropyridin-2-yl)-1-((1r,4r)-4-ethoxycyclohexyl)-1H-pyrazol-4-yl)-2-(1H-pyrazol-4-yl)oxazole-4-carboxamide II-9

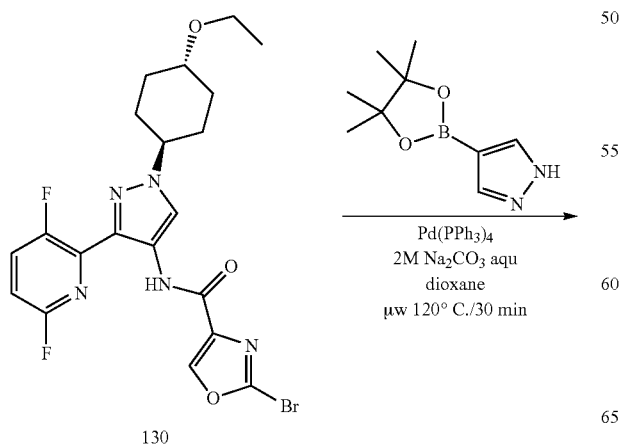

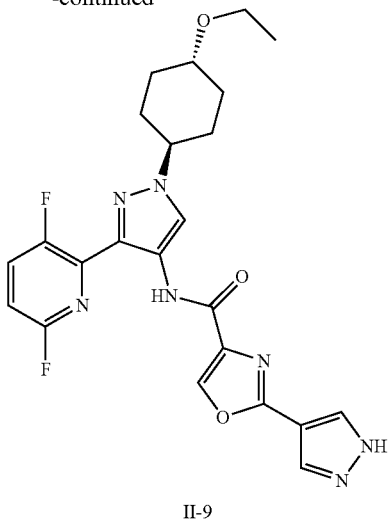

II-9

In a microwave vial were combined 2-bromo-N-(3-(3,6-difluoropyridin-2-yl)-1-((1r,4r)-4-ethoxycyclohexyl)-1H-pyrazol-4-yl)oxazole-4-carboxamide 130 (148 mg, 0.298 mmol), 4-pyrazoleboronic acid pinacol ester (116 mg, 0.596 mmol), and 2M Na$_2$CO$_3$ aqueous solution (447 μL) in 3 mL dioxane. The mixture was purged under nitrogen gas then tetrakis(triphenylphosphine) palladium(0) (34 mg, 0.03 mmol) was added. This composition was microwaved at 120° C. for 30 minutes. Solids were filtered through celite and the filtrate concentrated. The compound was purified by silica gel chromatography eluting with ethyl acetate and hexanes yielding N-(3-(3,6-difluoropyridin-2-yl)-1-((1r,4r)-4-ethoxycyclohexyl)-1H-pyrazol-4-yl)-2-(1H-pyrazol-4-yl)oxazole-4-carboxamide II-9 (97.7 mg, 0.202 mmol) as a white solid.

$^1$H NMR (300 MHz, Chloroform-d) δ 11.68 (s, 1H), 8.44 (s, 1H), 8.27-8.17 (m, 3H), 7.66 (td, J=9.1, 6.1 Hz, 1H), 6.92-6.83 (m, 1H), 4.36-4.19 (m, 1H), 3.57 (q, J=7.0 Hz, 2H), 3.44-3.32 (m, 1H), 2.36-2.16 (m, 4H), 1.97-1.82 (m, 2H), 1.55-1.40 (m, 2H), 1.23 (t, J=7.0 Hz, 3H); LCMS (m/z): 484.1 (MH+).

Example 18

Preparation of Di-tert-butyl ((4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl) phosphate II-16

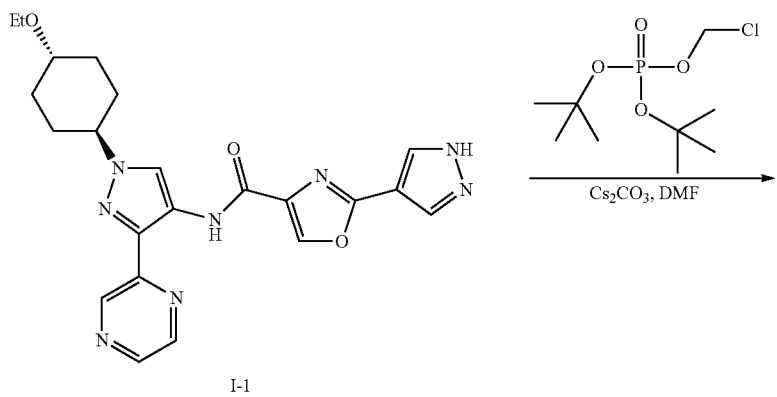

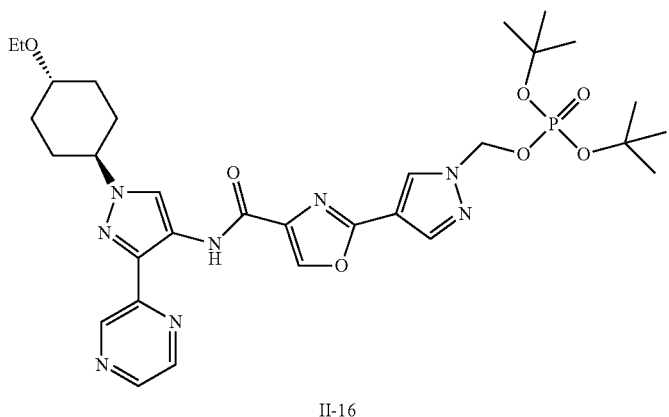

In a round bottom flask, to a DMF (8 mL) solution of N-(1-(trans-4-ethoxycyclohexyl)-3-(pyrazin-2-yl)-1H-pyrazol-4-yl)-2-(1H-pyrazol-4-yl)oxazole-4-carboxamide I-1 (897 mg, 2 mmol), $Cs_2CO_3$ (977.5 mg, 3 mmol) was added at room temperature, after 30 minutes, followed by di-tert-butyl (chloromethyl) phosphate (1.03 g, 4 mmol). At 23 hours, by LC-MS, 7% of I-1 was still present. Additional di-tert-butyl (chloromethyl) phosphate (0.4 g, 1.5 mmol) and $Cs_2CO_3$ (0.2 g, 0.6 mmol) were added and after another 24 hours, about 3% I-1 remained. With ice bath cooling, the reaction was quenched by dropwise addition of water (24 mL), and the mixture was stirred at room temperature for 30 minutes. Precipitate was collected by filtration, washed with water, and was further dried under high vacuum. Compound di-tert-butyl ((4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl) phosphate II-16 was obtained as a light beige color solid: 1.33 g (99% yield).

$^1$H NMR (400 MHz, Chloroform-d) δ 11.56 (s, 1H), 9.34 (d, J=1.6 Hz, 1H), 8.68 (dd, J=2.7, 1.6 Hz, 1H), 8.50 (dd, J=2.7, 0.3 Hz, 1H), 8.40 (s, 1H), 8.36 (d, J=0.6 Hz, 1H), 8.23 (s, 1H), 8.12 (d, J=0.6 Hz, 1H), 5.95 (d, J=12.7 Hz, 2H), 4.21 (tt, J=11.8, 3.8 Hz, 1H), 3.57 (q, J=7.0 Hz, 2H), 3.38 (tt, J=10.6, 4.0 Hz, 1H), 2.30-2.20 (m, 4H), 1.97-1.88 (m, 2H), 1.50-1.43 (m, overlapped, 2H), 1.454 (s, 9H), 1.452 (s, 9H), 1.23 (t, J=7.0 Hz, 3H); LRMS (M+Na) m/z 693.36.

Example 19

Preparation of (4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl dihydrogen phosphate II-17

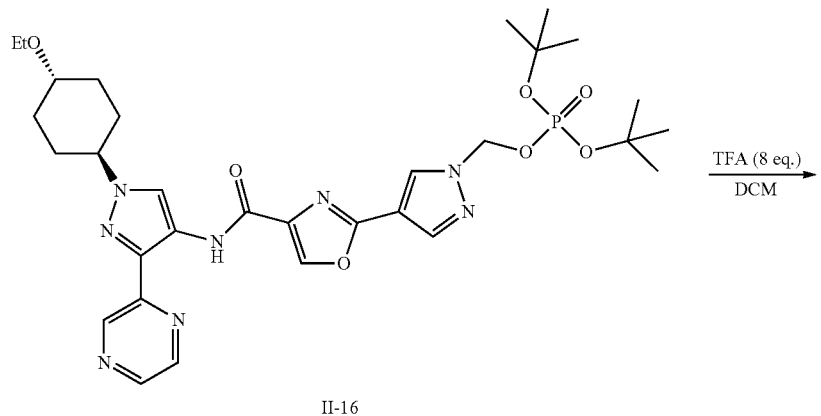

II-16

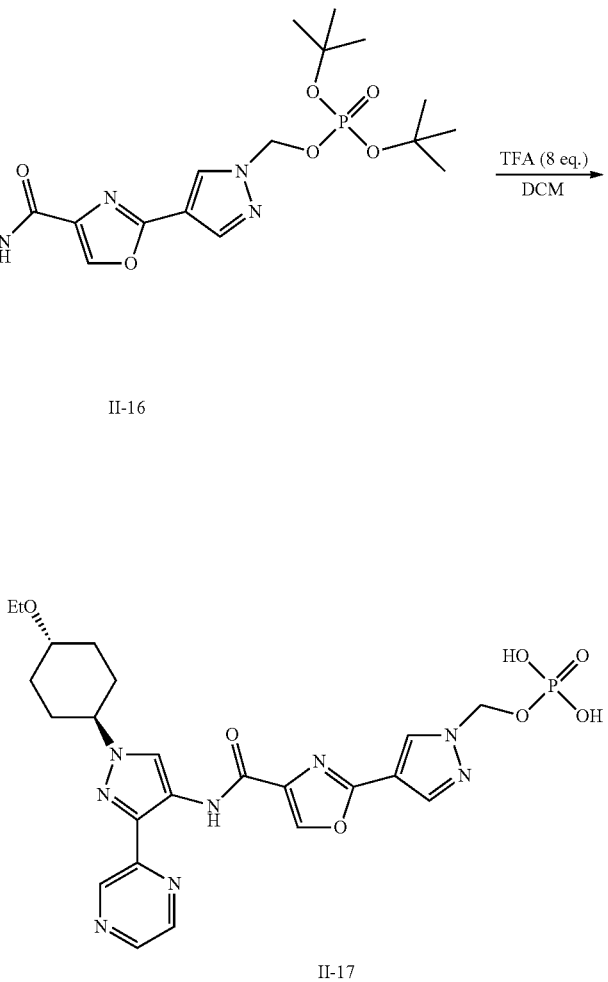

II-17

In a round bottom flask, into a DCM (5 mL) solution of di-tert-butyl ((4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl) phosphate II-16 (671 mg, 1 mmol), TFA (0.613 mL, 8 mmol) was added and the mixture was stirred at room temperature for 22 hours. Reaction went to completion as monitored by LC-MS. Yellow solid was collected by filtration, washed with DCM, and was subsequently suspended in Dioxane-$H_2O$ (10 mL-1 mL), solvent was removed by centrifuging and subsequent removal of supernatant. The process was repeated 3 times, and 3 more times with acetone-$H_2O$ (10 mL-1 mL). Solid was further dried in vacuo. Compound (4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl dihydrogen phosphate II-17 was obtained as a bright yellow solid: 145 mg.

$^1$H NMR (400 MHz, DMSO-$d_6$) δ 11.46 (br s, 2H), 11.45 (s, 1H), 9.19 (d, J=1.5 Hz, 1H), 8.89 (dd, J=2.7, 1.6 Hz, 1H), 8.79 (s, 1H), 8.66 (d, J=0.6 Hz, 1H), 8.61 (d, J=2.7 Hz, 1H), 8.45 (s, 1H), 8.22 (d, J=0.7 Hz, 1H), 5.90 (d, J=10.6 Hz, 2H), 4.34 (br t, J=11.9 Hz, 1H), 3.48 (q, J=7.0 Hz, 2H), 3.38-3.33 (m, partially overlapped with $H_2O$, 1H), 2.11-2.07 (m, 4H), 1.93-1.84 (m, 2H), 1.40-1.30 (m, 2H), 1.10 (t, J=7.0 Hz, 3H); LRMS (M+H) m/z 559.19.

Second fraction of compound was obtained from supernatant, after removal of most organic solvent and collecting precipitate by filtration: 273.4 mg, with same purity as first crop. Combined yield is 75%.

Example 20

Preparation of sodium (4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl phosphate II-18

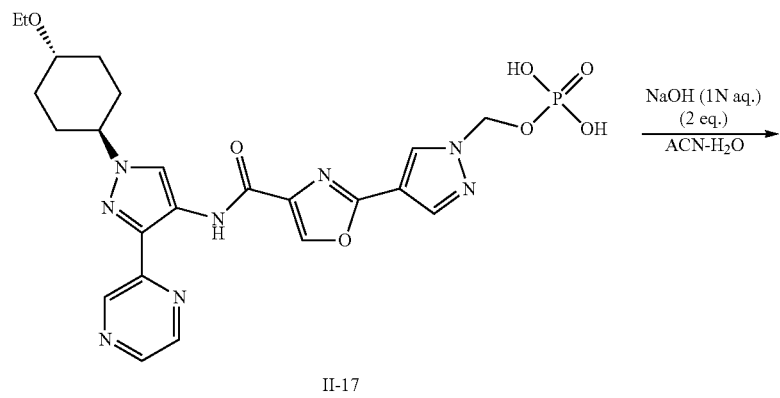

II-17

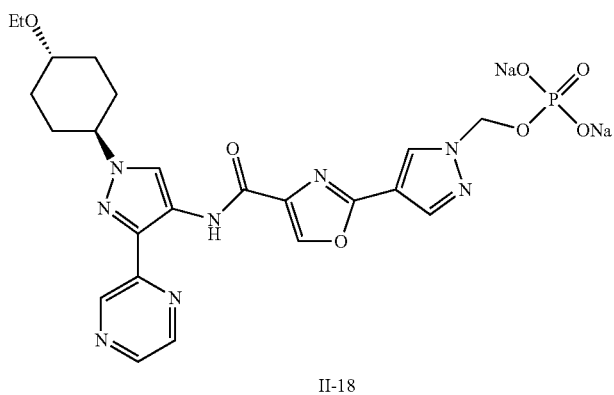

II-18

To a CH₃CN (3 mL) and H₂O (2 mL) suspension of (4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl dihydrogen phosphate II-17 (418 mg, 0.65 mmol), over ice bath, 1N NaOH solution (1.3 mL, 1.3 mmol) was added dropwise. Stirring was continued for another 10 minutes at room temperature. With additional 1 mL of water, the mixture became a clear pale yellow solution. Solvent was removed by lyophilization. Compound sodium (4-(4-((1-(trans-4-ethoxycyclohexyl)-3-(pyrazin-2-yl)-1H-pyrazol-4-yl)carbamoyl)oxazol-2-yl)-1H-pyrazol-1-yl)methyl phosphate II-18 was obtained as a light yellow solid: 399 mg (>99% yield).

$^1$H NMR (400 MHz, Deuterium Oxide) δ 8.26 (d, J=1.4 Hz, 1H), 8.19 (dd, J=2.6, 1.5 Hz, 1H), 8.12 (d, J=2.6 Hz, 1H), 7.95 (s, 1H), 7.76 (s, 1H), 7.69 (s, 1H), 7.38 (s, 1H), 5.57 (d, J=6.6 Hz, 2H), 3.90 (tt, J=11.8, 3.9 Hz, 1H), 3.55 (q, J=7.1 Hz, 2H), 3.40 (tt, J=11.0, 3.9 Hz, 1H), 2.14-2.09 (m, 2H), 2.03-1.97 (m, 2H), 1.66-1.56 (m, 2H), 1.34-1.24 (m, 2H), 1.10 (t, J=7.0 Hz, 3H); LRMS (M+H) m/z 559.23.

Example 21

Preparation of 2-(1-(trans-4-ethoxycyclohexyl)-4-nitro-1H-pyrazol-3-yl)pyrazine 136 as a Mixture of Isomers

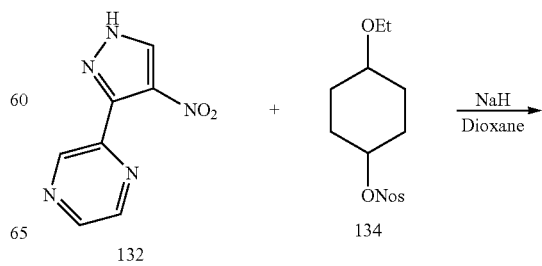

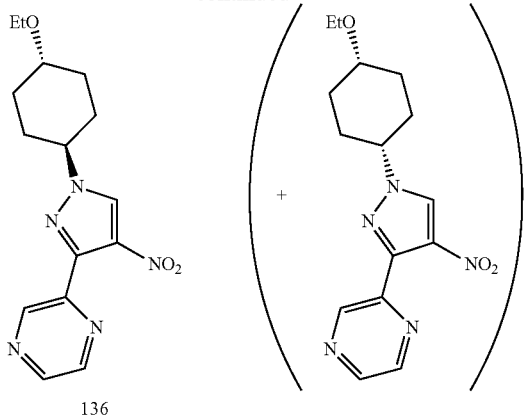

136

Under nitrogen atmosphere, into a 2-L two-neck round bottom flask, 2-(4-nitro-1H-pyrazol-3-yl)pyrazine 132 (17.5 g, 91.6 mmol) was added, followed by 1,4-dioxane (450 mL, 0.2 M). With ice bath cooling, NaH (60% dispersion in Mineral Oil, 5.5 g, 137 mmol) was added portionwise. The ice bath was removed, and the suspension was stirred at 35° C. for 3 hours. Compound 4-ethoxycyclohexyl 4-nitrobenzenesulfonate 134 (36.2 g, 110 mmol, with cis/trans ratio>2) was added, the reaction mixture was stirred at 110° C. with gentle reflux. Another about 0.4 eq (12 g) of 134 was added after 24 hours. At day 4, by LC-MS, 132:136 ≈2:3. The reaction was quenched with about 20 mL of saturated aqueous NaHCO$_3$ solution, and most of the dioxane was removed by rotary evaporation. EtOAc (700 mL) and saturated aqueous NaHCO$_3$—H$_2$O (about 1:1, 700 mL total) were added, and mixed well. Two layers were separated, and the aqueous layer was extracted with EtOAc (400 mL×2). Organic layers were combined, dried (Na$_2$SO$_4$), filtered, and the solvent was removed by rotary evaporation. Product was purified by Silica Gel chromatography, followed by trituration from Hexanes-EtOAc (2:1). Compound 2-(1-(trans-4-ethoxycyclohexyl)-4-nitro-1H-pyrazol-3-yl)pyrazine 136 was obtained as a pale yellow solid: 9.6 g (33% yield); $^1$H NMR (300 MHz, Chloroform-d) δ 9.00 (d, J=1.5 Hz, 1H), 8.71 (dd, J=2.5, 1.5 Hz, 1H), 8.65 (d, J=2.5 Hz, 1H), 4.26 (tt, J=11.7, 3.8 Hz, 2H), 3.56 (q, J=7.0 Hz, 2H), 3.36 (tt, J=10.6, 4.1 Hz, 2H), 2.36-2.21 (m, 4H), 1.95-2.21 (m, 2H), 1.54-1.40 (m, 2H), 1.22 (t, J=7.0 Hz, 3H); LRMS (M+H) m/z 318.2.

Example 22

Preparation of 8-ethoxy-1,4-dioxaspiro[4.5]decane 138

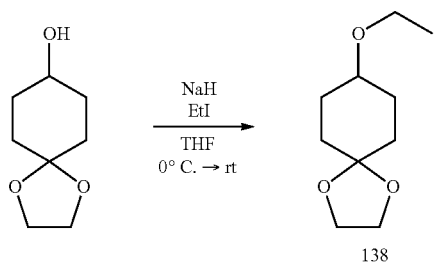

138

Sodium hydride (60% dispersion in mineral oil, 74.3 g, 1.858 mol) in a round bottom flask was washed four times with hexanes. A suspension in THF (1L) was prepared and cooled to 0° C. Gradually, 1,4-dioxaspiro[4.5]decan-8-ol (150 g, 929 mmol) was added and the reaction allowed to warm to room temperature. After two hours, the reaction was cooled back to 0° C. and iodoethane was added via dropping funnel over one hour. The reaction was gradually allowed warmed to room temperature whereupon a reflux condenser was fitted. The reaction was monitored by TLC (1:1 ethyl acetate in hexanes). Upon completion, the reaction was quenched with ice, the solvent was reduced in volume in vacuo, and then diluted with ethyl acetate and water. After extracting twice with ethyl acetate, the combined organic layers were washed with brine, dried over solid sodium sulfate, filtered, and concentrated in vacuo. After drying on high vacuum, 166.9 g of 8-ethoxy-1,4-dioxaspiro[4.5]decane 138 was obtained as a yellow oil.

$^1$H NMR (300 MHz, Chloroform-d) δ 3.90 (t, J=2.2 Hz, 4H), 3.45 (q, J=7.0 Hz, 2H), 3.40-3.32 (m, 1H), 1.82-1.62 (m, 6H), 1.56-1.46 (m, 2H), 1.16 (t, J=7.0 Hz, 3H).

Example 23

Preparation of 4-ethoxycyclohexan-1-one 140

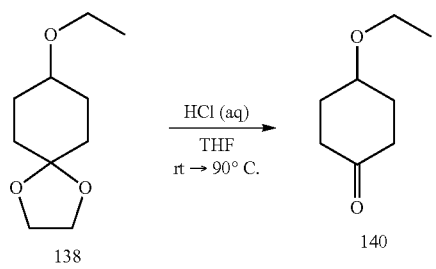

To a solution of 8-ethoxy-1,4-dioxaspiro[4.5]decane 138 (166.9 g, 896.1 mmol) in THF (700 mL) was added a 3M aqueous solution of HCl (597 mL). The solution was heated to 90° C. with an attached reflux condenser for two hours. The reaction was monitored by TLC (1:1 ethyl acetate in hexanes) by taking aliquots quenched with aqueous NaOH and extracted in to ethyl acetate. Upon completion, the solvent volume was reduced in vacuo and was adjusted to pH 8 with 4M NaOH solution. This was extracted twice with ethyl acetate, the combined organic phases were washed with brine, dried over solid sodium sulfate, filtered, and concentrated in vacuo. After drying under high vacuum, 124.2 g of the desired 4-ethoxycyclohexan-1-one 140 was obtained as a yellow oil.

$^1$H NMR (300 MHz, Chloroform-d) δ 3.74-3.61 (m, 1H), 3.53 (q, J=7.0 Hz, 2H), 2.63-2.46 (m, 2H), 2.30-2.15 (m, 2H), 2.12-1.82 (m, 4H), 1.21 (t, J=7.0 Hz, 3H).

Example 24

Preparation of (1s,4s)-4-ethoxycyclohexan-1-ol 142

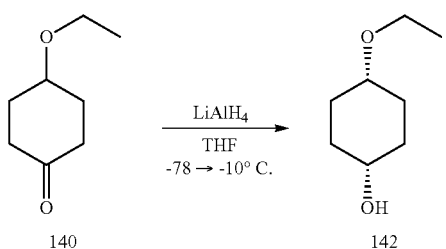

A solution of 4-ethoxycyclohexan-1-one 140 (121.6 g, 855 mmol) in 750 mL of THF was cooled to −78° C. Solid LiAlH₄ (95%, 51.2 g, 1.28 mol) was added portion-wise over one hour then gradually warmed to −10 ° C. After an hour, an aliquot was taken and quenched for TLC analysis in 1:1 ethyl acetate in hexanes showed the reaction was complete. The reaction was cooled back to −78° C. and quenched with dropwise addition of 4M NaOH solution (641 mL). The mixture was diluted and washed three times with ethyl acetate, decanting off the solvent. The combined organic phases were washed with 1M NaOH, brine, dried over solid sodium sulfate, filtered, and concentrated in vacuo. After drying under high vacuum 117.9 g of 4-ethoxy-cyclohexan-1-ol 142 (in ~2:1 ratio of 1s,4s and 2s,4s isomers) was obtained as a yellow oil.

$^1$H NMR (300 MHz, Chloroform-d) δ 3.76-3.61 (m, 1H), 3.52-3.38 (m, 2H), 3.34 (dp, J=6.3, 3.2 Hz, 1H), 3.27-3.18 (m, ~0.5H), 2.01-1.92 (m, 1H), 1.84-1.47 (m, 6H), 1.33-1.25 (m, 1H), 1.17 (td, J=7.0, 2.5 Hz, 3H).

Example 25

Preparation of (1r,4r)-4-ethoxycyclohexyl 4-nitrobenzenesulfonate 144

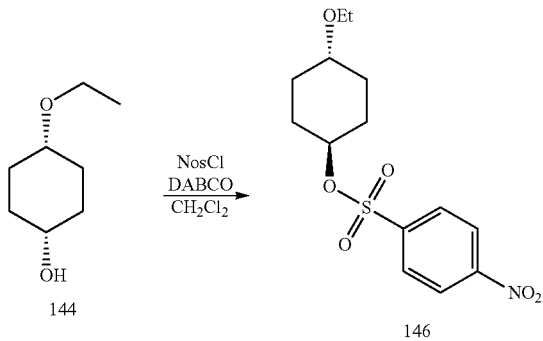

To a solution of 4-ethoxycyclohexan-1-ol 144 (in ~2:1 ratio of 1s,4s and 2s,4s isomers; 112.9 g, 782.9 mmol) in CH₂Cl₂ (800 mL) cooled to 0° C. was added 1,4-diazabi-cyclo[2.2.2]octane (105.4 g, 939.5 mmol). Portion-wise added of 4-nitrobenzenesulfonyl chloride was added at 0° C. over 1 hour then the reaction was gradually warmed to room temperature overnight. When the reaction appeared complete by TLC analysis in 1:1 ethyl acetate in hexanes, it was quenched with addition of NaHCO₃ saturated aqueous solution. After further dilution with CH₂Cl₂ and water, the organic phase isolated and washed further with NaHCO₃ solution, water, and brine. After drying over solid sodium sulfate, the solution was filtered, concentrated in vacuo, and dried under high vacuum. The resulting solid was triturated from ethyl acetate and hexanes to yield 160.8 g of 4-ethoxy-cyclohexyl 4-nitrobenzenesulfonate 146 (as a mixture of 1r,4r and 1s,4s) as an off-white solid.

$^1$H NMR (300 MHz, Chloroform-d) δ 8.51-8.31 (m, 2H), 8.17-8.03 (m, 2H), 4.73 (dtt, J=11.7, 8.1, 4.0 Hz, 1H), 3.44 (qd, J=7.0, 1.5 Hz, 2H), 3.34 (tt, J=6.7, 3.1 Hz, 1H), 1.99-1.87 (m, 2H), 1.81-1.53 (m, 6H), 1.16 (td, J=7.0, 2.8 Hz, 3H).

The following exemplary compounds were prepared using the methods of Examples 1-21. Characterization data for these additional compounds are provided below.

II-1

N-(1-(trans-4-ethoxycyclohexyl)-3-(pyrazin-2-yl)-1H-pyrazol-4-yl)-2-(1H-pyrazol-4-yl)oxazole-4-carboxamide

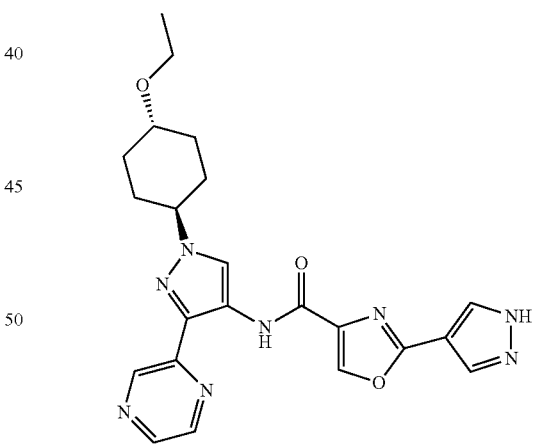

$^1$H NMR (300 MHz, DMSO-d6) δ 13.52 (s, 1H), 11.43 (s, 1H), 9.19 (s, 1H), 8.91 (m, 1H), 8.74 (s, 1H), 8.60 (m, 1H), 8.54 (s, 1H), 8.45 (s, 1H), 8.15 (s, 1H), 4.34 (m, 1H), 3.48 (q, J=7.0 Hz, 2H), 3.35 (m, 1H), 2.09 (m, 4H), 1.89 (q, J=10.2 Hz, 2H), 1.35 (q, J=10.5 Hz, 2H), 1.10 (t, J=6.9 Hz, 3H); LCMS: purity: 100%; MS (m/e): 449.17 (MH+).

II-15

2-(1H-pyrazol-4-yl)-N-(3-(pyridin-2-yl)-1-(2-(2,2,2-trifluoroethoxy)ethyl)-1H-pyrazol-4-yl)oxazole-4-carboxamide

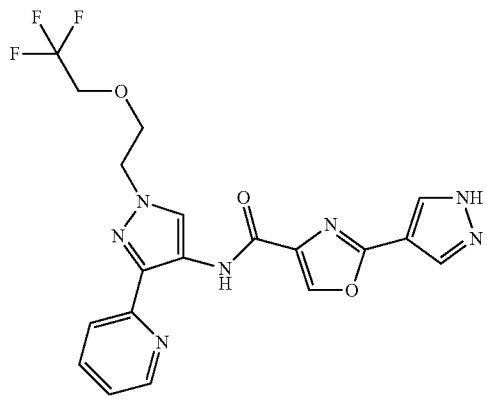 [SMILES: O=C(Nc1cn(CCOCC(F)(F)F)nc1-c1ccccn1)c1coc(-c2cn[nH]c2)n1]

¹HNMR (300 MHz, DMSO-d6) δ 13.50 (br s, 1H), 12.03 (s, 1H), 8.87 (d, J=6.7 Hz, 1H), 8.74 (s, 1H), 8.51 (br s, 1H), 8.46 (s, 1H), 8.14 (br s, 1H), 8.01-7.94 (m, 2H), 7.43-7.39 (m, 1H), 4.44 (t, J=6.7 Hz, 2H), 4.13-4.01 (m, 4H); LCMS (m/z): 448.17 (MH⁺).

II-19

N-(3-(3,6-difluoropyridin-2-yl)-1-((1r,3r)-3-ethoxy-cyclobutyl)-1H-pyrazol-4-yl)-2-(1H-pyrazol-4-yl)oxazole-4-carboxamide

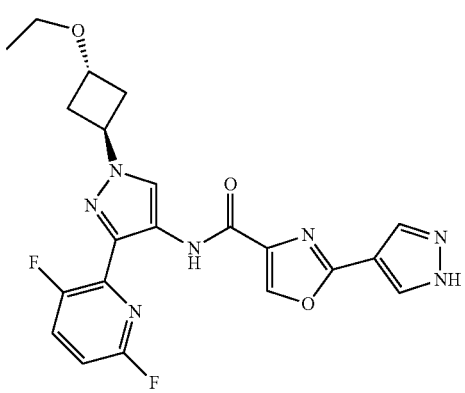 [SMILES: CCO[C@H]1C[C@H](n2cc(NC(=O)c3coc(-c4cn[nH]c4)n3)c(-c3nc(F)ccc3F)n2)C1]

¹H NMR (400 MHz, DMSO-d₆) 1H NMR (400 MHz, DMSO-d6) δ 13.50 (s, 1H), 11.38 (s, 1H), 8.71 (s, 1H), 8.49 (d, J=0.7 Hz, 1H), 8.36 (s, 1H), 8.07 (ddd, J=9.9, 8.9, 6.2 Hz, 1H), 8.05-8.00 (m, 1H), 7.27 (ddd, J=8.8, 3.3, 2.5 Hz, 1H), 5.06 (ttd, J=8.5, 5.5, 0.8 Hz, 1H), 4.26 (dddd, J=11.3, 5.1, 4.3, 2.1 Hz, 1H), 3.36 (q, J=7.0 Hz, 2H), 2.72-2.61 (m, 1H), 2.53-2.40 (m, 1H), 1.20 (dd, J=9.4, 6.9 Hz, 2H), 1.11 (t, J=7.0 Hz, 3H); MS (ESI) (m/z): 456 [M+H]⁺.

II-20

N-(1-(trans-4-hydroxycyclohexyl)-3-(pyrazin-2-yl)-1H-pyrazol-4-yl)-2-(1H-pyrazol-4-yl)oxazole-4-carboxamide

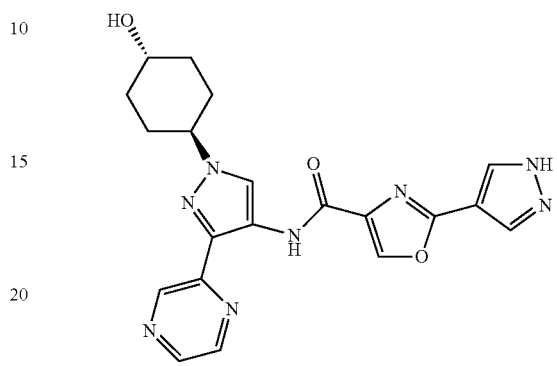

¹H NMR (400 MHz, DMSO-d₆) δ 11.42 (s, 1H), 9.19 (d, J=1.6 Hz, 1H), 8.90 (dd, J=2.6, 1.6 Hz, 1H), 8.74 (s, 1H), 8.60 (d, J=2.6 Hz, 1H), 8.44 (s, 1H), 8.35 (br s, 2H), 4.29 (tt, J=11.5, 4.0 Hz, 1H), 3.53 (tt, J=10.7, 4.0 Hz, 1H), 2.10-2.01 (m, 2H), 1.98-1.82 (m, 4H), 1.44-1.30 (m, 2H); LRMS (M+H) m/z: 421.3.

II-21

N-(1-(trans-4-ethoxycyclohexyl)-3-(3,5,6-trifluoro-pyridin-2-yl)-1H-pyrazol-4-yl)-2-(1H-pyrazol-4-yl)oxazole-4-carboxamide

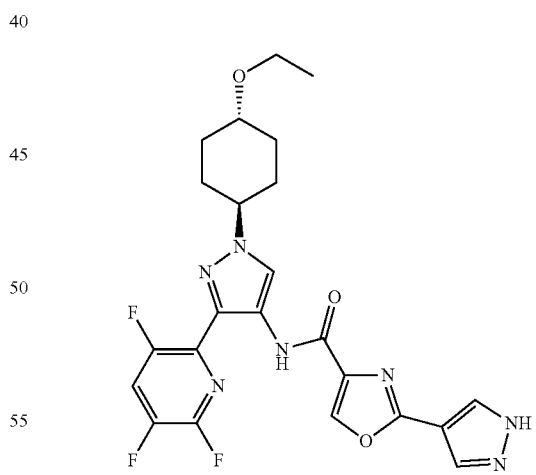

¹H NMR (400 MHz, Chloroform-d) δ 11.39 (s, 1H), 8.43 (s, 1H), 8.22 (s, 2H), 7.56 (dd, J=8.5, 8.5 Hz, 1H), 4.26 (tt, J=11.8, 3.9 Hz, 1H), 3.57 (q, J=7.0 Hz, 2H), 3.37 (tt, J=10.6, 3.9 Hz, 1H), 2.31-2.19 (m, 4H), 1.94-1.83 (m, 2H), 1.52-1.41 (m, 2H), 1.23 (t, J=7.0 Hz, 3H); LRMS (M+H) m/z 502.2.

II-22

N-(3-(4,6-difluoropyridin-2-yl)-1-(trans-4-ethoxycyclohexyl)-1H-pyrazol-4-yl)-2-(1H-pyrazol-4-yl)oxazole-4-carboxamide

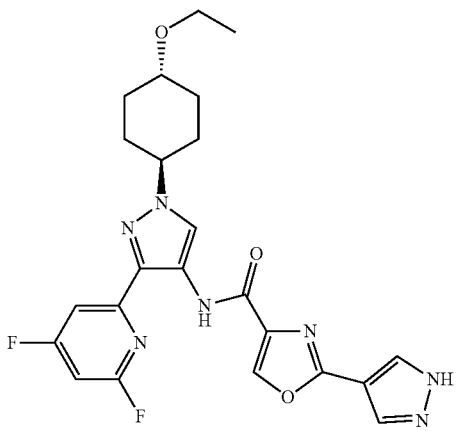 [SMILES: CCO[C@H]1CC[C@H](n2cc(NC(=O)c3coc(-c4cn[nH]c4)n3)c(-c3cc(F)cc(F)n3)n2)CC1]

$^1$H NMR (400 MHz, Chloroform-d) δ 11.63 (s, 1H), 8.38 (s, 1H), 8.23 (s, 3H), 7.67 (dd, J=8.9, 2.0 Hz, 1H), 6.59 (ddd, J=8.2, 1.8, 1.8 Hz, 1H), 4.18 (tt, J=11.8, 3.7 Hz, 1H), 3.57 (q, J=7.0 Hz, 2H), 3.37 (tt, J=10.6, 3.9 Hz, 1H), 2.24 (td, J=14.3, 3.7 Hz, 4H), 1.96-1.84 (m, 2H), 1.53-1.40 (m, 2H), 1.23 (t, J=7.0 Hz, 3H); LRMS (M+H) m/z 484.2.

II-23

N-(1-((1r,4r)-4-morpholinocyclohexyl)-3-(pyrazin-2-yl)-1H-pyrazol-4-yl)-2-(1H-pyrazol-4-yl)oxazole-4-carboxamide

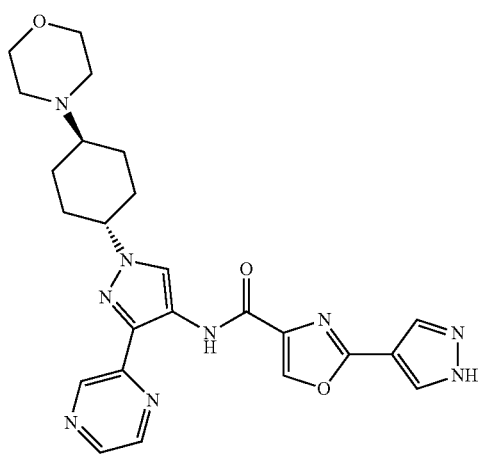 [SMILES: O=C(Nc1cn([C@H]2CC[C@H](N3CCOCC3)CC2)nc1-c1cnccn1)c1coc(-c2cn[nH]c2)n1]

$^1$H NMR (400 MHz, DMSO-d$_6$) δ 13.51 (s, 1H), 11.42 (s, 1H), 9.17 (d, J=1.5 Hz, 1H), 8.89 (dd, J=2.7, 1.6 Hz, 1H), 8.73 (s, 1H), 8.59 (d, J=2.6 Hz, 1H), 8.43 (s, 1H), 7.72 (s, 1H), 7.66 (s, 1H), 4.25 (tt, J=11.7, 3.9 Hz, 1H), 3.57-3.50 (m, 4H), 2.48-2.42 (m, 3H), 2.30 (tt, J=11.5, 3.4 Hz, 1H), 2.10 (dt, J=9.7, 3.2 Hz, 2H), 1.96-1.86 (m, 3H), 1.81 (td, J=12.4, 3.4 Hz, 2H), 1.37 (qd, J=12.8, 3.3 Hz, 2H); MS (ESI) (m/z): 490 [M+H]$^+$.

II-24

N-(1-((1r,4r)-4-ethoxycyclohexyl)-3-(3-fluoro-6-(trifluoromethyl)pyridin-2-yl)-1H-pyrazol-4-yl)-2-(1H-pyrazol-4-yl)oxazole-4-carboxamide

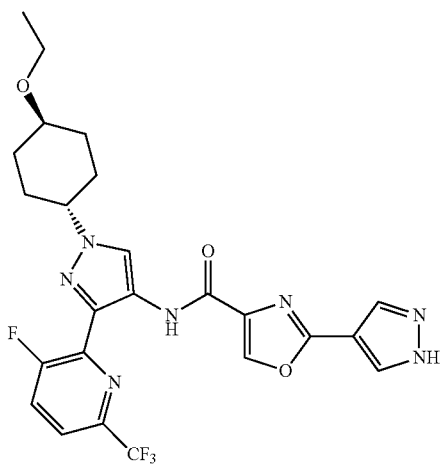 [SMILES: CCO[C@H]1CC[C@H](n2cc(NC(=O)c3coc(-c4cn[nH]c4)n3)c(-c3nc(C(F)(F)F)ccc3F)n2)CC1]

$^1$H NMR (400 MHz, DMSO-d$_6$) δ 13.48 (s, 1H), 10.78 (s, 1H), 8.72 (s, 1H), 8.55 (d, J=0.7 Hz, 1H), 8.17 (s, 2H), 8.11 (ddd, J=10.6, 8.6, 0.8 Hz, 1H), 7.96 (dd, J=8.6, 3.2 Hz, 1H), 4.33 (tt, J=11.6, 3.4 Hz, 1H), 3.44 (q, J=6.9 Hz, 2H), 2.10-2.02 (m, 4H), 1.91-1.76 (m, 2H), 1.36 (d, J=9.9 Hz, 1H), 1.36-1.26 (m, 1H), 1.07 (t, J=7.0 Hz, 3H); MS (ESI) (m/z): 534 [M+H]$^+$.

II-26

N-(1-((1r,3r)-3-morpholinocyclobutyl)-3-(pyrazin-2-yl)-1H-pyrazol-4-yl)-2-(1H-pyrazol-4-yl)oxazole-4-carboxamide

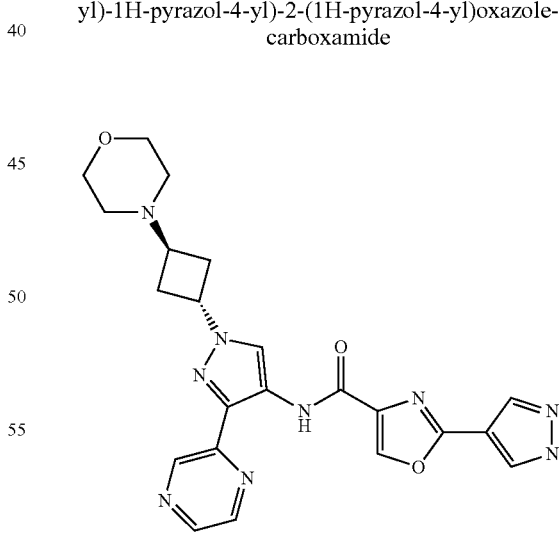

$^1$H NMR (400 MHz, DMSO-d$_6$) $^1$H NMR (400 MHz, DMSO-d$_6$) δ 13.50 (s, 1H), 11.40 (s, 1H), 9.22 (d, J=1.6 Hz, 1H), 8.88 (dd, J=2.7, 1.6 Hz, 1H), 8.71 (s, 1H), 8.59 (d, J=2.6 Hz, 1H), 8.46 (s, 1H), 8.32 (s, 2H), 5.02-4.91 (m, 1H), 3.58 (t, J=4.6 Hz, 4H), 3.05-2.94 (m, 1H), 2.59-2.50 (m, 1H), 2.50 (dd, J=7.9, 2.1 Hz, 1H); MS (ESI) (m/z): 462 [M+H]$^+$.

105

II-27

N-(1-((1s,3s)-3-morpholinocyclobutyl)-3-(pyrazin-2-yl)-1H-pyrazol-4-yl)-2-(1H-pyrazol-4-yl)oxazole-4-carboxamide

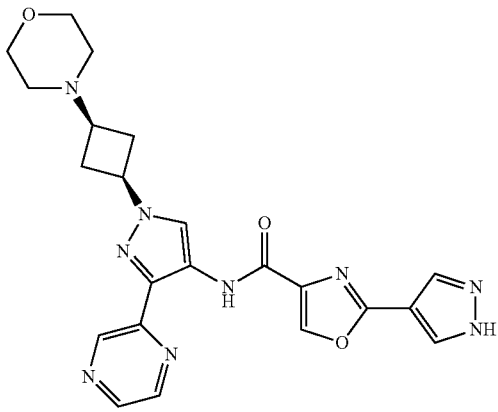 [SMILES: O=C(Nc1cn([C@H]2C[C@@H](N3CCOCC3)C2)nc1-c1cnccn1)c1coc(-c2cn[nH]c2)n1]

¹H NMR (400 MHz, DMSO-d₆)¹H NMR (400 MHz, DMSO-d₆) δ 13.50 (s, 1H), 11.40 (s, 1H), 9.20 (d, J=1.5 Hz, 1H), 8.88 (dd, J=2.6, 1.6 Hz, 1H), 8.72 (s, 1H), 8.59 (d, J=2.6 Hz, 1H), 8.51 (s, 1H), 8.45 (s, 1H), 8.13 (s, 1H), 5.71 (s, 1H), 4.78-4.66 (m, 1H), 3.57 (t, J=4.6 Hz, 4H), 2.64-2.49 (m, 3H), 2.36-2.25 (m, 6H); MS (ESI) (m/z): 462 [M+H]⁺.

II-28

2-(3-fluoro-1H-pyrazol-4-yl)-N-(1-((1r,4r)-4-morpholinocyclohexyl)-3-(pyrazin-2-yl)-1H-pyrazol-4-yl)oxazole-4-carboxamide

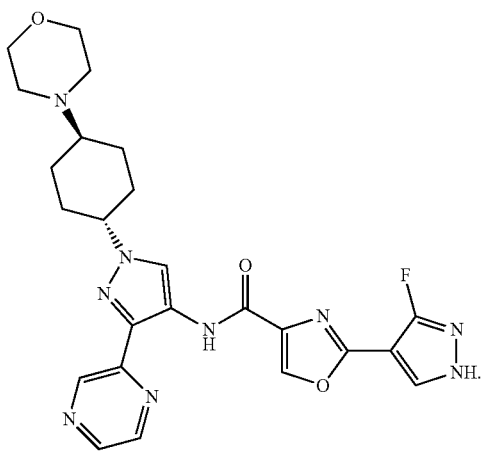

MS (ESI) (m/z): 508 [M + H]⁺

106

II-29

N-(3-(3,6-difluoropyridin-2-yl)-1-(cis-4-(4-methylpiperazin-1-yl)cyclohexyl)-1H-pyrazol-4-yl)-2-(1H-pyrazol-4-yl)oxazole-4-carboxamide

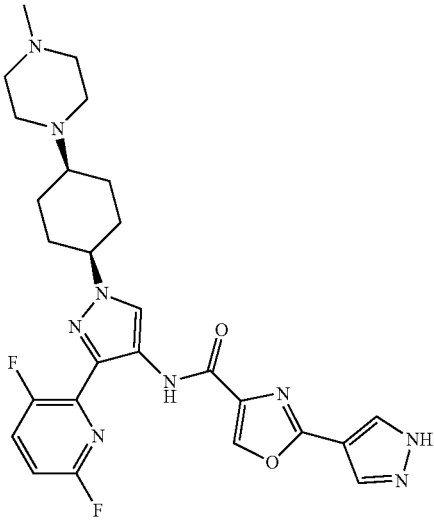 [SMILES: CN1CCN([C@H]2CC[C@@H](n3cc(NC(=O)c4coc(-c5cn[nH]c5)n4)c(-c4nc(F)ccc4F)n3)CC2)CC1]

¹H NMR (400 MHz, DMSO-d₆) δ 13.52 (s, 1H), 11.41 (s, 1H), 8.73 (s, 1H), 8.43 (s, 1H), 8.21 (s, 2H), 8.08 (ddd, J=9.3, 9.3, 6.1 Hz, 1H), 7.27 (ddd, J=8.8, 2.8, 2.8 Hz, 1H), 4.41 (tt, J=8.3, 4.2 Hz, 1H), 2.44-2.07 (m, 14H), 1.98-1.76 (m, 4H), 1.62-1.50 (m, 2H); LRMS (M+H) m/z 538.4.

II-30

N-(3-(3,6-difluoropyridin-2-yl)-1-(trans-4-morpholinocyclohexyl)-1H-pyrazol-4-yl)-2-(1H-pyrazol-4-yl)oxazole-4-carboxamide

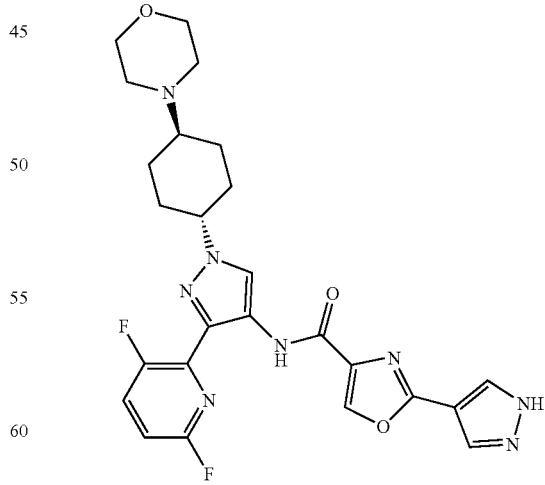

¹H NMR (400 MHz, DMSO-d₆) δ 13.52 (s, 1H), 11.41 (s, 1H), 8.74 (s, 1H), 8.46 (s, 1H), 8.22 (br s, 1H), 8.14-7.93 (m, 1H), 7.27 (ddd, J=8.8, 2.9, 2.9 Hz, 1H), 4.27 (tt, J=11.8, 4.0 Hz, 1H), 3.59-3.51 (m, 4H), 2.49-2.44 (m, 4H), 2.38-2.27

(m, 1H), 2.16-2.07 (m, 2H), 1.98-1.89 (m, 2H), 1.83 (qd, J=12.8, 3.4 Hz, 2H), 1.40 (qd, J=12.8, 3.4 Hz, 2H); LRMS (M+H) m/z 525.3.

II-31

N-(1-((1s,3s)-3-hydroxycyclobutyl)-3-(pyrazin-2-yl)-1H-pyrazol-4-yl)-2-(1H-pyrazol-4-yl)oxazole-4-carboxamide

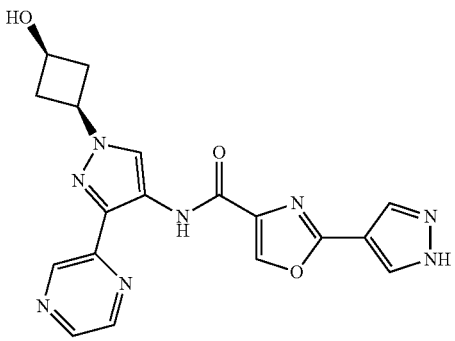 [SMILES: O=C(Nc1cn([C@H]2C[C@@H](O)C2)nc1-c1cnccn1)c1coc(-c2cn[nH]c2)n1]

$^1$H NMR (400 MHz, DMSO-d$_6$) δ 12.68 (s, 1H), 11.41 (d, J=4.1 Hz, 1H), 9.22 (dd, J=5.2, 1.6 Hz, 1H), 8.90 (dd, J=2.7, 1.6 Hz, 1H), 8.73 (s, 1H), 8.60 (d, J=2.6 Hz, 1H), 8.49 (s, 1H), 8.33 (s, 2H), 5.32 (d, J=7.0 Hz, 1H), 4.50 (tt, J=9.1, 7.3 Hz, 1H), 4.02-3.89 (m, 1H), 2.84-2.71 (m, 2H), 2.39 (tdt, J=9.0, 7.9, 2.7 Hz, 2H); MS (ESI) (m/z): 393 [M+H]$^+$.

III-1

2-(1-(cyclopropylmethyl)-1H-pyrazol-4-yl)-N-(1-methyl-3-(pyridin-2-yl)-1H-pyrazol-4-yl)oxazole-4-carboxamide

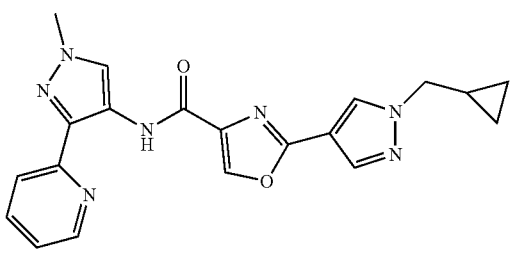 [SMILES: Cn1cc(NC(=O)c2coc(-c3cnn(CC4CC4)c3)n2)c(-c2ccccn2)n1]

$^1$H NMR (300 MHz, DMSO-d6) δ 11.99 (s, 1H), 8.82 (d, J=4.8 Hz, 1H), 8.72 (s, 1H), 8.52 (s, 1H), 8.38 (s, 1H), 8.08 (s, 1H), 7.98-7.88 (m, 2H), 7.40-7.36 (m, 1H), 4.09 (d, J=6.9 Hz, 2H), 3.93 (s, 3H), 1.32 (m, 1H), 0.59-0.53 (m, 2H), 0.45-0.40 (m, 2H); LCMS: purity: 100%; MS (m/e): 390.59 (MH+).

III-2

2-(1H-pyrazol-4-yl)-N-(3-(pyridin-2-yl)-1-(tetrahydro-2H-pyran-4-yl)-1H-pyrazol-4-yl)oxazole-4-carboxamide

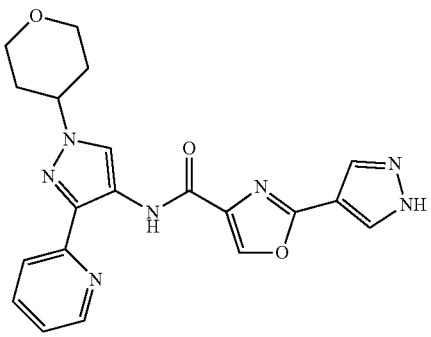 [SMILES: O=C(Nc1cn(C2CCOCC2)nc1-c1ccccn1)c1coc(-c2cn[nH]c2)n1]

$^1$H NMR (300 MHz, DMSO-d$_6$) δ 13.54 (s, 1H), 12.04 (s, 1H), 8.86 (ddd, J=5.0, 1.7, 0.9 Hz, 1H), 8.74 (s, 1H), 8.61-8.49 (m, 1H), 8.46 (s, 1H), 8.26-8.08 (m, 1H), 8.04-7.98 (m, 1H), 7.93 (td, J=7.7, 1.8 Hz, 1H), 7.44-7.34 (m, 1H), 4.67-4.42 (m, 1H), 4.06-3.95 (m, 2H), 3.55-3.42 (m, 2H), 2.04 (h, J=5.0, 4.3 Hz, 4H); MS (ESI) (m/z): 406 [M+H]$^+$.

III-3

N-(1-(2-ethoxyethyl)-3-(pyridin-2-yl)-1H-pyrazol-4-yl)-2-(1H-pyrazol-4-yl)oxazole-4-carboxamide

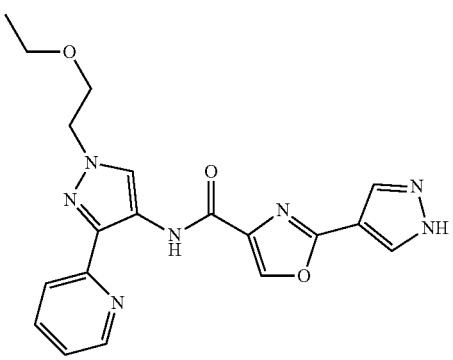 [SMILES: CCOCCn1cc(NC(=O)c2coc(-c3cn[nH]c3)n2)c(-c2ccccn2)n1]

$^1$HNMR (300 MHz, DMSO-d6) δ 12.02 (s, 1H), 8.86 (d, J=6.7 Hz, 2H), 8.74 (s, 1H), 8.44 (s, 1H), 8.34 (s, 1H), 8.01-7.90 (m, 2H), 7.42-7.38 (m, 1H), 4.37 (t, J=6.7 Hz, 2H), 3.79 (t, J=6.7 Hz, 2H), 3.46 (q, J=6.7 Hz, 2H), 1.09 (t, J=6.7 Hz, 3H); LCMS (m/z): 394.21 (MH+).

III-4

N-(1-((1s,3s)-3-ethoxycyclobutyl)-3-(pyridin-2-yl)-1H-pyrazol-4-yl)-2-(1H-pyrazol-4-yl)oxazole-4-carboxamide

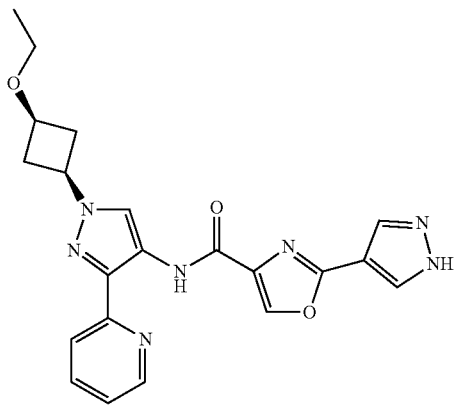 [SMILES: CCO[C@H]1C[C@@H](n2cc(NC(=O)c3coc(-c4cn[nH]c4)n3)c(-c3ccccn3)n2)C1]

$^1$HNMR (300 MHz, DMSO-d6) δ 12.01 (s, 1H), 8.86 (d, J=6.7 Hz, 1H), 8.74 (s, 1H), 8.45 (s, 1H), 8.33 (s, 1H), 8.06-8.03 (m, 1H), 7.97-7.92 (m, 1H), 7.43-7.39 (m, 1H), 4.65-4.59 (m, 1H), 3.87-3.82 (m, 1H), 3.42 (q, J=6.7 Hz, 2H), 2.86-2.77 (m, 2H), 2.45-2.41 (m, 1H), 1.15 (t, J=6.7 Hz, 3H); LCMS (m/z): 420.21 (MH$^+$).

III-5

N-(1-cyclobutyl-3-(pyridin-2-yl)-1H-pyrazol-4-yl)-2-(1H-pyrazol-4-yl)oxazole-4-carboxamide as formate salt

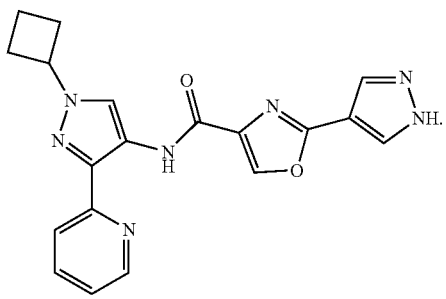

LCMS (m/z): 376.20 (MH$^+$)

III-6

N-(1-(2-(2-methoxyethoxy)ethyl)-3-(pyridin-2-yl)-1H-pyrazol-4-yl)-2-(1H-pyrazol-3-yl)oxazole-4-carboxamide

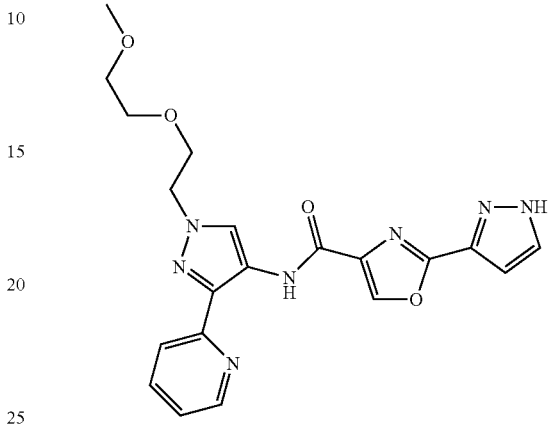

$^1$HNMR (300 MHz, DMSO-d6) δ 12.02 (s, 1H), 8.86 (d, J=6.7 Hz, 1H), 8.74 (s, 1H), 8.44 (s, 1H), 8.34 (s, 1H), 8.01-7.90 (m, 2H), 7.42-7.38 (m, 1H), 4.37 (t, J=6.7 Hz, 2H), 3.84 (t, J=6.7 Hz, 2H), 3.56-3.53 (m, 2H); 3.44-3.41 (m, 2H); 3.22 (s, 3H); LCMS (m/z): 424.24 (MH+).

III-7

N-(1-(2-(2,2-difluoroethoxy)ethyl)-3-(pyridin-2-yl)-1H-pyrazol-4-yl)-2-(1H-pyrazol-4-yl)oxazole-4-carboxamide $^1$H NMR (400 MHz, DMSO-d$_6$) δ 13.53 (s, 1H), 12.04 (s, 1H), 8.84 (ddd, J=5.0, 1.8, 1.0 Hz, 1H), 8.71 (s, 1H), 8.46 (s, 1H), 7.98 (dt, J=8.0, 1.1 Hz, 1H), 7.89 (ddd, J=8.1, 7.4, 1.8 Hz, 1H), 7.36 (ddd, J=7.4, 4.9, 1.3 Hz, 1H), 6.11 (tt, J=54.9, 3.7 Hz, 1H), 4.40 (t, J=5.2 Hz, 2H), 3.96 (t, J=5.3 Hz, 2H), 3.72 (td, J=15.2, 3.7 Hz, 2H). MS (ESI) (m/z): 430 [M+H]$^+$

Example 26

LPS Induced IL23p19 in THP-1 Cells (with IFNγ Primed) Assay

Materials and Equipment

THP-1 Cells (ATCC, Cat# TIB-202), Dimethyl Sulfoxide (DMSO) (Sigma-Aldrich, Cat# D2650), RPMI 1640 (Cellgro, Cat#10-040-CM), Fetal Bovine Serum (Sigma, Cat#F4135), Albumin From Bovine Serum (BSA) (Sigma-Aldrich, Cat#A7906), LPS (Serotype K-235, Sigma, Product Number L 2143), IFNγ (Peprotech, Cat#300-02) Capture antibody: Human IL-23p19 ELISA (e-Bioscience, Cat. #14-7238-85), Detection antibody: Primary Mouse Biotinylated anti-human IL-12(p40/p70) (e-Bioscience, Cat. #13-7129-85), Secondary HRP-conjugated Streptavidin (R&D Systems, Cat#DY998), 1×PBST Washing Buffer (PBS-Tween tablet) (VWR International, Cat#80058-558), ELISA Blocking Buffer (PBS with 1% BSA), ELISA Dilution Buffer (PBS with 1% BSA), 384 Well Flat-Bottom, MaxiSorp Black Immuno Plates (Thermo Scientific, Cat#12-565-346), 384 Well Flat-Bottom, White Tissue Culture Plates (Thermo Scientific, Cat#12-565-343), Super Signal ELISA Pico Chemiluminescent Substrate (Thermo Scientific, Cat#37070), Cell Titer Glo reagent (Promega, Cat#G7573), Positive control, IKK2VI inhibitor (Calbiochem, Cat#401483), AquaMax 4000 plate washer (Molecular Devices), Luminometer, Wallac Victor2 1420 Multilabel Counter.

Method

THP-1 Cells Stimulation:

On day 1, 50K/well THP-1 cells were seeded and primed with IFNγ (50 ng/mL) in 384-well plates for about 18 hours in RPMI media with 10% FBS. On day 2, the compound was serially diluted in DMSO from 5 mM in 3-fold dilutions, and then diluted 1:125 in RPMI media with 10% FBS. 50 µL/well 2× compound was added to 50 µL/well THP-1 cells (with IFNγ primed) in duplicate in 384 well tissue culture plates. The cells were pre-incubated with compound for 1 hour at 37° C., 5% $CO_2$ before addition of 10 µL/well 1×LPS to give a final concentration of 1 ug/mL LPS. Day 3, after stimulation for 18 hours at 37° C., 5% $CO_2$, the assay plate was centrifuged and 70 µL/well supernatant was harvested. IL-23p19 protein in 70 µL/well of supernatant was measured by sandwich ELISA, and 25 µl/well Cell Titer Glo reagent was added to the remaining cells to measure compound toxicity.

Human IL-23p19 Sandwich ELISA:

Maxisorp immuno ELISA plates were pre-coated with 25 µL/well of anti-IL-23p19 capture antibody (2.5 ug/mL) in PBS overnight at room temperature. After washing with 1× PBST, the plates were blocked using 100 L/well of 1% BSA in PBS for 2 hours at room temperature. The plates were washed three times with 1×PBST and 70 µL/well supernatant were added. The plates were incubated at room temperature for 2 hours with shaking and washed three times with 1×PBST. 25 µL/well of biotin labeled anti-IL-12(p40/p70) detection antibody (100 ng/mL) in PBS with 1% BSA was added and the plates were incubated at room temperature for 2 hours with shaking. After washing three times with 1×PBST, 25 µL/well of streptavidin-HRP (1:200) in PBS with 1% BSA was added and the plates were incubated at room temperature for 20 minutes with shaking. The plates were washed three times with 1× PBST and 25 µL/well of Super Signal ELISA Pico Chemiluminescent Substrate were added. The plates were read with a luminometer, and the chemiluminescence values were entered into Athena (Rigel) for curve fitting, $EC_{50}$ calculation, and database storage. The results are shown in Table 1.

Example 27

Compound Screening Using DC Cells

Materials

Human PBMC cells (All Cells, Cat No. PB002)

RPMI growth media containing 10% FBS

IFNγ (Peprotech, Cat No. 300-02)

GMCSF (Peprotech, Cat No. 300-03) and IL4 (Peprotech Cat No. 200-04)

White clear bottom 96 well plates (Fisher, Cat No. 07-200-587, Corning #3903)

LPS (Make 2.5 mg/ml Stock in PBS) from Sigma Aldrich (Cat No. L2018-5MG)

Cell Titer Glo reagent (Promega, Cat No. G7573)

Positive controls, IKK2VI inhibitor (Calbiochem, Cat No. 401483)

Protocol

I. Differentiation of PBMC's to DC Cells:

Human PBMC cells (400 million) obtained from the vendor were transferred into a T-175 flask containing 15 ml RPMI media (10% FBS) and incubate for 2 hours at 37° C. After 2 hours, the media including floating cells was aspirated out carefully and 12 ml of fresh RPMI media (10% FBS) containing GMCSF (100 ng/ml) and IL4 (20 ng/ml) was added, and the flask was kept in a 37° C. incubator for 7 days.

After 3 days, fresh GMCSF (100 ng/ml) and IL4 (20 ng/ml) were added to the flask and the incubation continued. After 7 days, the fully differentiated cells were harvested by spinning down (1200 rpm/5 min) and aspirating the media. The cells were suspended in fresh RPMI media (10% FBS) containing 50 ng/ml IFNγ (1000 U/ml) and then plated (50K/well in 100 µl) onto a white clear bottom 96 well plate and left in a 37° C. incubator for 24 hours.

II. Addition of Compounds:

After 24 hours incubation, 100 µl of RPMI media was added containing 2× concentrated test compound per well to the above cell-culture media (final concentration becomes 1×) and the plates were pre-incubated for 1 hour at 37° C. before stimulating with LPS.

After 1 hour compound pre-incubation, 10 µl per well of 20× concentrated LPS solution in RPMI media was added to give a final concentration of 1 µg/ml. The mixture was shaken and incubated the plates at 37° C. for an additional 18 hours.

155 µl of the supernatant was harvested from each well carefully (without the tip touching the bottom of the well) and to the remaining 50 µl/well of the cell culture plate was added 50 µl of Cell Titer Glo reagent. The mixture was incubated for 1-2 minutes on a shaker and the plate was read for luminescence intensity to determine the compound cytotoxicity. The cell culture supernatant collected above was used to carry out IL23 ELISA (65 µl -Supernatant) and IL10 ELISA (90 µl—Supernatant) as described below.

Example 28

Human IL-23 (p19/p40) ELISA Protocol (e-Biosciences)

Materials:

96-well high binding opaque white plates (from Pierce, Cat No. 15042); 1×PBS; 1×TBST washing buffer;

Blocking Solution: 0.5% Casein in PBS (from BDH, Cat No. 440203H);

Dilution Solution: 1% BSA in PBS (10% BSA from Fisher, Cat No. 37525);

Capture antibody: Rat anti-human IL-23 (p19) (e-Biosciences, Cat. No. 14-7238-85);

Detection antibody: Primary Mouse Biotinylated anti-human IL-12 (p40/p70) (e-biosciences, Cat No. 13-7129-85);

Secondary HRP-conjugated Streptavidin (R&D Systems, Cat No. DY998);

rHuman-IL-23 (e-biosciences, Cat No. 34-8239) (Suggested starting concentration=5 ng/ml in RPMI cell culture media);

Cell Culture Supernatant (65 µl from THP-1 cells primed with IFNγ (50 ng/ml-1000 U/ml) and stimulated with 0.01% SAC);

SuperSignal ELISA Pico Chemiluminescent substrate [Pierce, Cat No. 37069].

Coating Plates:

To 10.5 ml PBS add 50 µl of anti-IL23 (p19) was added capture antibody (2.5 µg/ml). The mixture was mixed well and 100 µl of the coating solution was added to each well of the 96 well white plates from Pierce. The wells were covered and incubated overnight at 4° C.

Blocking the Plates:

The anti-IL23 (p19)-antibody-coated plates were washed 2× using TBST (use plate washer) and blocked using 200 µl of 0.5% Casein for 1.5 to 2 hours at room temperature with shaking.

Addition of Supernatant and Detection:

The plates were washed 2× using TBST and the supernatant was transferred (65 µl/well) to the above pre-blocked/IL23(p19)-antibody-coated 96 well plate, and incubated at room temperature for 1.5 hours with shaking.

The plates were washed 4× using TBST (plate washer) and 100 l/well detection antibody solution prepared from 2 µl of biotin labeled anti-IL-12 (p40/p70) antibody in 11 ml 1% BSA/PBS solution (1-5000 dilution) was added. The plates were incubated for 1 hour with shaking at Room temperature.

Again, the plates were washed 4× with TBST and 100 µl of HRP labeled Streptavidin (R&D Systems) solution (10 µl/10 ml 1% BSA solution) was added, and the plates were incubated at room temperature for another 45 minutes with shaking.

After 45 minutes, the plates were washed with TBST 4× and 100 µl/well Super Signal ELISA Pico Chemiluminescent Substrate from Pierce (3.5 ml A+3.5 ml B+3.5 ml MQ water) was added. The plates were shaken for 1-2 minutes then read on a plate reader.

The $EC_{50}$ results from the assays described in Examples 26 and 28 are shown in Tables 1-3. A person of ordinary skill in the art understands that the assays described in Examples 26 and 28 are predictive for results from in vivo assays.

TABLE 1

| Compound | IL23-p19 ELISA, Dendritic, LPS, 10 pt, $EC_{50}$ (µM) | IL23-p19 ELISA, THPI1-IFNγ, LPS, 10 pt $EC_{50}$ (µM) |
|---|---|---|
| I-1 | 0.0334 | 0.0048 |
| I-2 | 0.0842 | 0.0343 |
| I-3 | 0.0033 | 0.0089 |
| I-4 | 0.0201 | 0.0063 |
| I-5 | 0.0102 | 0.012 |
| I-6 | ND* | 0.0196 |
| I-7 | 0.0757 | 0.028 |
| I-8 | 7.644 | 0.1871 |
| I-9 | 0.1716 | 0.0228 |
| I-10 | 0.0309 | 0.0699 |
| I-11 | 0.1794 | 0.0254 |
| I-12 | 2.404 | 0.1769 |
| I-13 | 0.1431 | 0.0341 |
| I-14 | ND* | 9.12 |
| I-15 | 0.4512 | 0.0853 |
| I-17 | 0.0156 | 0.0603 |
| I-18 | 0.0256 | 0.0833 |
| I-19 | Not tested | 20.34 |
| I-20 | 0.1347 | 0.0399 |
| I-21 | 0.1704 | 0.2433 |
| I-22 | 0.0369 | 0.0434 |
| I-23 | 0.071 | 0.2702 |
| I-24 | 0.2171 | 0.2377 |
| I-25 | 0.161 | 0.4003 |
| I-27 | 0.0641 | 0.0158 |
| I-28 | 0.1108 | 0.474 |
| I-29 | 0.2074 | 0.976 |
| I-30 | 0.0065 | 0.0028 |
| I-31 | 0.9727 | 0.6883 |
| I-32 | 0.4169 | 0.204 |
| I-33 | 0.0234 | 0.0591 |
| I-34 | 0.0188 | 0.0078 |
| I-35 | 0.0465 | 0.078 |
| I-36 | 0.0302 | 0.2604 |
| I-37 | Not tested | 0.0733 |
| I-38 | 0.0399 | 0.0026 |

*ND indicates that an accurate inhibition curve may not have been produced due to compound insolubility, artifacts in the assay, and/or other factors.

TABLE 2

| Compound | IL23-p19 ELISA, Dendritic, LPS, 10 pt, $EC_{50}$ (µM) | IL23-p19 ELISA, THP1-IFNγ, LPS, 10 pt $EC_{50}$ (µM) |
|---|---|---|
| II-1 | 0.0334 | 0.0048 |
| II-2 | 0.0842 | 0.0343 |
| II-3 | 0.0033 | 0.0089 |
| II-4 | 0.0201 | 0.0063 |
| II-5 | 0.0102 | 0.012 |
| II-6 | ND* | 0.0196 |
| II-7 | 0.0757 | 0.028 |
| II-8 | 7.644 | 0.1871 |
| II-9 | 0.1716 | 0.0228 |
| II-10 | 0.0309 | 0.0699 |
| II-11 | 0.1794 | 0.0254 |
| II-12 | 2.404 | 0.1769 |
| II-13 | 0.1431 | 0.0341 |
| II-14 | ND* | 9.12 |
| II-15 | 0.4512 | 0.0853 |
| II-17 | 0.0156 | 0.0603 |
| II-18 | 0.0256 | 0.0833 |
| II-20 | 0.0641 | 0.0158 |
| II-21 | 0.1108 | 0.474 |
| II-22 | 0.2074 | 0.976 |
| II-23 | 0.0065 | 0.0028 |
| II-24 | 0.9727 | 0.6883 |
| II-25 | 0.4169 | 0.204 |
| II-26 | 0.0234 | 0.0591 |
| II-27 | 0.0188 | 0.0078 |

TABLE 2-continued

| Compound | IL23-p19 ELISA, Dendritic, LPS, 10 pt, EC$_{50}$ (μM) | IL23-p19 ELISA, THP1-IFNγ, LPS, 10 pt EC$_{50}$ (μM) |
| --- | --- | --- |
| II-28 | 0.0465 | 0.078 |
| II-29 | 0.0302 | 0.2604 |
| II-30 | Not tested | 0.0733 |
| II-31 | 0.0399 | 0.0026 |

*ND indicates that an accurate inhibition curve may not have been produced due to compound insolubility, artifacts in the assay, and/or other factors.

TABLE 3

| Compound | IL23-p19 ELISA, Dendritic, LPS, 10 pt, EC$_{50}$ (μM) | IL23-p19 ELISA, THP1-IFNγ, LPS, 10 pt EC$_{50}$ (μM) |
| --- | --- | --- |
| III-1 | Not tested | 20.34 |
| III-2 | 0.1347 | 0.0399 |
| III-3 | 0.1704 | 0.2433 |
| III-4 | 0.0369 | 0.0434 |
| III-5 | 0.071 | 0.2702 |
| III-6 | 0.2171 | 0.2377 |
| III-7 | 0.161 | 0.4003 |

V. Exemplary Embodiments

The following numbered paragraphs illustrate exemplary embodiments of the disclosed technology.

Paragraph 1. A compound, having a formula 1

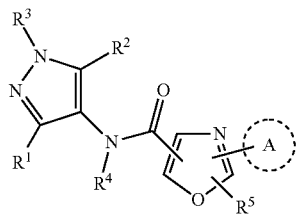

1 or a salt thereof, wherein:

at least one of $R^1$ and $R^2$ is aromatic, and the remaining $R^1$ or $R^2$ is H, alkyl, haloalkyl, nitro, cyano, amide, amino, hydroxyl, carboxyl, carboxyl ester, or acyl;

$R^3$ is H, aliphatic, heteroaliphatic, heterocyclyl, amide, aromatic, or araliphatic;

$R^4$ is H, aliphatic, heteroaliphatic, or one of $R^1$ or $R^2$ together with $R^4$, and together with the atoms to which they are attached, form a heterocyclic ring;

$R^5$ is H or aliphatic; and ring A is a heterocyclic ring.

Paragraph 2. The compound of paragraph 1, wherein one of $R^1$ and $R^2$ is a nitrogen-containing heteroaryl, and the other of $R^1$ and $R^2$ is H, alkyl, haloalkyl, nitro, cyano, amide, amino, hydroxyl, carboxyl, carboxyl ester, or acyl.

Paragraph 3. The compound of paragraphs 1 or 2, wherein one of $R^1$ and $R^2$ is pyridinyl, pyrimidinyl or pyrazinyl, and the other of $R^1$ and $R^2$ is H.

Paragraph 4. The compound of any of paragraphs 1-3, wherein $R^3$ is H, alkyl, cycloalkyl, heteroaliphatic, or heterocycloaliphatic.

Paragraph 5. The compound of any of paragraphs 1-4, wherein $R^3$ is H, $C_{1-6}$ alkyl, cyclopropyl, cyclobutyl, cyclopentyl or cyclohexyl.

Paragraph 6. The compound of any of paragraphs 1-4 wherein $R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, cyclohexyl, or cyclohexyl substituted with —OH, alkoxy or heterocycloaliphatic.

Paragraph 7. The compound of any of paragraphs 1-6, wherein $R^3$ is 4-ethoxycyclohexyl, 4-morpholinocyclohexyl, 3-ethoxycyclobutyl, 4-hydroxycyclohexyl, (2,6-dimethylmorpholino) cyclohexyl, 3-morpholinocyclobutyl, 4-(4-methylpiperazin-1-yl)cyclohexyl, or 3-hydroxycyclobutyl Paragraph 8. The compound according to any of paragraphs 1-7, wherein $R^4$ is H or $C_{1-6}$ alkyl.

Paragraph 9. The compound according to any of paragraphs 1-8, wherein:

one of $R^1$ and $R^2$ is selected from pyridinyl, pyrimidinyl or pyrazinyl, and the other of $R^1$ and $R^2$ is H;

$R^3$ is $C_{1-6}$alkyl, tetrahydropyran, unsubstituted heteroaliphatic, heteroaliphatic substituted with halogen, unsubstituted cyclobutyl, cyclobutyl substituted with alkoxy, cyclohexyl, or cyclohexyl substituted with —OH, alkoxy or heterocycloaliphatic; and $R^4$ is H.

Paragraph 10. The compound according to any of paragraphs 1-9, wherein $R^5$ is H, alkyl, or haloalkyl.

Paragraph 11. The compound according to any of paragraphs 1-10, wherein $R^5$ is H or $C_{1-6}$ alkyl.

Paragraph 12. The compound according to any of paragraphs 11, wherein:

one of $R^1$ and $R^2$ is selected from pyridinyl, pyrimidinyl or pyrazinyl, and the other of $R^1$ and $R^2$ is H;

$R^3$ is $C_{1-6}$alkyl, tetrahydropyran, unsubstituted heteroaliphatic, heteroaliphatic substituted with halogen, unsubstituted cyclobutyl, cyclobutyl substituted with alkoxy, cyclohexyl, or cyclohexyl substituted with —OH, alkoxy or heterocycloaliphatic;

$R^4$ is H; and $R^5$ is H.

Paragraph 13. The compound according to any of paragraphs 1-12, wherein ring A is heteroaryl.

Paragraph 14. The compound according to paragraph 13, wherein ring A is a nitrogen-containing heteroaryl.

Paragraph 15. The compound according to paragraph 13, wherein ring A is a 5-membered nitrogen-containing heteroaryl.

Paragraph 16. The compound according to paragraph 13, wherein ring A is pyrazolyl.

Paragraph 17. The compound according to any of paragraphs 13-16, wherein ring A is unsubstituted.

Paragraph 18. The compound according to any of paragraphs 13-16, wherein ring A is substituted with from 1 to 4 substituents.

Paragraph 19. The compound according to paragraph 18, wherein ring A is substituted with at least one substituent selected from halogen, an aliphatic substituent, an alkylphosphate, or an alkylphosphonate.

Paragraph 20. The compound according to any of paragraphs 13-18, wherein: one of $R^1$ and $R^2$ is selected from pyridinyl, pyrimidinyl or pyrazinyl, and the other of $R^1$ or $R^2$ is H;

$R^3$ is $C_{1-6}$alkyl, tetrahydropyran, unsubstituted heteroaliphatic, heteroaliphatic substituted with halogen, unsubstituted cyclobutyl, cyclobutyl substituted with OH, alkoxy or heterocycloaliphatic, unsubstituted cyclohexyl, or cyclohexyl substituted with —OH, alkoxy or heterocycloaliphatic;

$R^4$ is H;

$R^5$ is H; and ring A is pyrazolyl.

Paragraph 21. The compound of any of paragraphs 1-20, having a formula 2

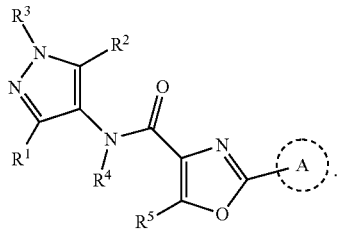

Paragraph 22. The compound of paragraph 21, wherein:

one of $R^1$ and $R^2$ is selected from pyridinyl, pyrimidinyl or pyrazinyl, and the other of $R^1$ or $R^2$ is H;

$R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, unsubstituted cyclohexyl, or cyclohexyl substituted with —OH, alkoxy or heterocycloaliphatic;

$R^4$ is H or $C_{1-6}$ alkyl;

$R^5$ is H or $C_{1-6}$ alkyl; and ring A is pyrazolyl.

Paragraph 23. The compound of any of paragraphs 1-22, having a formula 3

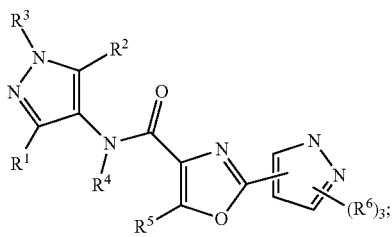

and each $R^6$ independently is H, aliphatic, heteroaliphatic, aryl, —O-aliphatic, araliphatic, heterocyclyl, sulfonyl, halogen, nitro, OH, haloalkyl, carboxyl ester, cyano, acyl, amino, alkyl phosphate or alkylphosphonate.

Paragraph 24. The compound according to paragraph 23, wherein: one of $R^1$ and $R^2$ is selected from pyridinyl, pyrimidinyl or pyrazinyl, and the other of $R^1$ and $R^2$ is H;

$R^3$ is $C_{1-6}$alkyl, tetrahydropyran, unsubstituted heteroaliphatic, heteroaliphatic substituted with halogen, unsubstituted cyclobutyl, cyclobutyl substituted with —OH, alkoxy or heterocycloaliphatic, unsubstituted cyclohexyl, or cyclohexyl substituted with —OH, alkoxy or heterocycloaliphatic;

$R^4$ is H or $C_{1-6}$ alkyl;

$R^5$ is H or $C_{1-6}$ alkyl; and ring A is pyrazolyl.

Paragraph 25. The compound of any one of paragraphs 1-24, wherein the compound has a formula 4

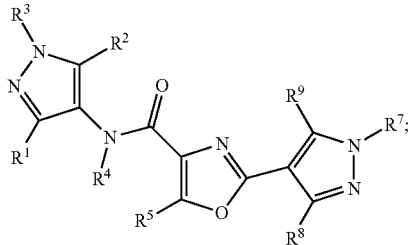

and each of $R^7$, $R^8$, and $R^9$ independently is H, aliphatic, heteroaliphatic, aryl, —O-aliphatic, araliphatic, heterocyclyl, halogen, sulfonyl, nitro, OH, haloalkyl, carboxyl ester, cyano, acyl, amino, alkyl phosphate or alkylphosphonate.

Paragraph 26. The compound of paragraph 25, wherein $R^7$ is H, alkyl, carboxyl ester, acyl, alkyl phosphate, alkyl phosphonate, heterocycloalkyl or aralkyl.

Paragraph 27. The compound of any of paragraphs 25-26, wherein $R^7$ is H, or —$CH_2OP(O)(OH)_2$ or a salt thereof.

Paragraph 28. The compound of any one of paragraphs 25-27, wherein each of $R^8$ and $R^9$ independently is H, halogen, alkyl or haloalkyl.

Paragraph 29. The compound of paragraph 28, wherein $R^8$ and $R^9$ are H.

Paragraph 30. The compound of paragraph 28, wherein one of $R^8$ and $R^9$ is F and the other is H.

Paragraph 31. The compound of any of paragraphs 25-30, wherein: one of $R^1$ and $R^2$ is selected from pyridinyl, pyrimidinyl or pyrazinyl, and the other of $R^1$ or $R^2$ is H;

$R^3$ is $C_{1-6}$alkyl, tetrahydropyran, unsubstituted heteroaliphatic, heteroaliphatic substituted with halogen, unsubstituted cyclobutyl, cyclobutyl substituted with alkoxy, cyclohexyl, or cyclohexyl substituted with —OH, alkoxy or heterocycloaliphatic;

$R^4$ is H or $C_{1-6}$ alkyl;

$R^5$ is H or $C_{1-6}$ alkyl; and ring A is pyrazolyl.

Paragraph 32. The compound of any one of paragraphs 1-31, wherein: one of $R^1$ and $R^2$ is heteroaryl, and the remaining $R^1$ or $R^2$ is H, alkyl, haloalkyl, nitro, cyano, amide, amino, hydroxyl, carboxyl, carboxyl ester, or acyl;

$R^3$ is $R^a$, $R^b$, $R^a$ substituted with 1, 2, or 3 $R^b$, $R^a$ substituted with $R^b$ and $R^c$, $R^a$ substituted with $R^c$, —$(CR^aR^a)_n$—$R^a$, —$(CH_2)_n$—$R^a$, —$(CR^aR^a)_n$—$R^b$, —$(CH_2)_n$—$R^b$, —$[(CH_2)_m$—O—$]_n$—$R^a$, —$[(CH_2)_m$—O—$]_n$-[$R^a$ substituted with 1, 2 or 3 $R^b$], or —$(CH_2)_m$—O—$(CH_2)_m$—O—$R^a$ wherein each m and n independently are 1, 2 or 3;

$R^4$ is $R^a$, —$(CR^aR^a)_m$—O—$R^a$, —$(CH_2)_m$—O—$R^a$, —$(CR^aR^a)_m$—O—$(CR^aR^a)_n$—O—$R^a$, —$[(CH_2)_m$—O—$]_n$—$R^a$ or —$(CH_2)_m$—O—$(CH_2)_m$—O—$R^a$ wherein each m and n independently are 1, 2 or 3;

$R^5$ is $R^a$ or Rb;

$R^a$ is independently for each occurrence H, D, $C_{1-6}$alkyl, $C_{1-6}$haloalkyl $C_{3-6}$cycloalkyl, $C_{3-6}$heteroalicyclyl,

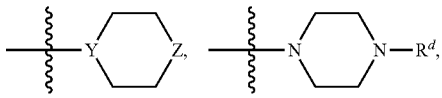

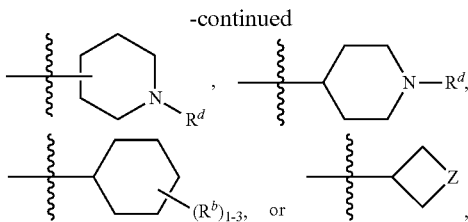

where Y and Z independently are —CH$_2$, —CHR$^b$, O or NR$^d$;

R$^b$ is independently for each occurrence —OH, —CF$_3$, —OR$^c$, —NR$^d$R$^d$, or halogen;

R$^c$ is independently for each occurrence C$_{1-6}$alkyl, C$_{3-6}$heteroalicyclyl, C$_{1-6}$alkyl substituted with 1, 2 or 3 R$^e$, C$_{3-6}$cycloalkyl substituted with 1, 2 or 3 R$^e$, or C$_{3-6}$heteroalicyclyl substituted with 1, 2 or 3 R$^e$;

R$^d$ is independently for each occurrence H, C$_{1-6}$alkyl optionally substituted with 1, 2 or 3 R$^e$, or two R$^d$ groups together with the nitrogen bound thereto form a C$_{3-6}$heteroalicyclyl moiety optionally substituted with C$_{1-6}$alkyl and optionally interrupted with one or two —O— or —N(R$^g$) wherein R$^g$ is R$^{70}$; and R$^e$ is independently for each occurrence C$_{1-6}$alkyl, or —OR$^a$.

Paragraph 33. The compound according to paragraph 23, wherein:

one of R$^1$ and R$^2$ is heteroaryl, and the remaining R$^1$ or R$^2$ is H, alkyl, haloalkyl, nitro, cyano, amide, amino, hydroxyl, carboxyl, carboxyl ester, or acyl;

R$^3$ is R$^a$, R$^b$, R$^a$ substituted with 1, 2, or 3 R$^b$, R$^a$ substituted with R$^b$ and R$^c$, R$^a$ substituted with R$^c$, —(CR$^a$R$^a$)$_n$—R$^a$, —(CH$_2$)$_n$—R$^a$, —(CR$^a$R$^a$)$_n$—R$^b$, —(CH$_2$)$_n$—R$^b$, —[(CH$_2$)$_m$—O—]$_n$—R$^a$, —[(CH$_2$)$_m$—O—]$_n$-[R$^a$ substituted with 1, 2 or 3 R$^b$], or —(CH$_2$)$_m$—O—(CH$_2$)$_m$—O—R$^a$ wherein each m and n independently are 1, 2 or 3;

R$^4$ is R$^a$, —(CR$^a$R$^a$)$_m$—O—R$^a$, —(CH$_2$)$_m$—O—R$^a$, —(CR$^a$R$^a$)$_m$—O—(CR$^a$R$^a$)$_m$—O—R$^a$, —[(CH$_2$)$_m$—O—]$_n$—R$^a$ or —(CH$_2$)$_m$—O—(CH$_2$)$_m$—O—R$^a$ wherein each m and n independently are 1, 2 or 3;

R$^5$ is R$^a$ or R$^b$;

R$^6$ is R$^a$, R$^b$, R$^a$ substituted with —OP(O)(R$^f$)$_2$, R$^a$ substituted with 1, 2 or 3 R$^b$, R$^a$ substituted with R$^c$, R$^a$ substituted with C$_{1-6}$cycloalkyl, R$^a$ substituted with —P(O)(R$^f$)$_2$, aralkyl, —(CR$^a$R$^a$)$_n$—R$^a$, —(CH$_2$)$_n$—R$^a$ or —C(O)C(R$^a$)$_2$NR$^a$R$^b$;

n and m independently are 1, 2 or 3;

R$^a$ is independently for each occurrence H, D, C$_{1-6}$alkyl, C$_{1-6}$haloalkyl C$_{3-6}$cycloalkyl, C$_{3-6}$heteroalicyclyl,

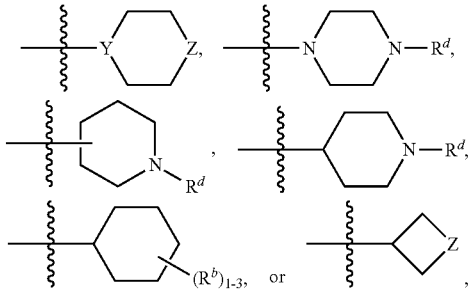

where Y and Z independently are —CH$_2$, —CHR$^b$, O or NR$^d$;

R$^b$ is independently for each occurrence —OH, —CF$_3$, —OR$^c$, —NR$^d$R$^d$, or halogen;

R$^c$ is independently for each occurrence C$_{1-6}$alkyl, C$_{3-6}$heteroalicyclyl, C$_{1-6}$alkyl substituted with 1, 2 or 3 R$^e$, C$_3$ 6cycloalkyl substituted with 1, 2 or 3 R$^e$, or C$_3$ 6heteroalicyclyl substituted with 1, 2 or 3 R$^e$;

R$^d$ is independently for each occurrence H, C$_{1-6}$alkyl optionally substituted with 1, 2 or 3 Re, or two R$^d$ groups together with the nitrogen bound thereto form a C$_3$ 6heteroalicyclyl moiety optionally substituted with C$_{1-6}$alkyl and optionally interrupted with one or two —O— or —N(R$^g$) wherein R$^g$ is R$^{70}$;

R$^e$ is independently for each occurrence C$_{1-6}$alkyl or —OR$^a$; and

R$^f$ is independently for each occurrence —OR$^a$, —O$^-$M$^+$ where each M$^+$ independently is an alkali metal ion or an ammonium ion.

Paragraph 34. The compound of paragraph 25, wherein:

one of R$^1$ and R$^2$ is heteroaryl, and the remaining R$^1$ or R$^2$ is H, alkyl, haloalkyl, nitro, cyano, amide, amino, hydroxyl, carboxyl, carboxyl ester, or acyl;

R$^3$ is R$^a$, R$^b$, R$^a$ substituted with 1, 2, or 3 R$^b$, R$^a$ substituted with R$^b$ and R$^c$, R$^a$ substituted with R$^c$, —(CR$^a$R$^a$)$_n$—R$^a$, —(CH$_2$)$_n$—R$^a$, —(CR$^a$R$^a$)$_n$—R$^b$, —(CH$_2$)$_n$—R$^b$, —[(CH$_2$)$_m$—O—]$_n$—R$^a$, —[(CH$_2$)$_m$—O—]$_n$-[R$^a$ substituted with 1, 2 or 3 R$^b$], or —(CH$_2$)$_m$—O—(CH$_2$)$_n$—O—R$^a$ wherein each m and n independently are 1, 2 or 3;

R$^4$ is R$^a$, —(CR$^a$R$^a$)$_m$—O—R$^a$, —(CH$_2$)$_m$—O—R$^a$, —(CR$^a$R$^a$)$_m$—O—(CR$^a$R$^a$)$_m$—O—R$^a$, —[(CH$_2$)$_m$—O—]$_n$—R$^a$ or —(CH$_2$)$_m$—O—(CH$_2$)$_m$—O—R$^a$ wherein each m and n independently are 1, 2 or 3;

R$^5$ is R$^a$ or R$^b$;

R$^6$ is R$^a$, R$^b$, R$^a$ substituted with —OP(O)(R$^f$)$_2$, R$^a$ substituted with 1, 2 or 3 R$^b$, R$^a$ substituted with R$^c$, R$^a$ substituted with C$_{1-6}$cycloalkyl, R$^a$ substituted with —P(O)(R$^f$)$_2$, aralkyl, —(CR$^a$R$^a$)$_n$—R$^a$, —(CH$_2$)$_n$—R$^a$ or —C(O)C(R$^a$)$_2$NR$^a$R$^b$;

R$^7$ is R$^a$, R$^b$, R$^a$ substituted with —OP(O)(R$^f$)$_2$, R$^a$ substituted with 1, 2 or 3 R$^b$, R$^a$ substituted with R$^c$, R$^a$ substituted with —P(O)(R$^f$)$_2$, aralkyl, —(CR$^a$R$^a$)$_n$—R$^a$, —(CH$_2$)$_n$—R$^a$ or —C(O)C(R$^a$)$_2$NR$^a$R$^b$;

R$^8$ and R$^9$ independently are R$^a$ or R$^b$;

n and m independently are 1, 2 or 3;

R$^a$ is independently for each occurrence H, D, C$_{1-6}$alkyl, C$_{1-6}$haloalkyl C$_{3-6}$cycloalkyl, C$_{3-6}$heteroalicyclyl,

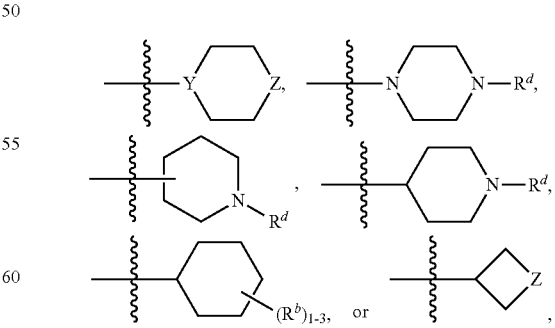

where Y and Z independently are —CH$_2$, —CHR$^b$, O or NR$^d$;

R$^b$ is independently for each occurrence —OH, —CF$_3$, —OR$^c$, —NR$^d$R$^d$, or halogen;

$R^c$ is independently for each occurrence $C_{1-6}$alkyl, $C_{3-6}$heteroalicyclyl, $C_{1-6}$alkyl substituted with 1, 2 or 3 $R^e$, $C_{3-6}$cycloalkyl substituted with 1, 2 or 3 $R^e$, or $C_{3-6}$heteroalicyclyl substituted with 1, 2 or 3 $R^e$;

$R^d$ is independently for each occurrence H, $C_{1-6}$alkyl optionally substituted with 1, 2 or 3 $R^e$, or two $R^d$ groups together with the nitrogen bound thereto form a $C_{3-6}$heteroalicyclyl moiety optionally substituted with $C_{1-6}$alkyl and optionally interrupted with one or two —O— or —N($R^g$) wherein $R^g$ is $R^{70}$;

$R^e$ is independently for each occurrence $C_{1-6}$alkyl, or —$OR^a$; and $R^f$ is independently for each occurrence —$OR^a$, —$O^-M^+$ where each $M^+$ independently is an alkali metal ion or an ammonium ion.

Paragraph 35. The compound of any one of paragraphs 1-34, wherein one of $R^1$ and $R^2$ is pyrimidin-2-yl, pyrimidin-4-yl, pyrazine-2-yl, 6-(difluoromethyl)pyridin-2-yl, 3-fluoro-6-(trifluoromethyl)pyridin-2-yl, 3,6-difluoropyridin-2-yl, or 3,5-difluoropyridin-2-yl.

Paragraph 36. The compound of any one of paragraphs 1-35, wherein the compound is not
2-(1-(cyclopropylmethyl)-1H-pyrazol-4-yl)-N-(1-methyl-3-(pyridin-2-yl)-1H-pyrazol-4-yl)oxazole-4-carboxamide;
2-(1H-pyrazol-4-yl)-N-(3-(pyridin-2-yl)-1-(tetrahydro-2H-pyran-4-yl)-1H-pyrazol-4-yl)oxazole-4-carboxamide;
N-(1-(2-ethoxyethyl)-3-(pyridin-2-yl)-1H-pyrazol-4-yl)-2-(1H-pyrazol-4-yl)oxazole-4-carboxamide;
N-(1-((1s,3s)-3-ethoxycyclobutyl)-3-(pyridin-2-yl)-1H-pyrazol-4-yl)-2-(1H-pyrazol-4-yl)oxazole-4-carboxamide;
N-(1-cyclobutyl-3-(pyridin-2-yl)-1H-pyrazol-4-yl)-2-(1H-pyrazol-4-yl)oxazole-4-carboxamide;
N-(1-(2-(2-methoxyethoxy)ethyl)-3-(pyridin-2-yl)-1H-pyrazol-4-yl)-2-(1H-pyrazol-4-yl)oxazole-4-carboxamide;
N-(1-(2-(2,2-difluoroethoxy)ethyl)-3-(pyridin-2-yl)-1H-pyrazol-4-yl)-2-(1H-pyrazol-4-yl)oxazole-4-carboxamide;
N-(3-carbamoyl-1-(tetrahydro-2H-pyran-4-yl)-1H-pyrazol-4-yl)-2-(1H-pyrazol-4-yl)oxazole-4-carboxamide;
2-(1H-pyrazol-3-yl)-N-(3-(pyridin-2-yl)-1-(2-(2,2,2-trifluoroethoxy)ethyl)-1H-pyrazol-4-yl)oxazole-4-carboxamide; or
N-(1-(2-(2-methoxyethoxy)ethyl)-3-(pyridin-2-yl)-1H-pyrazol-4-yl)-2-(1H-pyrazol-3-yl)oxazole-4-carboxamide.

Paragraph 37. A compound, selected from I-1 to I-39, as disclosed herein.

Paragraph 38. A compound, selected from II-1 to 11-32, as disclosed herein.

Paragraph 39. A compound, selected from III-1 to 111-7, as disclosed herein.

Paragraph 40. A composition, comprising a compound of any one of paragraphs 1-39, and a pharmaceutically acceptable excipient.

Paragraph 41. The composition of paragraph 40, further comprising an additional therapeutic agent.

Paragraph 42. A method, comprising administering to a subject in need thereof an effective amount of a compound of any one of paragraphs 1-39, or a composition of any one of paragraphs 40-41.

Paragraph 43. The method of paragraph 42, for treating a disease or condition for which an IRAK inhibitor is indicated.

Paragraph 44. The method of paragraph 43, wherein the disease is an auto-immune disease, inflammatory disorder, cardiovascular disease, neurodegenerative disorder, allergic disorder, multi-organ failure, kidney disease, platelet aggregation, cancer, transplantation, sperm motility, erythrocyte deficiency, graft rejection, lung injury, respiratory disease, ischemic condition, bacterial infection, viral infection, immune regulatory disorder or a combination thereof.

Paragraph 45. The method of paragraph 43, wherein the disease is amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, pancreatitis, Kaposi's sarcoma, myelodysplastic syndrome, Wegener's granulomatosis, ichthyosis, Graves ophthalmopathy or asthma.

Paragraph 46. The method of paragraph 44, wherein the immune regulatory disorder is rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracts, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

Paragraph 47. A method for inhibiting an IRAK protein, comprising contacting the IRAK protein with an effective amount of a compound of any one of paragraphs 1-39, or a composition of any one of paragraphs 40-41.

Paragraph 48. The method of paragraph 46, wherein the compound has an $EC_{50}$ of from greater than 0 to 5 µM.

Paragraph 49. The method of paragraph 46, wherein the compound has an $EC_{50}$ of from greater than 0 to 1 µM.

Paragraph 50. The method of any one of paragraphs 47-49, wherein the IRAK protein is in a subject.

Paragraph 51. The method of any one of paragraphs 47-50, wherein contacting the IRAK protein comprises contacting the IRAK protein in vitro.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound, having a formula

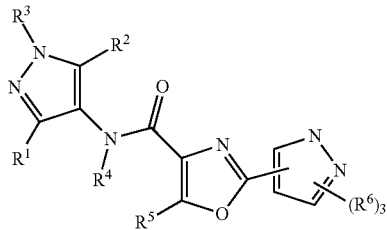

and/or a salt thereof, wherein:
at least one of $R^1$ and $R^2$ is heteroaryl, and the remaining $R^1$ or $R^2$ is H, alkyl, or haloalkyl;
$R^3$ is H, aliphatic, heteroaliphatic, heterocyclyl, amide, aromatic, or araliphatic;
$R^4$ is H or alkyl;
$R^5$ is H or alkyl; and
each $R^6$ independently is H, alkyl, haloalkyl, halogen, alkyl phosphate or alkylphosphonate.

2. The compound of claim 1, wherein $R^1$ is heteroaryl and $R^2$ is H.

3. The compound of claim 1, wherein at least one of $R^1$ and $R^2$ is nitrogen-containing heteroaryl.

4. The compound of claim 1, wherein at least one of $R^1$ and $R^2$ is 6-membered heteroaryl.

5. The compound of claim 1, wherein $R^3$ is $R^a$, $R^b$,$R^a$ substituted with 1, 2, or 3 $R^b$, $R^a$ substituted with $R^b$ and $R^c$, $R^a$ substituted with $R^c$, —$(CR^aR^a)_n$—$R^a$, —$(CH_2)_n$—$R^a$, —$(CR^aR^a)_n$—$R^b$, —$(CH_2)_n$—$R^b$, —$[(CH_2)_m$—O—$]_n$—$R^a$, —$[(CH_2)_m$—O—$]_n$—$[R^a$ substituted with 1, 2 or 3 $R^b]$, or —$(CH_2)_m$—O—$(CH_2)_m$—O—$R^a$ wherein each m and n independently are 1, 2 or 3;
$R^a$ is independently for each occurrence H, D, $C_{1-6}$alkyl, $C_{1-6}$haloalkyl $C_{3-6}$cycloalkyl, $C_{3-6}$heteroalicyclyl,

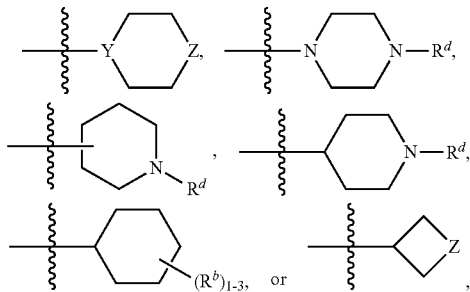

where Y and Z independently are —$CH_2$, —$CHR^b$, O or $NR^d$;
$R^b$ is independently for each occurrence —OH, —$CF_3$, —$OR^c$, —$NR^dR^d$, or halogen;
$R^c$ is independently for each occurrence $C_{1-6}$alkyl, $C_{3-6}$heteroalicyclyl, $C_{1-6}$alkyl substituted with 1, 2 or 3 $R^e$, $C_{3-6}$cycloalkyl substituted with 1, 2 or 3 $R^e$, or $C_{3-6}$heteroalicyclyl substituted with 1, 2 or 3 $R^e$;
$R^d$ is independently for each occurrence H, $C_{1-6}$alkyl optionally substituted with 1, 2 or 3 $R^e$, or two $R^d$ groups together with the nitrogen bound thereto form a $C_{3-6}$heteroalicyclyl moiety optionally substituted with $C_{1-6}$alkyl and optionally interrupted with one or two —O— or —$N(R^g)$ wherein $R^g$ is $R^{70}$; and
$R^e$ is independently for each occurrence $C_{1-6}$alkyl, or —$OR^a$.

6. The compound of claim 5, wherein each $R^6$ independently is H, halogen, alkyl, or $R^a$ substituted with —OP(O)$(R^f)_2$, and $R^f$ is independently for each occurrence —$OR^a$, —$O^-M^+$ where each $M^+$ independently is an alkali metal ion or an ammonium ion.

7. The compound of claim 1, wherein the compound, and/or salt thereof, has a formula

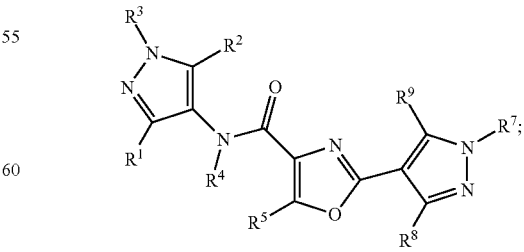

$R^7$ is H, alkyl, alkyl phosphate or alkylphosphonate; and
each of $R^8$ and $R^9$ is independently H, alkyl, haloalkyl, halogen.

8. The compound of claim 7, wherein one of $R^8$ and $R^9$ is H and the other of $R^8$ and $R^9$ is H or F.

9. The compound of claim 7, wherein $R^7$ is H.

10. The compound of claim 7, wherein $R^7$ is $CH_2OP(=O)(OR')_2$, and each OR' independently is OH, —Oalkyl, or $—O^-M^+$ where $M^+$ is a positive counter ion.

11. The compound of claim 1, wherein $R^1$ is

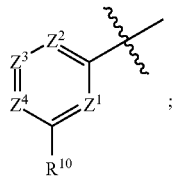

each of $Z^1$, $Z^2$, $Z^3$ and $Z^4$ independently is N or $CR^{10}$, where at least one of $Z^1$, $Z^2$, $Z^3$ and $Z^4$ is N; and
each $R^{10}$ independently is H, halogen, or aliphatic.

12. The compound of claim 11, wherein the compound, and/or a salt thereof, has a formula

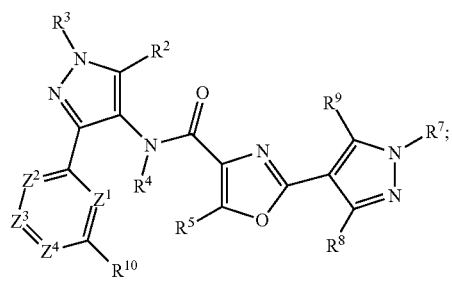

$R^7$ is H, alkyl, alkyl phosphate or alkylphosphonate; and each of $R^8$ and $R^9$ is independently H, alkyl, haloalkyl, halogen.

13. The compound of claim 12, wherein the compound, and/or salt thereof, has a formula selected from

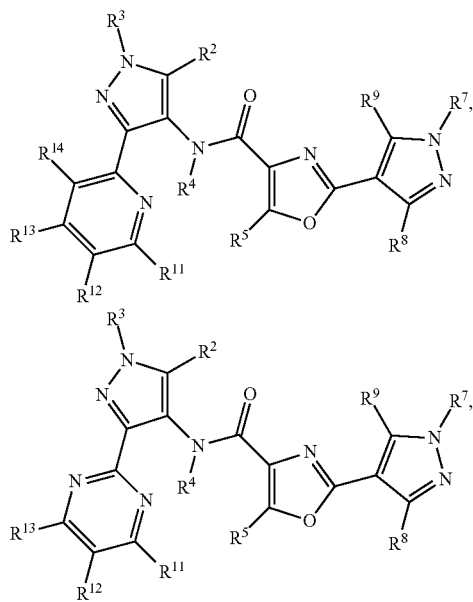

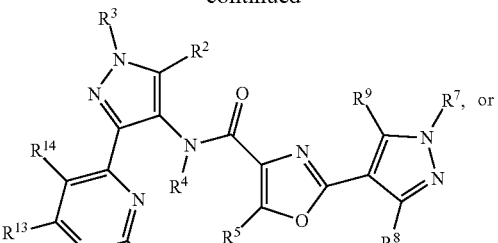

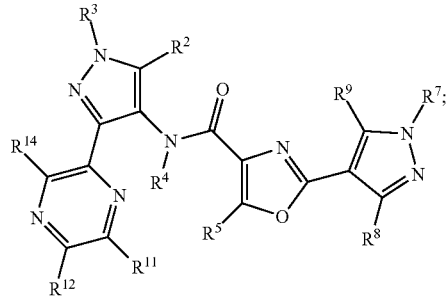

and
$R^{11}$, $R^{12}$, $R^{13}$, and $R^{14}$, if present, are independently H, halogen, or alkyl.

14. The compound of claim 13, wherein the compound has a formula

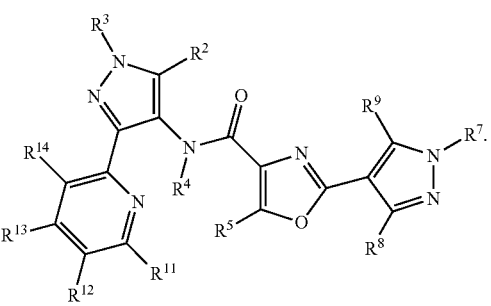

15. The compound of claim 14, wherein $R^{11}$, $R^{12}$, $R^{13}$, and $R^{14}$ independently is H, F, $CF_3$, or $CF_2$.

16. The compound of claim 15, wherein $R^2$, $R^4$ and $R^5$ are H.

17. The compound of claim 16, wherein $R^3$ is H, alkyl, cycloalkyl, heteroaliphatic, or heterocycloaliphatic.

18. The compound of claim 16, wherein $R^3$ is $C_{1-6}$alkyl, tetrahydropyran, unsubstituted heteroaliphatic, heteroaliphatic substituted with halogen, unsubstituted cyclobutyl, cyclobutyl substituted with OH, alkoxy, or heterocycloaliphatic, unsubstituted cyclohexyl, or cyclohexyl substituted with —OH, alkoxy or heterocycloaliphatic.

19. A compound, selected from:

I-1: N-(1-((1r,4r)-4-ethoxycyclohexyl)-3-(pyrazin-2-yl)-1H-pyrazol-4-yl)-2-(1H-pyrazol-4-yl)oxazole-4-carboxamide;

I-2: N-(1-((1r,4r)-4-morpholinocyclohexyl)-3-(pyrimidin-2-yl)-1H-pyrazol-4-yl)-2-(1H-pyrazol-4-yl)oxazole-4-carboxamide;

I-3: N-(1-((1r,4r)-4-ethoxycyclohexyl)-3-(pyrimidin-2-yl)-1H-pyrazol-4-yl)-2-(1H-pyrazol-4-yl)oxazole-4-carboxamide;

I-4: N-(3-(6-(difluoromethyl)pyridin-2-yl)-1-((1r,4r)-4-morpholinocyclohexyl)-1H-pyrazol-4-yl)-2-(1H-pyrazol-4-yl)oxazole-4-carboxamide;

I-5: N-(3-(6-(difluoromethyl)pyridin-2-yl)-1-((1R,4r)-4-((2R,6S)-2,6-dimethylmorpholino)cyclohexyl)-1H-pyrazol-4-yl)-2-(1H-pyrazol-4-yl)oxazole-4-carboxamide;

I-6: N-(1-((1r,4r)-4-ethoxycyclohexyl)-3-(pyrimidin-4-yl)-1H-pyrazol-4-yl)-2-(1H-pyrazol-4-yl)oxazole-4-carboxamide;

I-7: N-(3-(3-fluoro-6-(trifluoromethyl)pyridin-2-yl)-1-((1r,4r)-4-morpholinocyclohexyl)-1H-pyrazol-4-yl)-2-(1H-pyrazol-4-yl)oxazole-4-carboxamide;

I-8: sodium (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl)methyl phosphate;

I-9: N-(3-(3,6-difluoropyridin-2-yl)-1-((1r,4r)-4-ethoxycyclohexyl)-1H-pyrazol-4-yl)-2-(1H-pyrazol-4-yl)oxazole-4-carboxamide;

I-10: N-(3-(3,6-difluoropyridin-2-yl)-1-((1s,3s)-3-ethoxycyclobutyl)-1H-pyrazol-4-yl)-2-(1H-pyrazol-4-yl)oxazole-4-carboxamide;

I-11: N-(3-(3,6-difluoropyridin-2-yl)-1-((1r,4r)-4-hydroxycyclohexyl)-1H-pyrazol-4-yl)-2-(1H-pyrazol-4-yl)oxazole-4-carboxamide;

I-12: (4-(4-((3-(3,6-difluoropyridin-2-yl)-1-((1r,4r)-4-ethoxycyclohexyl)-1H-pyrazol-4-yl)carbamoyl)oxazol-2-yl)-1H-pyrazol-1-yl)methyl dihydrogen phosphate;

I-13: N-(3-(3,5-difluoropyridin-2-yl)-1-((1r,4r)-4-ethoxycyclohexyl)-1H-pyrazol-4-yl)-2-(1H-pyrazol-4-yl)oxazole-4-carboxamide;

I-14: N-(5-(3,6-difluoropyridin-2-yl)-1-((1r,4R)-4-ethoxycyclohexyl)-1H-pyrazol-4-yl)-2-(1H-pyrazol-4-yl)oxazole-4-carboxamide;

I-15: 2-(1H-pyrazol-4-yl)-N-(3-(pyridin-2-yl)-1-(2-(2,2,2-trifluoroethoxy)ethyl)-1H-pyrazol-4-yl)oxazole-4-carboxamide;

I-16: di-tert-butyl ((4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl) phosphate;

I-17: (4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl dihydrogen phosphate;

I-18: sodium (4-(4-((1-((1r,4r)-4-ethoxycyclohexyl)-3-(pyrazin-2-yl)-1H-pyrazol-4-yl)carbamoyl)oxazol-2-yl)-1H-pyrazol-1-yl)methyl phosphate;

I-19: 2-(1-(cyclopropylmethyl)-1H-pyrazol-4-yl)-N-(1-methyl-3-(pyridin-2-yl)-1H-pyrazol-4-yl)oxazole-4-carboxamide;

I-20: 2-(1H-pyrazol-4-yl)-N-(3-(pyridin-2-yl)-1-(tetrahydro-2H-pyran-4-yl)-1H-pyrazol-4-yl)oxazole-4-carboxamide;

I-21: N-(1-(2-ethoxyethyl)-3-(pyridin-2-yl)-1H-pyrazol-4-yl)-2-(1H-pyrazol-4-yl)oxazole-4-carboxamide;

I-22: N-(1-((1s,3s)-3-ethoxycyclobutyl)-3-(pyridin-2-yl)-1H-pyrazol-4-yl)-2-(1H-pyrazol-4-yl)oxazole-4-carboxamide;

I-23: N-(1-cyclobutyl-3-(pyridin-2-yl)-1H-pyrazol-4-yl)-2-(1H-pyrazol-4-yl)oxazole-4-carboxamide;

I-24: N-(1-(2-(2-methoxyethoxy)ethyl)-3-(pyridin-2-yl)-1H-pyrazol-4-yl)-2-(1H-pyrazol-4-yl)oxazole-4-carboxamide;

I-25: N-(1-(2-(2,2-difluoroethoxy)ethyl)-3-(pyridin-2-yl)-1H-pyrazol-4-yl)-2-(1H-pyrazol-4-yl)oxazole-4-carboxamide;

I-26: N-(3-(3,6-difluoropyridin-2-yl)-1-((1r,3r)-3-ethoxycyclobutyl)-1H-pyrazol-4-yl)-2-(1H-pyrazol-4-yl)oxazole-4-carboxamide;

I-27: N-(1-((1r,4r)-4-hydroxycyclohexyl)-3-(pyrazin-2-yl)-1H-pyrazol-4-yl)-2-(1H-pyrazol-4-yl)oxazole-4-carboxamide;

I-28: N-(1-((1r,4r)-4-ethoxycyclohexyl)-3-(3,5,6-trifluoropyridin-2-yl)-1H-pyrazol-4-y1)-2-(1H-pyrazol-4-yl)oxazole-4-carboxamide;

I-29: N-(3-(4,6-difluoropyridin-2-yl)-1-((1r,4r)-4-ethoxycyclohexyl)-1H-pyrazol-4-yl)-2-(1H-pyrazol-4-yl)oxazole-4-carboxamide;

I-30: N-(1-((1r,4r)-4-morpholinocyclohexyl)-3-(pyrazin-2-yl)-1H-pyrazol-4-yl)-2-(1H-pyrazol-4-yl)oxazole-4-carboxamide;

I-31: N-(1-((1r,4r)-4-ethoxycyclohexyl)-3-(3-fluoro-6-(trifluoromethyl)pyridin-2-yl)-1H-pyrazol-4-yl)-2-(1H-pyrazol-4-yl)oxazole-4-carboxamide;

I-32: N-(1-((1r,4r)-4-ethoxycyclohexyl)-3-(pyrazin-2-yl)-1H-pyrazol-4-yl)-2-(5-fluoro-1H-pyrazol-4-yl)oxazole-4-carboxamide;

I-33: N-(1-((1r,3r)-3-morpholinocyclobutyl)-3-(pyrazin-2-yl)-1H-pyrazol-4-yl)-2-(1H-pyrazol-4-yl)oxazole-4-carboxamide;

I-34: N-(1-((1s,3s)-3-morpholinocyclobutyl)-3-(pyrazin-2-yl)-1H-pyrazol-4-yl)-2-(1H-pyrazol-4-yl)oxazole-4-carboxamide;

I-35: 2-(3-fluoro-1H-pyrazol-4-yl)-N-(1-((1r,4r)-4-morpholinocyclohexyl)-3-(pyrazin-2-y1)-1H-pyrazol-4-yl)oxazole-4-carboxamide formic acid salt;

I-36: N-(3-(3,6-difluoropyridin-2-yl)-1-((1s,4s)-4-(4-methylpiperazin-l-yl)cyclohexyl)-1H-pyrazol-4-yl)-2-(1H-pyrazol-4-yl)oxazole-4-carboxamide;

I-37: N-(3-(3,6-difluoropyridin-2-yl)-1-((1r,4r)-4-morpholinocyclohexyl)-1H-pyrazol-4-y1)-2-(1H-pyrazol-4-yl)oxazole-4-carboxamide;

I-38: N-(1-((1s,3s)-3-hydroxycyclobutyl)-3-(pyrazin-2-yl)-1H-pyrazol-4-yl)-2-(1H-pyrazol-4-yl)oxazole-4-carboxamide; or I-39: 2-(3-fluoro-1H-pyrazol-4-yl)-N-(1-((1r,4r)-4-morpholinocyclohexyl)-3-(pyrazin-2-y1)-1H-pyrazol-4-yl)oxazole-4-carboxamide.

20. A composition, comprising a compound according to claim 1 and a pharmaceutically acceptable excipient.

21. The composition of claim 20, further comprising an additional therapeutic agent.

* * * * *